United States Patent
Lee et al.

(10) Patent No.: US 12,090,171 B2
(45) Date of Patent: *Sep. 17, 2024

(54) ANTIBODY OR ANTIGEN BINDING FRAGMENT THEREOF FOR SPECIFICALLY RECOGNIZING B CELL MALIGNANCY, CHIMERIC ANTIGEN RECEPTOR COMPRISING SAME AND USE THEREOF

(71) Applicant: ABCLON INC., Seoul (KR)

(72) Inventors: Jong Seo Lee, Gyeonggi-do (KR); Kyu Tae Kim, Gyeonggi-do (KR); Bong Kook Ko, Seoul (KR); Ki Hyun Kim, Seoul (KR)

(73) Assignee: ABCLON INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/075,648

(22) Filed: Dec. 6, 2022

(65) Prior Publication Data
US 2023/0099646 A1 Mar. 30, 2023

Related U.S. Application Data

(63) Continuation of application No. 16/768,412, filed as application No. PCT/KR2018/015445 on Dec. 6, 2018, now Pat. No. 11,534,462.

(30) Foreign Application Priority Data

Dec. 6, 2017 (KR) .................. 10-2017-0166969

(51) Int. Cl.
*A61K 35/17* (2015.01)
*A61P 31/14* (2006.01)
(Continued)

(52) U.S. Cl.
CPC .............. *A61K 35/17* (2013.01); *A61P 31/14* (2018.01); *C07K 14/7051* (2013.01); *C07K 16/2803* (2013.01); *C12N 15/86* (2013.01)

(58) Field of Classification Search
CPC .......... A61K 35/17; A61P 35/00; A61P 31/14; C07K 14/7051; C07K 16/2803;
(Continued)

(56) References Cited

U.S. PATENT DOCUMENTS 7,169,894 B2 * 1/2007 Martin .............. G01N 33/6803
435/7.1
8,097,703 B2 1/2012 Rao-Naik et al.
(Continued)

FOREIGN PATENT DOCUMENTS

CN 106554414 A 4/2017
JP 2008-546647 A 12/2008
(Continued)

OTHER PUBLICATIONS

Kalos, et al. (2011) "T Cells with Chimeric Antigen Receptors Have Potent Antitumor Effects and Can Establish Memory in Patients with Advanced Leukemia." *Sci Transl Med*, 3(95):1-21 (Aug. 10, 2011).

(Continued)

*Primary Examiner* — Scarlett Y Goon
*Assistant Examiner* — Audrey L Buttice
(74) *Attorney, Agent, or Firm* — Harness, Dickey & Pierce, P.L.C.

(57) ABSTRACT

The present invention relates to a new antibody or an antigen binding fragment thereof for use in the treatment of cancer by targeting a B cell malignancy, a chimeric antigen receptor comprising the same, and a use of the same. The antibody of the present invention is an antibody for specifically binding to CD19 that is highly expressed in cancer cells (particularly, (Continued)

blood cancer), has very low homology to a CDR sequence thereof compared to a CDR sequence of a conventional CD19 target antibody so that the sequence thereof is unique, and specifically binds to an epitope that is different from a FMC63 antibody fragment binding to CD19 of the conventional art. A cell expressing the chimeric antigen receptor comprising an anti-CD19 antibody or the antigen binding fragment of the present invention induces immune cell activity in response to a positive cell line expressing CD19, and thus may be utilized as a CAR-immune cell therapeutic agent.

14 Claims, 18 Drawing Sheets

Specification includes a Sequence Listing.

(51) Int. Cl.
  *C07K 14/725* (2006.01)
  *C07K 16/28* (2006.01)
  *C12N 15/86* (2006.01)
(58) Field of Classification Search
  CPC ............... C07K 16/28; C07K 16/2896;
    C07K 2319/03; C07K 2319/33; C07K
    2317/622; C12N 15/86; C12N 2510/00;
    C12N 5/0636
  See application file for complete search history.

(56) References Cited

U.S. PATENT DOCUMENTS

| | | | |
|---|---|---|---|
| 8,679,492 | B2 | 3/2014 | Blein et al. |
| 9,074,002 | B2 | 7/2015 | Tonks et al. |
| 9,701,758 | B2 | 7/2017 | Cooper et al. |
| 2006/0280738 | A1 | 12/2006 | Tedder |
| 2009/0246195 | A1 | 10/2009 | Tedder |
| 2012/0164673 | A1 | 6/2012 | Tonks et al. |
| 2014/0271635 | A1* | 9/2014 | Brogdon .......... C07K 14/70503 536/23.53 |
| 2016/0152723 | A1 | 6/2016 | Chen et al. |

FOREIGN PATENT DOCUMENTS

| | | |
|---|---|---|
| JP | 2016-520074 | 7/2016 |
| KR | 10-2007-0114144 A | 11/2007 |
| KR | 10-2011-0104032 A | 9/2011 |
| KR | 10-2011-0125664 A | 11/2011 |
| KR | 10-2015-0132850 A | 11/2015 |
| KR | 10-2017-0057298 A | 5/2017 |
| WO | WO-2010/126590 A1 | 11/2010 |
| WO | WO-2010126590 A1 * | 11/2010 ............. C07K 16/40 |
| WO | WO-2014/184143 A1 | 11/2014 |
| WO | WO-2016/139487 A1 | 9/2016 |
| WO | WO-2017/066136 A2 | 4/2017 |

OTHER PUBLICATIONS

Kochenderfer, et al. (2010) "Eradication of B-lineage cells and regression of lymphoma in a patient treated with autologous T cells genetically engineered to recognize CD19." *Blood*, 116(20):4099-4102, (Nov. 18, 2010).
Kochenderfer, et al. (2012) "B-cell depletion and remissions of malignancy along with cytokine-associated toxicity in a clinical trial of anti-CD19 chimeric-antigen-receptor-transduced T cells." *Blood*, 119(12):2709-2720, (Mar. 22, 2012).
Kochenderfer, et al. (2013) "Treating B-cell cancer with T cells expressing anti-CD19 chimeric antigen receptors." *Nat Rev Clin Oncol*, 10(5):267-276, (May 2013).
Maude, et al. (2014) "Chimeric Antigen Receptor T Cells for Sustained Remissions in Leukemia." *N Engl J Med*, 371:16, pp. 1507-1517. (Oct. 16, 2014).
Nicholson, et al. (1997) "Construction and characterisation of a functional CD19 specific single chain Fv fragment for immunotherapy of B lineage leukaemia and lymphoma." *Molecular Immunology*, 34(16-17):1157-1165.
Porter, et al. (2011) "Chimeric Antigen Receptor-Modified T Cells in Chronic Lymphoid Leukemia." *N Engl J Med*, 365:8 pp. 725-733, (Aug. 25, 2011).
Topp, et al. (2014) "Phase II Trial of the Anti-CD19 Bispecific T Cell-Engager Blinatumomab Shows Hematologic and Molecular Remissions in Patients With Relapsed or Refractory B-Precursor Acute Lymphoblastic Leukemia." *Journal of Clinical Oncology*, 32(36):4134-4142.
International Search Report from corresponding PCT Application No. PCT/KR2018/015445, dated May 31, 2019, with English Translation.
De Oliveira, et al. (2013) "A CD19/Fc fusion protein for detection of anti-CD19 chimeric antigen receptors.", *Journal of Translational Medicine*, 11:23, pp. 1-9.
Notice of Allowance of Korean Patent Application No. 10-2018-0156433, issued on Jul. 10, 2020.
Extended European Search Report from correpsonding European Patent Application No. 18886531.52, dated Jan. 22, 2021.
Office Action from corresponing Japanese Patent Application No. 2020-530356, issued on May 18, 2021.
2nd Office Action from corresponding Japanese Patent Application No. 2020-530356, issued on Jan. 5, 2022.
Office Action from corresponding U.S. Appl. No. 16/768,412, dated Jul. 13, 2022.
Notice of Allowance from corresponding U.S. Appl. No. 16/768,412, dated Jul. 13, 2022.Office Action from corresponding U.S. Appl. No. 16/768,412, dated Jul. 13, 2022.
Emmons, K. M., et al (Mar. 2017) Realizing the Potential of Cancer Prevention—The Role of Implementation Science N Engl J Med 376(10); 986-990 (Year: 2017).
Cuzick, J. (Aug. 2017) Preventive therapy for cancer Lancet Oneal 18; e472-e482 (Year: 2017).
Chailyan, A., et al (2011) The association of heavy and light chain variable domains in antibodies: implications for antigen specificity FEBS Journal 278; 2858-2866 (Year: 2011).
Katz Ben-Zion et al: "Therapeutic targeting of CD19 in hematological malignancies: past, present, future and beyond", Leukemia & Lymphoma, vol. 55, No. 5, May 1, 2014 (May 1, 2014), pp. 999-1006, XP009187786.
Office Action from corresponding European Patent Application No. 18 886 531.5, dated May 25, 2023.
Office Action from corresponding Chinese Patent Application No. 201880079137.7, dated Jan. 18, 2023.

\* cited by examiner

|      | Signal peptide | scFv | Hinge/Spacer | TM | Co-stimulatory | | |
|------|----------------|------|--------------|-----|----------------|------|------|
| CAR1 | CD8 | scFv | CD8 | CD8 | CD137 | CD3z | |
| CAR2 | CD8 | scFv | CD28 | CD8 | CD137 | CD3z | |
| CAR3 | CD8 | scFv | Fc | CD8 | CD137 | CD3z | |
| CAR4 | CD8 | scFv | CD8 | CD28 | CD28 | CD3z | |
| CAR5 | CD8 | scFv | CD8 | ICOS | ICOS | CD3z | |
| CAR6 | CD8 | scFv | CD8 | CD28 | CD28 | CD137 | CD3z |
| CAR7 | CD8 | scFv | CD8 | ICOS | CS3 | CD137 | CD3z |

CAR1–CAR5: 2nd-G CAR
CAR6–CAR7: 3rd-G CAR

FIG. 9

ANTIBODY OR ANTIGEN BINDING FRAGMENT THEREOF FOR SPECIFICALLY RECOGNIZING B CELL MALIGNANCY, CHIMERIC ANTIGEN RECEPTOR COMPRISING SAME AND USE THEREOF

CROSS-REFERENCE TO RELATED APPLICATIONS

This application is a continuation application of U.S. patent application Ser. No. 16/768,412, filed May 29, 2020, which is a national phase application of PCT Application No. PCT/KR2018/015445, filed on Dec. 6, 2018, which claims the benefit and priority to Korean Patent Application No. 10-2017-0166969, filed Dec. 6, 2017. The entire disclosures of the applications identified in this paragraph are incorporated herein by references.

FIELD

The present disclosure relates to a novel antibody for targeting and treating B cell malignancy, or an antigen binding fragment thereof, a chimeric antigen receptor comprising the same, and a use thereof.

BACKGROUND

B cell malignancies are tumors generated in B cells, which are a type of cell lineage responsible for the immune system of the body. Such a B cell malignancy breaks a normal immune system to decrease the immunity against antigens invading from the outside, finally causing the death of patients. For example, acute lymphocytic leukemia (ALL), which is one of B cell malignancies, refers to a disease in which the lymphoid line of white blood cells becomes malignant, grows in the bone marrow, and spreads to peripheral blood, thus invading the liver, the spleen, the lymph, the cerebrum, the cerebellum, the spinal cord, and so on. Representative of therapies for acute lymphocytic leukemia are chemotherapy, targeted therapy, and allogeneic stem cell transplantation. These therapies have been improved to carry the survival rate of child patients to over 85%. However, there are patients unresponsive to conventional therapies or patients in recurrence, and acute lymphocytic leukemia is the most common cause of cancer and death from cancer among children.

Most lymphoma/leukemia generated from B cell malignancies as well as acute lymphocytic leukemia are characterized by the expression of CD19 antigen on the surface of the cells. On the basis of this feature, various therapies designed to recognize CD19 antigen have been tried. Among such CD19 target therapies, CAR-T cell therapy was used for treatment of blood cancer through the cell death induction mechanism thereof as it was found to increase cytotoxicity for target cells in acute leukemia patients unresponsive to conventional therapies. A high cure rate (27 of 30 cases) was reported as a clinical test result of the therapy. However, in spite of the high response rate thereof, conventional CD19 CAR-T cell therapies were reported to have the problem of causing resistance in 10-20% of the patients treated therewith (Maude et al., N Eng J Med, 2014, 371:1507; Topp et al., J Clin Oncol, 2014, 32:4134). Therefore, there is a need for the development of a novel antibody that binds to a site different from those bound by conventional CD19 targeting antibodies.

Under the background, the present inventors developed an antigen-binding fragment that selectively recognizes CD19-expressing B cells among B cell malignancies and found that the developed antibody binds to CD19 at an epitope different from that targeted by the conventional antibody FMC63. In addition, cytotoxic T cells that express a chimeric antigen receptor comprising the developed antigen-binding fragment retain cytotoxicity.

DETAILED DESCRIPTION

Technical Problem

Leading to the present disclosure, intensive and thorough research into development of a novel antibody binding to a different epitope of CID19 and a chimeric antigen receptor using the same, conducted by the present inventors in order to solve the problem of resistance to conventional CD19-specific CAR-T therapies, resulted in the finding that CD19_12.18 antibody and variants thereof bind to a CD19 epitope site different from those that the conventional antibody FMC63 targets.

Therefore, a purpose of the present disclosure is to provide a novel anti-CD19 antibody and an antigen-binding fragment thereof.

Another purpose of the present disclosure is to provide a chimeric antigen receptor comprising the anti-CD19 antibody or an antigen-binding fragment thereof and dividable into an extracellular domain, a transmembrane domain, and an intracellular signaling domain.

Another purpose of the present disclosure is to provide a pharmaceutical composition comprising cells expressing the chimeric antigen receptor.

Another purpose of the present disclosure is to provide a nucleic acid molecule encoding the antibody, the antigen-binding fragment thereof, or the chimeric antigen receptor.

Another purpose of the present disclosure is to provide a recombinant vector carrying a nucleic acid molecule encoding the antibody, the antigen-binding fragment thereof, or the chimeric antigen receptor.

Another purpose of the present disclosure is to provide a host cell transformed with the recombinant vector.

Other purpose and advantages of the present disclosure will become more apparent from the following detailed description, claims and drawings.

Technical Solution

Claimed in the present disclosure is the disclosure as set forth below:
1. An anti-CD19 antibody or an antigen-binding fragment thereof, comprising the following:
   (a) a heavy chain variable region comprising the following heavy chain complementarity determining region (CDR) amino acid sequences: CDRH1 of SEQ ID NO: 1 and CDRH2 of SEQ ID NO: 2; and
   (b) a light chain variable region comprising the following light chain CDR amino acid sequence: CDRL1 of SEQ ID NO: 4.
2. The anti-CD19 antibody or the antigen-binding fragment thereof as set forth in claim 1, wherein the heavy chain variable region further comprises CDRH3 comprising any one of the amino acid sequences of SEQ ID NOS: 3 and 30 to 35.
3. The anti-CD19 antibody or the antigen-binding fragment thereof as set forth in claim 1, wherein the light chain variable region further comprises CDRL2 comprising any one of the amino acid sequences of SEQ ID NOS: 5 and 36 to 39.

4. The anti-CD19 antibody or the antigen-binding fragment thereof as set forth in claim 1, wherein the light chain variable region further comprises CDRL3 comprising any one of the amino acid sequences of SEQ ID NOS: 6, 40, and 41.

5. The anti-CD19 antibody or the antigen-binding fragment thereof as set forth in any one of claims 1 to 4, wherein the heavy chain variable region comprises any one of the sequences of SEQ ID NOS: 7, 42, 46, 50, 54, 58, 62, 66, and 70.

6. The anti-CD19 antibody or the antigen-binding fragment thereof as set forth in any one of claims 1 to 4, wherein the light chain variable region comprises any one of the amino acid sequences of SEQ ID NOS: 8, 43, 47, 51, 55, 59, 63, 67, and 71.

7. An anti-CD19 antibody or an antigen-binding fragment thereof, binding specifically to CD19 and shielding CD19 from being bound by an antibody or an antigen-binding fragment thereof which binds to at least one amino acid residue selected from the group consisting of T51, S53, E55, L58, K59, and K63 on the amino acid sequence of SEQ ID NO: 92.

8. The anti-CD19 antibody or the antigen-binding fragment thereof as set forth in claim 7, wherein the anti-CD19 antibody or the antigen-binding fragment thereof binds specifically to CD19 and shields CD19 from being bound by an antibody or an antigen-binding fragment thereof which binds to at least two amino acid residues selected from the group consisting of T51, S53, E55, L58, K59, and K63 on the amino acid sequence of SEQ ID NO: 92.

9. The anti-CD19 antibody or the antigen-binding fragment thereof as set forth in claim 7, wherein the anti-CD19 antibody or the antigen-binding fragment thereof binds specifically to CD19 and shields CD19 from being bound by an antibody or an antigen-binding fragment thereof which binds to at least three amino acid residues selected from the group consisting of T51, S53, E55, L58, K59, and K63 on the amino acid sequence of SEQ ID NO: 92.

10. The anti-CD19 antibody or the antigen-binding fragment thereof as set forth in claim 7, wherein the anti-CD19 antibody or the antigen-binding fragment thereof binds specifically to CD19 and shields CD19 from being bound by an antibody or an antigen-binding fragment thereof which binds to at least one amino acid residue selected from the group consisting of L58, K59, and K63 on the amino acid sequence of SEQ ID NO: 92.

11. The anti-CD19 antibody or the antigen-binding fragment thereof as set forth in claim 7, wherein the anti-CD19 antibody or the antigen-binding fragment thereof binds specifically to CD19 and shields CD19 from being bound by an antibody or an antigen-binding fragment thereof which binds to at least two amino acid residues selected from the group consisting of L58, K59, and K63 on the amino acid sequence of SEQ ID NO: 92.

12. The anti-CD19 antibody or the antigen-binding fragment thereof as set forth in claim 7, wherein the anti-CD19 antibody or the antigen-binding fragment thereof specifically targets CD19 and binds to at least one amino acid residue selected from the group consisting of T51, S53, E55, L58, K59, and K63 on the amino acid sequence of SEQ ID NO: 92.

13. The anti-CD19 antibody or the antigen-binding fragment thereof as set forth in claim 7, wherein the anti-CD19 antibody or the antigen-binding fragment thereof specifically targets CD19 and binds to at least two amino acid residues selected from the group consisting of T51, S53, E55, L58, K59, and K63 on the amino acid sequence of SEQ ID NO: 92.

14. The anti-CD19 antibody or the antigen-binding fragment thereof as set forth in claim 7, wherein the anti-CD19 antibody or the antigen-binding fragment thereof specifically targets CD19 and binds to at least three amino acid residues selected from the group consisting of T51, S53, E55, L58, K59, and K63 on the amino acid sequence of SEQ ID NO: 92.

15. The anti-CD19 antibody or the antigen-binding fragment thereof as set forth in claim 7, wherein the anti-CD19 antibody or the antigen-binding fragment thereof specifically targets CD19 and binds to at least one amino acid residue selected from the group consisting of L58, K59, and K63 on the amino acid sequence of SEQ ID NO: 92.

16. The anti-CD19 antibody or the antigen-binding fragment thereof as set forth in claim 7, wherein the anti-CD19 antibody or the antigen-binding fragment thereof specifically targets CD19 and binds to at least two amino acid residues selected from the group consisting of L58, K59, and K63 on the amino acid sequence of SEQ ID NO: 92.

17. The anti-CD19 antibody or the antigen-binding fragment thereof as set forth in claim 7, being the antibody or the antigen-binding fragment according to any one of claims 1 to 6.

18. The anti-CD19 antibody or the antigen-binding fragment thereof as set forth in any one of claims 1 to 17, wherein the anti-CD19 antibody or the antigen-binding fragment thereof does not bind to an epitope to which FMC63 antibody binds.

19. The anti-CD19 antibody or the antigen-binding fragment thereof as set forth in claim 18, being a human antibody or a humanized antibody.

20. The anti-CD19 antibody or the antigen-binding fragment thereof as set forth in claim 18, being an scFv.

21. A nucleic acid molecule, encoding the anti-CD19 antibody or the antigen-binding fragment thereof according to any one of claims 1 to 20.

22. A recombinant vector, carrying the nucleic acid molecule of claim 21.

23. A host cell, transformed with the recombinant vector of claim 22.

24. A CD19-specific chimeric antigen receptor, comprising the following:
(a) an extracellular domain comprising the anti-CD19 antibody or the antigen-binding fragment thereof according to claim 1;
(b) a transmembrane domain; and
(c) an intracellular signaling domain.

25. The CD19-specific chimeric antigen receptor as set forth in claim 24, wherein the transmembrane domain is a transmembrane domain of a protein selected from the group consisting of alpha, beta, or zeta chain of T-cell receptor, CD27, CD28, CD3 epsilon, CD45, CD4, CD5, CD8(CD8α), CD9, CD16, CD22, CD33, CD37, CD64, CD80, CD86, CD134, CD137, and CD154.

26. The CD19-specific chimeric antigen receptor as set forth in claim 24, wherein the intracellular signaling domain is a CD3ζ (CD3 zeta) chain-derived domain.

27. The CD19-specific chimeric antigen receptor as set forth in claim 24, wherein the intracellular signaling domain further comprises a costimulatory molecule selected from the group consisting of OX40 (CD134), CD2, CD27, CD28, CD5, ICAM-1, LFA-1 (CD11a/CD18), and 4-1BB (CD137).

28. A cell, expressing the chimeric antigen receptor of any one of claims 24 to 27.
29. The cell as set forth in claim 28, being an immune cell selected from the group consisting of a dendritic cell, a killer dendritic cell, a mast cell, an NK-cell, a B-cell or an inflammatory T-lymphocyte, a cytotoxic T-lymphocyte, a regulatory T-lymphocyte, and a helper T-lymphocyte.
30. A pharmaceutical composition for prevention or treatment of a CD19 positive cell-associated disease, an autoimmune disease, or an inflammatory disease, the composition comprising the antibody or the antigen-binding fragment thereof according to any one of claims 1 to 20.
31. The pharmaceutical composition as set forth in claim 30, wherein the CD19 positive cell-associated disease is B cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.
32. The pharmaceutical composition as set forth in claim 30, wherein the autoimmune disease or the inflammatory disease is selected from the group consisting of multiple sclerosis, rheumatoid arthritis, and systemic lupus erythematosus (SLE).
33. A pharmaceutical composition for prevention or treatment of a CD19 positive cell-associated disease, an autoimmune disease, or an inflammatory disease, the composition comprising the cell of claim 28 or 29.
34. The pharmaceutical composition as set forth in claim 33, wherein the CD19 positive cell-associated disease is B cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.
35. The pharmaceutical composition as set forth in claim 33, wherein the autoimmune disease or the inflammatory disease is selected from the group consisting of multiple sclerosis, rheumatoid arthritis, and systemic lupus erythematosus (SLE).
36. A nucleic acid molecule, encoding the chimeric antigen receptor of claims 24 to 27.
37. A recombinant vector, carrying the nucleic acid molecule of claim 36.
38. A host cell, transformed with the recombinant vector of claim 37.
39. A method for treatment of a CD19 positive cell-associated disease, an autoimmune disease, or an inflammatory disease, the method comprising a step of administering the composition of any one of claims 30 to 35 to a subject in need thereof.
40. The method as set forth in claim 39, wherein the CD19 positive cell-associated disease is B cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.
41. The method as set forth in claim 39, wherein the autoimmune disease or an inflammatory disease is selected from multiple sclerosis, rheumatoid arthritis, and systemic lupus erythematosus (SLE).
42. The method as set forth in claim 39, wherein the subject is a mammal or a human.

According to an aspect thereof, the present disclosure provides an anti-CD19 antibody or an antigen-binding fragment thereof, comprising the following:
(a) a heavy chain variable region comprising the following heavy chain complementarity determining region (CDR) amino acid sequences: CDRH1 of SEQ ID NO: 1 and CDRH2 of SEQ ID NO: 2; and
(b) a light chain variable region comprising the following light chain CDR amino acid sequence: CDRL1 of SEQ ID NO: 4.

In an embodiment of the present disclosure, the heavy chain variable region further comprises CDRH3 comprising any one of the amino acid sequences of SEQ ID NOS: 3 and 30 to 35.

In another embodiment of the present disclosure, the light chain variable region further comprises CDRL2 comprising any one of the amino acid sequences of SEQ ID NOS: 5 and 36 to 39.

In another embodiment of the present disclosure, the light chain variable region further comprises CDRL3 comprising any one of the amino acid sequences of SEQ ID NOS: 6, 40, and 41.

In another embodiment of the present disclosure, the heavy chain variable region comprises any one of the sequences of SEQ ID NOS: 7, 42, 46, 50, 54, 58, 62, 66, and 70.

In another embodiment of the present disclosure, the light chain variable region comprises any one of the amino acid sequences of SEQ ID NOS: 8, 43, 47, 51, 55, 59, 63, 67, and 71.

According to an aspect thereof, the present disclosure provides an anti-CD19 antibody or an antigen-binding fragment thereof which binds specifically to CD19 and shields CD19 from being bound by an antibody or an antigen-binding fragment thereof which binds to at least one amino acid residue selected from the group consisting of T51, S53, E55, L58, K59, and K63 on the amino acid sequence of SEQ ID NO: 92. The amino acid sequence of SEQ ID NO: 92 comes from human B lymphocyte antigen CD19 and is known as ID: P15391 in UniProtKB.

The antibody or the antigen-binding fragment of the present disclosure binds specifically to CD19 and shields CD19 from being bound by an antibody or an antigen-binding fragment thereof which binds to at least two amino acid residues selected from the group consisting of T51, S53, E55, L58, K59, and K63 on the amino acid sequence of SEQ ID NO: 92.

The antibody or the antigen-binding fragment of the present disclosure binds specifically to CD19 and shields CD19 from being bound by an antibody or an antigen-binding fragment thereof which binds to at least three amino acid residues selected from the group consisting of T51, S53, E55, L58, K59, and K63 on the amino acid sequence of SEQ ID NO: 92.

The antibody or the antigen-binding fragment of the present disclosure binds specifically to CD19 and shields CD19 from being bound by an antibody or an antigen-binding fragment thereof which binds to at least one amino acid residue selected from the group consisting of L58, K59, and K63 on the amino acid sequence of SEQ ID NO: 92.

The antibody or the antigen-binding fragment of the present disclosure binds specifically to CD19 and shields CD19 from being bound by an antibody or an antigen-binding fragment thereof which binds to at least two amino acid residues selected from the group consisting of L58, K59, and K63 on the amino acid sequence of SEQ ID NO: 92.

In an embodiment of the present disclosure, the antibody or the antigen-binding fragment thereof specifically targets CD19 and binds to at least one amino acid residue selected from the group consisting of T51, S53, E55, L58, K59, and K63 on the amino acid sequence of SEQ ID NO: 92.

In another embodiment of the present disclosure, the antibody or the antigen-binding fragment thereof specifically targets CD19 and binds to at least two amino acid residues selected from the group consisting of T51, S53, E55, L58, K59, and K63 on the amino acid sequence of SEQ ID NO: 92.

In another embodiment of the present disclosure, the antibody or the antigen-binding fragment thereof specifically targets CD19 and binds to at least three amino acid residues selected from the group consisting of T51, S53, E55, L58, K59, and K63 on the amino acid sequence of SEQ ID NO: 92.

In another embodiment of the present disclosure, the antibody or the antigen-binding fragment thereof specifically targets CD19 and binds to at least one amino acid residue selected from the group consisting of L58, K59, and K63 on the amino acid sequence of SEQ ID NO: 92.

In another embodiment of the present disclosure, the antibody or the antigen-binding fragment thereof specifically targets CD19 and binds to at least two amino acid residues selected from the group consisting of L58, K59, and K63 on the amino acid sequence of SEQ ID NO: 92.

As confirmed in an example of the present disclosure, the anti-CD19 antibody of the present disclosure or an antigen-binding fragment thereof (e.g. CD19_12.18) exhibited decreased binding affinity for mtCD19(T51V), mtCD19 (S53C), mtCD19(E55D), mtCD19(L58F), mtCD19(K59E), and mtCD19(K63N), which were modified from the hCD19 consisting of the amino acid sequence of SEQ ID NO: 92 at T51, S53, E55, L58, K59, and K63 residues, respectively. From the result, it was observed that the six amino acid residues function as important key residues responsible for the epitope site at which the anti-CD19 antibody or antigen-binding fragment of the present disclosure binds to CD19. Of them, the amino acid residues L58, K59, and K63 were found to be more important key residues responsible for the binding of the antibody or the antigen-binding fragment to CD19 as the binding affinity was significantly decreased for mutant hCD19 in which L58, K59, and K63 were modified. Therefore, the anti-CD19 antibody of the present disclosure or an antigen-binding fragment thereof binds to hCD19 including the amino acid sequence of SEQ ID NO: 92 at one, two, three or more amino acid residues selected from the group consisting of T51, S53, E55, L58, K59, and K63 on the sequence. In detail, the anti-CD19 antibody of the present disclosure or an antigen-binding fragment thereof binds to hCD19 including the amino acid sequence of SEQ ID NO: 92 at least one amino acid residue selected from the group consisting of L58, K59, and K63 on the sequence. As a result, the anti-CD19 antibody of the present disclosure or an antigen-binding fragment thereof shields CD19 from being bound by an antibody or an antibody-binding fragment thereof which binds to hCD19 including the amino acid sequence of SEQ ID NO: 92 at least one selected from the group consisting of T51, S53, E55, L58, K59, and K63 on the amino acid sequence. More particularly, the anti-CD19 antibody of the present disclosure or an antigen-binding fragment thereof shields CD19 from being bound by an antibody or an antigen-binding fragment thereof which binds to hCD19 including the amino acid sequence of SEQ ID NO: 92 at least one selected from the group consisting of L58, K59, and K63 on the amino acid sequence.

In an embodiment of the present disclosure, CD19_12.18 antibody or a variant thereof according to the present disclosure binds to CD19 at an epitope different from that of FMC63, which is an antibody used in a chimeric antigen receptor. The antibody of the present disclosure and variants thereof target the same epitope or compete with each other for binding to the same epitope in CD19.

As will be demonstrated in the Examples below, the anti-CD19 antibody or antigen-binding fragment of the present disclosure was greatly lowered in binding affinity for mtCD19(T51V), mtCD19(S53C), mtCD19(E55D), mtCD19(L58F), mtCD19(K59E), and mtCD19(K63N), which are hCD19 including the amino acid sequence of SEQ ID NO: 92 modified at amino acid residues T51, S53, E55, L58, K59, and K63, respectively. However, the binding affinity was maintained intact in FMC63 antibody. In addition, the antibody of the present disclosure or an antigen-binding fragment thereof normally binds to mtCD19 (H218R/KSS) whereas FMC63 antibody shows poor binding affinity for mtCD19(H218R/KSS). Therefore, the anti-CD19 antibody of the present disclosure or an antigen-binding fragment thereof does not bind to the epitope to which FMC63 antibody binds.

In another Example, an ELISA plate was coated with a the CD19_12.18 antibody variant (i.e., CD19_1218.81 antibody) of the present disclosure to which CD19-ECD-Ck alone or in combination with CD19_1218 antibody was added, followed by competitive ELISA. CD19_1218 antibody competed with CD19_1218.81 antibody for binding to CD19-ECD-Ck. As a result, a low level of CD19-ECD-Ck bound by CD19_1218 antibody was detected. Therefore, the anti-CD19 antibody and a variant thereof bind to the same epitope or compete with each other for the same epitope.

In the present disclosure, the antibody or antigen-binding fragment may be a human antibody or a humanized entity. In addition, the antibody or antigen-binding fragment of the present disclosure may be scFv, but is not limited thereto.

In the present disclosure, the antibody or the antigen-binding fragment was constructed by CDR grafting in which complementarity determining regions (CDRs) of conventional antibodies developed in mice into a framework more stable than those of the conventional antibodies. "CDR grafting" is a representative technique for humanizing a non-human antibody in order to solve the problem that murine monoclonal antibodies are neutralized due to the immunogenicity thereof upon use in human antibodies. That is, CDR grafting is to graft a CDR region of an animal antibody to the framework of human antibodies.

An antibody according to an aspect of the present disclosure is CD19_12.18 antibody or a variant thereof. In detail, the variant of CD19_12.18 antibody is hzCD19_1218.81, hzCD19_1218.82, hzCD19_1218.81.12, hzCD19_1218.81.17, hzCD19_1218.81.52, hzCD19_1218.81.55, hzCD19_1218.81.64, or hzCD19_1218.81.79. Amino acid sequences and nucleotide sequences of CDRs and light chain variable regions or heavy chain variable regions of the variants are given in the specification and the sequence listing appended.

In the specification, "FMC63" antibody is an example of murine anti-CD19 monoclonal antibodies (Nicholson et al., Molecular Immunology, 34(16-17): 1157-1165 (1997)). Variable regions of FMC63 monoclonal antibody have been used in CAR tested in clinical trials (e.g., see [Kochenderfer et al., Nature Review Clinical Oncol., 10(5); 267-276 (2013); Porter et al., New Eng. J. Med., 365(8): 725-733 (2011); Kalos et al., Science Translational Medicine, 3(95): 95ra73 (2011); Kochenderfer et al., Blood, 116(20): 4099-4102 (2010); and Kochenderfer et al., Blood, 119(12): 2709-2720 (2012)]).

As used herein, the term "antibody" used in context of CD19 refers to an antibody specific for CD19 and is intended to encompass not only a whole antibody form, but also an antigen-binding fragment thereof.

A whole antibody includes two full length light chain and two full length heavy chains where each light chain is linked to the heavy chain by disulfide bonds. The heavy chain constant region is divided into isotypes of gamma ($\gamma$), mu ($\mu$), alpha ($\alpha$), delta ($\delta$), and epsilon ($\epsilon$) types, which are further subtyped into gamma1 ($\gamma$1), gamma2 ($\gamma$2), gamma3 ($\gamma$3), gamma4 ($\gamma$4), alpha 1 ($\alpha$1), and alpha 2 ($\alpha$2). The light chain constant region is divided into kappa ($\kappa$) and lambda ($\lambda$) types.

As used herein, the term "antigen-binding fragments" refers to a fragment retaining the function of binding to an antigen and includes Fab, F(ab'), F(ab')2, and Fv. Of them, Fab (fragment antigen binding) is composed of one constant and one variable domain of each of the heavy and the light chain, the constant domain of the heavy chain being the first constant domain (CH1), and thus contains one antigen-binding site. Fab' is different from Fab in that the former comprises a hinge region including at least one cysteine residue at the C-terminal of the CH1 domain of a heavy chain. F(ab')2 is produced by a disulfide bond formation between cysteine residues in the hinge region of Fab'. Fv is an antibody fragment composed only of variable regions of a heavy and a light chain, which may be produced by a recombinant technology disclosed in the art. In Fv (two-chain Fv), variable regions of a light and heavy chain are linked by a non-covalent bond, and in a single chain Fv, variable regions of a light and heavy chain are linked by a covalent bond through a peptide linker or it may form a dimer structure like a two chain FV through a direct linkage at the C-terminal. These antibody fragments can be obtained through a proteinase treatment (for example, a whole antibody may be treated with a papain to obtain Fab fragments or with pepsin to obtain F(ab')2 fragment) or preferably constructed using a recombinant DNA technology.

Herein, examples of the antibody include a monoclonal antibody, a multispecific antibody, a human antibody, a humanized antibody, a chimeric antibody, a single-chain Fv (scFv), a single-chain antibody, an Fab, an F(ab'), a disulfide-linked Fv (sdFv), an anti-idiotype (anti-Id) antibody, and an epitope-binding fragment thereof, but are not limited thereto.

The term "heavy chain", as used herein, refers to a full length chain comprising three constant regions CH1, CH2 and CH3 and one variable region VH comprising an amino acid sequence which is sufficient for conferring specificity to an antigen as well fragments thereof. Also The term "light chain" as used herein refers to a full length chain comprising one constant region CL and one variable region VL comprising an amino acid sequence which is sufficient for conferring specificity to an antigen as well fragments thereof.

The term "variable region" or "variable domain", as used herein, refers to a domain on a heavy or a light chain of an antibody, which is responsible for binding the antibody to an antigen. Variable domains on the heavy and the light chain of a native antibody (VH and VL, respectively) are generally similar in structure and each include four conserved framework regions (FRs) and three hypervariable regions (HVRs) (Kindt et al., Kuby Immunology, $6^{th}$ edition, W. H. Freeman and Co., page 91 (2007)).

As used herein, the term "CDR" (complementarity determining region) refers to an amino acid sequence of the hypervariable regions on the immunoglobulin heavy and light chains (Kabat et al., Sequences of Proteins of Immunological Interest, 4th Ed., U.S. Department of Health and Human Services, National Institutes of Health (1987)). Three CDRs are included in each of the heavy chain (CDRH1, CDRH2, and CDRH3) and the light chain (CDRL1, CDRL2, and CDRL3). CDRs provides important contact residues with which the antibody binds to an antigen.

As used herein, the term "framework" or "FR" refers to variable domain residues other than hypervariable region (HVR) residues. The FR of the variable domain generally consists of four FR domains: FR1, FR2, FR3, and FR4. Thus, the HVR and FR sequences generally appear in the following sequence in VH:

FRH1 (framework region 1 of heavy chain)-CDRH1 (complementarity determining region 1 of heavy chain)-FRH2-CDRH2-FRH3-CDRH3-FRH4.

Also, HVR and FR sequences in VL (or Vk) are arranged in the order as follows: FRL1 (framework region 1 of light chain)-CDRL1(complementarity determining region 1 of light chain)-FRL2-CDRL2-FRL3-CDRL3-FRL4.

By the term "specifically binding" or wordings relevant thereto, it is intended that an antibody or a constituent thereof, such as an antigen binding fragment or scFv, forms a complex with an antigen that is relatively stable under physiologic conditions. Specific binding can be characterized by an equilibrium dissociation constant of at least about $1\times10^{-6}$ M or less (e.g., less KD means more strong binding). Methods for determining whether two molecules specifically bind are well known in the art and include, for example, equilibrium dialysis, surface plasmon resonance, and the like.

The term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

The term "human antibody", as used herein, refers to an antibody which possesses an amino acid sequence which corresponds to that of an antibody produced by a human or a human cell or derived from a non-human source that utilizes human antibody repertoires or other human antibody-encoding sequences.

The term "chimeric antibody" refers to an antibody in which a portion of the heavy and/or light chain is derived from a particular source or species, while the remainder of the heavy and/or light chain is derived from a different source or species.

In the context of specifically recognizing CD19, variants of the amino acid sequences listed in the sequence listing appended may fall within the scope of the anti-CD19 antibody or an antigen-binding fragment thereof according to the present disclosure. For example, a variation may be given to the amino acid sequence of an antibody in order to improve the binding affinity and/or other biological properties of the antibody. The variation includes a deletion, an addition, and/or a substitution of an amino acid residue on the amino acid sequence of the antibody.

Such amino acid variations may be provided on the basis of a relative similarity of amino acid side chains, e.g., hydrophobicity, hydrophilicity, charge, and size. As analyzed for size, shape, and type of amino acid side chains, it is clear that all of arginine, lysine and histidine residues are positively charged; alanine, glycine, and serine are similar in size; phenylalanine, tryptophan, and tyrosine have similar shapes. Accordingly, based on this consideration, arginine, lysine and histidine; alanine, glycine and serine; and phenylalanine, tryptophan and tyrosine may be considered to be biologically functional equivalents.

In making such variations, the hydropathic index of amino acids may be considered. Each amino acid has been assigned a hydropathic index on the basis of their hydrophobicity and charge characteristics: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art. It is known that similar biological activity is retained only upon substitution of certain amino acids for other amino acids having a similar hydropathic index. In making variations based upon the hydropathic index, the substitution of amino acids whose hydropathic indices are within ±2 is preferred, those which are within ±1 are particularly preferred, and those within ±0.5 are even more particularly preferred.

It also is understood in the art that substitutions between amino acids having similar hydrophilicity values may result in the generation of proteins having biologically equivalent activities.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making variations based upon similar hydrophilicity values, the substitution of amino acids whose hydrophilicity values are within ±2 is preferred, those which are within ±1 are particularly preferred, and those within ±0.5 are even more particularly preferred.

The amino acid exchanges in proteins that do not substantially change the activity of the molecule are well known in the art (H. Neurath, R. L. Hill, The Proteins, Academic Press, New York, 1979). The most common exchanges are found between amino acid residues: Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

According to an embodiment, the anti-CD19 antibody or the antigen-binding fragment of the present disclosure comprises: a heavy chain variable region containing at least one CDR including one amino acid sequence selected from SEQ ID NOS: 1 to 3 and SEQ ID NOS: 30 to 35; and a light chain variable region containing at least one CDR including one amino acid sequence selected from SEQ ID NOS: 4 to 6 and SEQ ID NOS: 36 to 41, and includes a monoclonal antibody, a multispecific antibody, a human antibody, a humanized antibody, a chimeric antibody, a single-chain Fv (scFv), a single-chain antibody, an Fab, an F(ab'), a disulfide-linked Fv (sdFv), an anti-idiotype (anti-Id) antibody, and an epitope-binding fragment thereof, but are not limited thereto.

In another embodiment, the anti-CD19 antibody or the antigen-binding fragment of the present disclosure comprises a heavy chain variable region including any one amino acid sequence of SEQ ID NOS: 7, 42, 46, 50, 54, 58, 62, 66, and 70.

In another embodiment, the anti-CD19 antibody or the antigen-binding fragment of the present disclosure comprises a light chain variable region including any one amino acid sequence of SEQ ID NOS: 8, 43, 47, 51, 55, 59, 63, 67, and 71.

In another embodiment, the anti-CD19 antibody or the antigen-binding fragment of the present disclosure is an anti-CD19 scFv.

In an exemplary embodiment of the present disclosure, the heavy chain variable region and the light chain variable region contained in the antibody or the antigen-binding fragment thereof are connected to each other via (Gly-Ser)n, (Gly2-Ser)n, (Gly3-Ser)n or (Gly4-Ser)n linker, wherein n is an integer of 1 to 6 and particularly 3 to 4, but is not limited thereto. The light chain variable region and the heavy chain variable region in scFv may be, for example, arranged as follows: light chain variable region-linker-heavy chain variable; or heavy chain variable region-linker-light chain variable region.

Being of very poor similarity to CDR sequences of conventional anti-CD19 antibodies or chimeric antigen receptors including the same, the CDR sequence of the antibody of the present disclosure is unique. For example, a BLAST search performed for CD19_12.18 antibody of the present disclosure on the NCBI website detected an antibody disclosed in U. S. Pat. No. 9,074,002 (SEQ ID NO: 29) as the most homologous antibody, but with the CDR sequence homology therebetween being just 81.7%. Moreover, the antibody disclosed in U. S. Pat. No. 9,074,002 binds to protein tyrosine phosphatase 1B (PTP1B), which is different from the target of the antibody of the present disclosure.

According to another embodiment thereof, the present disclosure provides a nucleic acid molecule encoding the anti-CD19 antibody or the antigen-binding fragment thereof.

According to an embodiment of the present disclosure, the nucleic acid molecule encoding the anti-CD19 antibody or the antigen-binding fragment thereof comprises at least one CDR-encoding nucleotide sequence selected from the group consisting of the nucleotide sequences of SEQ ID NOS: 10 to 12 and at least one CDR-encoding nucleotide sequence selected from the group consisting of the nucleotide sequences of SEQ ID NOS: 13 to 15.

According to another embodiment of the present disclosure, the nucleic acid molecule comprises a heavy chain variable region-encoding nucleotide sequence including a nucleotide sequence selected from the group consisting of SEQ ID NOS: 16, 44, 48, 52, 56, 60, 64, 68, and 72.

According to another embodiment of the present disclosure, the nucleic acid molecule comprises a heavy chain variable region-encoding nucleotide sequence including a nucleotide sequence selected from the group consisting of SEQ ID NOS: 17, 45, 49, 53, 57, 61, 65, 69, and 73.

According to another embodiment of the present disclosure, the nucleic acid molecule comprises a nucleotide sequence encoding the antibody or the antigen-binding fragment having SEQ ID NO: 18, but is not limited thereto.

The term "nucleic acid molecule", as used herein, is intended to encompass DNA (gDNA and cDNA) and RNA molecules. Nucleotides are the basic building block of the nucleic acid molecule and include sugar or base-modified analogues as well as natural nucleotides (Scheit, *Nucleotide Analogs*, John Wiley, New York(1980); Uhlman and Peyman, *Chemical Reviews*, 90:543-584(1990)).

It should be understood to a person skilled in the art that the nucleotide sequence coding for the antibody, the antigen-biding fragment thereof, or the chimeric antigen receptor polypeptide according to the present disclosure is any nucleotide sequence that encode an amino acid sequence constituting the chimeric antigen receptor molecule and is not limited to particular nucleotide sequences.

The reason is that even if the nucleotide sequence undergoes mutation, the expression of the mutated nucleotide sequence into a protein may not cause a change in the protein sequence. This is called the degeneracy of codons. Therefore, the nucleotide sequence includes nucleotide sequences containing functionally equivalent codons, codons encoding the same amino acids (e. g., arginine or serine are six different codons), or codons containing biologically equivalent amino acids.

According to an embodiment of the present disclosure, nucleotide sequences of nucleic acids coding for polypeptides of heavy chain CDRs, light chain CDRs, heavy chain variable regions, light chain variable regions, heavy chains, or light chains in the antibody to CD19 or the antigen-binding fragment thereof according to the present disclosure are listed in the sequence listing appended.

The nucleic acid molecule of the present disclosure which encodes the anti-CD19 antibody or the antigen-binding fragment thereof is construed to encompass nucleotide sequences having substantial identity to the nucleic acid molecule. In this context, the term "substantial identity" refers to an identity of at least 80%, more preferably at least 90%, and most preferably at least 95% between the nucleotide sequence of the present disclosure and any other sequences as analyzed by commonly used algorithm when alignment therebetween is made as much correspondingly as possible.

Considering the above-described mutations having biologically equivalent activity, it should be construed that nucleic acid molecules encoding the antibody or the antigen-binding fragment; or the chimeric antigen receptor polypeptide according to the present disclosure also include sequences having substantial identity therewith. In this regard, the substantial identity refers to an identity of at least 61%, more preferably at least 70%, still more preferably 80%, and most preferably at least 90% between the nucleotide sequence of the present disclosure and any other sequences as analyzed by commonly used algorithm when alignment therebetween is made as much correspondingly as possible. Methods of alignment for sequence comparison are known in the art. Various methods and algorithms for alignment are disclosed in Smith and Waterman, *Adv. Appl. Math.* 2:482(1981); Needleman and Wunsch, *J. Mol. Bio.* 48:443(1970); Pearson and Lipman, *Methods in Mol. Biol.* 24: 307-31(1988); Higgins and Sharp, *Gene* 73:237-44 (1988); Higgins and Sharp, *CABIOS* 5:151-3(1989); Corpet et al., *Nuc. Acids Res.* 16:10881-90 (1988); Huang et al., *Comp. Appl. BioSci.* 8:155-65(1992) and Pearson et al., *Meth. Mol. Biol.* 24:307-31(1994). The NCBI Basic Local Alignment Search Tool (BLAST; Altschul, et al., J. Mol. Biol. 215:403-10(1990)) is available from, for example, the NBCI (National Center for Biological Information), and can be used in connection with sequence analysis programs, such as blastp, blasm, blastx, tblastn and tblastx, on the Internet. The use of the program in comparing sequence similarity can be available on the BLAST help page at the NCBI website.

Another aspect of the present disclosure provides a recombinant vector carrying a nucleic acid molecule coding for the anti-CD19 antibody or the antigen-binding fragment thereof.

According to another aspect thereof, the present disclosure provides a host cell transformed with the recombinant vector.

So long as it allows a vector to be cloned thereto and expressed sequentially, any host cell can be used in the present disclosure. Such host cells are well known in the art. For example, eukaryotic host cells suitable for the vector include monkey kidney cells (COS7), NSO cells, SP2/0, Chinese hamster ovary (CHO) cells, W138, baby hamster kidney (BHK) cells, MDCK, myeloma cell lines, HuT 78 cells, and HEK-293 cells, but are not limited thereto.

According to another aspect thereof, the present disclosure provides a CD19-specific chimeric antigen receptor comprising the following:
  (a) an extracellular domain containing the anti-CD19 antibody or the antigen-binding fragment thereof;
  (b) a transmembrane domain; and
  (c) an intracellular signaling domain.

As used herein, the term "chimeric antigen receptor (CAR)" refers to an artificially constructed hybrid protein or polypeptide in which an antigen-binding domain (e.g., single-chain variable fragment (scFv)) of an antibody is linked to a T-cell signaling or T-cell activating domain. Taking advantage of the antigen-binding function of a monoclonal antibody, chimeric antigen receptors give T cells the new ability to target a specific protein in a non-MHC-restricted manner. Non-MHC-restricted antigen recognition provides CAR-expressing T cells with an ability to recognize irrespective of antigen processing, thus avoiding main tumor escape mechanisms. In addition, when expressed in T cells, CAR does advantageously not dimerize with intrinsic T-cell receptor (TCR) alpha and beta chains.

The chimeric antigen receptor of the present disclosure comprises an extracellular domain containing an antibody induced against CD19, known as a B lymphocyte antigen, or against an antigen-binding fragment thereof. In the present disclosure, the antibody induced against CD19 or an antigen-binding fragment thereof is as defined above for the anti-CD19 antibody or the antigen-binding fragment thereof.

According to an embodiment of the present disclosure, the chimeric antigen receptor of the present disclosure is expressed on cell surfaces. Hence, the chimeric antigen receptor may comprise a transmembrane domain. The transmembrane domain may be derived from natural or synthetic sources known in the art. By way of example, the transmembrane domain may be a transmembrane domain of the protein selected from the group consisting of alpha, beta, or zeta chains of T-cell receptor, CD27, CD28, CD3 epsilon, CD45, CD4, CD5, CD8 (CD8a), CD9, CD16, CD22, CD33, CD37, CD64, CD80, CD86, CD134, CD137, and CD154, but is not limited thereto.

According to an exemplary embodiment of the present disclosure, the transmembrane domain is the CD8-derived hinge/transmembrane domain encoded by SEQ ID NO: 20.

The term "intracellular signaling domain", as used herein, refers to a functional protein domain that produces a $2^{nd}$ messenger or functions as an effector in response to the $2^{nd}$ messenger to intracellularly transfer information so as to regulate cellular activity via a defined signaling pathway.

According to another embodiment of the present disclosure, the chimeric antigen receptor of the present disclosure may comprise an intracellular signaling domain. The intracellular signaling domain is responsible for intracellular signaling following the binding of extracellular ligand binding domain to the target (e.g., CD19) resulting in the activation of the immune cell and immune response. In other words, the signal transducing domain is responsible for the activation of at least one of the normal effector functions of the immune cell in which the chimeric antigen receptor is expressed. For example, the effector function of a T cell can be a cytolytic activity or helper activity including the secretion of cytokines. Preferred examples of signal transducing domain for use in a chimeric antigen receptor can be the cytoplasmic sequences of the T cell receptor and co-receptors that act in concert to initiate signal transduction following antigen receptor engagement, as well as any derivate or variant of these sequences and any synthetic sequence that has the same functional capability.

According to an exemplary embodiment, the intracellular signaling domain of the chimeric antigen receptor is a domain derived from CD3ζ (CD3 zeta) chain.

According to a still further exemplary embodiment, the domain derived from the CD3ζ (CD3 zeta) chain is a CD3ζ domain encoded by a nucleotide sequence including SEQ ID NO: 22.

According to another exemplary embodiment of the present disclosure, the intracellular signaling domain of chimeric antigen receptor further comprises at least one costimulatory molecule selected from the group consisting of OX40 (CD134), CD2, CD27, CD28, CDS, ICAM-1, LFA-1 (CD11a/CD18), and 4-1BB (CD137). The intracellular signaling domain may be obtained or derived from an intracellular signaling molecule and may include an entirety or a part of the molecule from which the intracellular signaling domain is derived, as well as the domain described above.

According to an exemplary embodiment of the present disclosure, the costimulatory domain may be a functional signaling domain obtained from a protein selected from the group consisting of CD28, OX40, 4-1BB (CD137), and/or ICOS (CD278) and, more particularly, a functional signaling domain of CD28 and/or OX40.

According to another embodiment of the present disclosure, the intracellular signaling domain is a functional signaling of 4-1 BB, CD28, OX40, CD3 zeta, or a combination thereof. Most particularly, the intracellular signaling domain is a functional signaling domain of CD3 zeta.

According to a more particular embodiment of the present disclosure, the costimulatory molecule including CD137 is a CD3ζ domain encoded by a nucleotide sequence including SEQ ID NO: 21.

The transmembrane domain and intracellular signaling domain in the chimeric antigen receptor of the present disclosure may be at least one combination selected from among the transmembrane domains and intracellular signaling domains described above. For example, the chimeric antigen receptor of the present disclosure may comprise the CD8α transmembrane domain and the intracellular signaling domains of CD28 and CD3ζ.

Structures of CAR constructs according to an embodiment of the present disclosure are depicted in FIG. 9, with the amino acid/nucleotide sequences thereof given in the sequence listing appended.

Another aspect of the present disclosure provides a nucleic acid molecule encoding the chimeric antigen receptor described above.

The above-mentioned anti-CD19 antibody or the antigen-binding fragment (polypeptide) thereof, the nucleic acid molecule coding therefor, the chimeric antigen receptor comprising the anti-CD19 antibody or the antigen-binding fragment thereof, and the nucleic acid molecule coding for the chimeric antigen receptor are each in an isolated state.

As used herein, the term "isolated" means altered or removed from the natural/native state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

According to another aspect thereof, the present disclosure provides a recombinant vector carrying the above-mentioned nucleic acid molecule. For the "vector" to be described hereinafter, the antibody or the antigen-binding fragment thereof, or the nucleic acid molecule encoding a chimeric antigen receptor are commonly applied.

The term "vector" is intended to encompass a transfer vector and an expression vector.

As used herein, the term "transfer vector" refers to a composition of matter which comprises an isolated nucleic acid and which can be used to deliver the isolated nucleic acid into the interior of a cell. Examples of the transfer vector include, but are not limited to, linear polynucleotides, polynucleotides associated with ionic or amphiphilic compounds, plasmids, and viruses. More particularly, the transfer vector includes an autonomously replicating plasmid or virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector", as used herein, refers to a vector comprising a recombinant polynucleotide comprising expression control sequences operatively linked to a nucleotide sequence to be expressed in a host cell. An expression vector comprises sufficient cis-acting elements for expression; other elements for expression can be supplied by the host cell or in an in vitro expression system. Expression vectors include plasmids; cosmids; and viruses, such as bacteriophages, adenoviruses, lentiviruses, retroviruses, and adeno-associated viruses, which all incorporate the recombinant polynucleotide. According to an exemplary embodiment of the present disclosure, a nucleic acid molecule coding for the antibody or antigen-binding fragment, or the chimeric antigen receptor is operatively linked to a promoter in the vector of the present disclosure. As used herein, the term "operatively linked" means a functional linkage between a regulatory sequence for nucleic acid expression (example: a promoter, a signal sequence, or array of positions to which transcriptional factors bind) and other nucleic acid sequences, and by which the regulatory sequences are able to control the transcription and/or translation of the other nucleic acid sequence.

The recombinant vector system of the present disclosure can be constructed using various methods known in the art. With respect to concrete methods, reference may be made to Sambrook et al., Molecular Cloning, A Laboratory Manual, Cold Spring Harbor Laboratory Press (2001), which is incorporated herein by reference.

The vectors of the present disclosure may be constructed as a vector for gene cloning, for protein expression, or for gene transfer. Also, the vectors of the present disclosure may be constructed for eukaryotic or prokaryotic cells.

For example, when the present vector is an expression vector in a eukaryotic cell, promoters derived from genomes of mammalian cells (e.g., a metallothionein promoter, β-actin promoter, human hemoglobin promoter and human muscle creatinine promoter) or promoters derived from mammalian viruses (e.g., an adenovirus late promoter, a vaccinia virus 7.5K promoter, SV40 promoter, cytomegalovirus promoter, a tk promoter of HSV, a promoter of mouse mammary tumor virus (MMTV), a LTR promoter of HIV, a promoter of moloney virus, a promoter of Epstein Barr Virus (EBV), a promoter of Rous Sarcoma Virus (RSV)) may be use. Generally, the vectors include a polyadenylate sequence as a transcriptional termination sequence.

According to an embodiment of the present disclosure, when used as a transfer vector, the vector may be "retroviral vector". Retroviruses provide a convenient platform for gene delivery systems. A selected gene can be inserted into a vector and packaged in retroviral particles. The recombinant virus can then be delivered to cells of the subject either in vivo or in vitro. A number of retroviral systems are known in the art. In some exemplary embodiments, the retroviral vector may be a pMT retroviral vector, which is an MLV-based retroviral vector, but is not limited thereto.

According to an embodiment of the present disclosure, the vector may be a lentivirus vector or an adenovirus vector.

The recombinant vector of the present disclosure may be fused with additional nucleotide sequences to facilitate the isolation and purification of the polypeptide expressed from the vector. The nucleotide sequences to be fused with the present vector include, for example, glutathione S-transferase (Pharmacia, USA), maltose binding protein (NEB, USA), FLAG (IBI, USA) and 6× His (hexahistidine; Qiagen, USA) and the like. The expression vector of the present disclosure may also comprise a selectable marker gene and/or a reporter gene as a selection marker for evaluating the expression of the antibody or the antigen-binding fragment and the CAR polypeptide containing the antibody. The selectable marker gene may be an antibiotic resistant gene typically used in the art, examples of which include genes resistant to ampicillin, gentamicin, carbenicillin, chloramphenicol, streptomycin, kanamycin, geneticin, neomycin, and tetracycline. The reporter gene may be exemplified by luciferase, beta-galactosidase, chloramphenicol acetyl transferase, and green fluorescent protein genes.

Methods of introducing and expressing genes into a cell are known in the art. In the context of an expression vector, the vector can be readily introduced into a host cell, e.g., mammalian, bacterial, yeast, or insect cell by any method known in the art. For example, the expression vector can be transferred into a host cell by physical, chemical, or biological means. The physical means include calcium phosphate precipitation, lipofection, particle bombardment, microinjection, electroporation, and the like. The chemical means include colloidal dispersion systems, such as macromolecule complexes, nanocapsules, microspheres, beads, and lipid-based systems including oil-in-water emulsions, micelles, mixed micelles, and liposomes. Within the biological means are the use of DNA or RNA vectors such as lentivirus, retrovirus, and the like.

According to another aspect thereof, the present disclosure provides a cell expressing the chimeric antigen receptor.

In one embodiment of the present disclosure, the cell refers to a cell of hematopoietic origin functionally involved in the initiation and/or execution of an innate and/or adaptive immune response.

The immune cell according to the present disclosure may be derived from a stem cell. The stem cells may be adult stem cell, non-human embryonic stem cells, cord blood stem cells, bone marrow stem cells, induced pluripotent stem cells, or hematopoietic stem cells. More particularly, the immune cells may be selected from the group consisting of dendritic cells, killer dendritic cells, mast cells, NK-cells, B-cells or inflammatory T-lymphocytes, cytotoxic T-lymphocytes, regulatory T-lymphocytes, and helper T-lymphocytes, but are not limited thereto.

In the present disclosure, the chimeric antigen receptor-expressing cells are called effector cells. The effector cells include a population of autologous or allogeneic cells. In other words, the effector cells include a population of autologous or allogeneic cells expressing CAR specific for CD19.

According to an embodiment of the present disclosure, the effector cells include a population of cells transduced or transfected with a vector carrying a nucleic acid molecular coding for a CD19-specific CAR. The transfection or transduction can be achieved by various means known in the art as described above, without limitations.

Hence, according to an exemplary embodiment of the present disclosure, after being delivered into the effector cells, e.g., T lymphocytes or natural killer cells, the nucleic acid molecule coding for the CD19-specific CAR is transcribed into mRNA from which a CD19-specific CAR polypeptide is then translated, and expressed on the cell surface.

Also, another aspect of the present disclosure provides a pharmaceutical composition comprising a cell expressing the chimeric antigen receptor of the present disclosure.

The pharmaceutical composition may be provided in the form of a pharmaceutical composition comprising a chimeric antigen receptor-expressing cell and a pharmaceutically acceptable carrier.

When administered in the form of a pharmaceutical composition, the cell expressing the chimeric antigen receptor of the present disclosure may be a cell derived from an animal allogenic to the subject, or a cell autologous cell.

The pharmaceutical composition of the present disclosure comprises a population of cells expressing the chimeric antigen receptor of the present disclosure.

The pharmaceutical composition of the present disclosure comprises a cell expressing the chimeric antigen receptor of the present disclosure as an effective ingredient. Accordingly, the common descriptions between them are omitted in order to avoid undue redundancy leading to the complexity of this specification.

As will be proven in the following Example, when the chimeric antigen receptor T cells (CD19_12.18 CAR-T cells) containing the CD19_12.18 antibody fragment of the present disclosure and a CD19 antigen-expressing cell line (RaJi) are co-cultured, the CD19 antigen on the surface of the CD19-positve cell line (RaJi) is recognized to induce the activation of the chimeric antigen receptor. Thus, the pharmaceutical composition of the present disclosure is expected to find advantageous applications in the treatment of CD19 antigen-related diseases.

Diseases that can be prevented or treated by the pharmaceutical composition of the present disclosure are human and mammalian diseases associated with CD19 positive cells, including B cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.

In addition, the diseases include autoimmune diseases and inflammatory diseases associated with inappropriate or enhanced B cell count and/or activation. Examples of the autoimmune diseases and inflammatory diseases include multiple sclerosis, rheumatoid arthritis, and systemic lupus erythematosus (SLE).

The pharmaceutically acceptable carrier contained in the pharmaceutical composition of the present disclosure is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present disclosure may further comprise a lubricant, a wetting agent, a sweetening agent, a flavoring agent, an emulsifier, a suspending agent, a preservative, and the like in addition to the above ingredients. Suitable pharmaceutically acceptable carriers and preparations are described in detail in Remington's Pharmaceutical Sciences ($19^{th}$ ed., 1995).

The pharmaceutical composition of the present disclosure may be administered orally or parenterally, for example, by intravenous injection, subcutaneous injection, intramuscular injection, intraperitoneal injection, intrasternal injection, intratumoral injection, topical administration, intranasal administration, intrapulmonary administration, and rectal administration.

The appropriate dose of the pharmaceutical composition of the present disclosure varies depending on factors, such as a formulating method, a manner of administration, patient's age, body weight, gender, and morbidity, food, a time of administration, a route of administration, an excretion rate, and response sensitivity. An ordinarily skilled practitioner can easily determine and prescribe an effective dose for desired treatment or prevention. According to a preferable embodiment of the present disclosure, the daily dose of the pharmaceutical composition of the present disclosure is 0.0001-100 mg/kg. As used herein, the term "pharmaceutically effective amount" refers to an amount sufficient to prevent or treat the above-described diseases.

As used herein, the term "prevention" refers to a prophylactic or protective treatment of a disease or a disease condition. As used herein, the term "treatment" refers to a reduction, suppression, relief, or eradication of a disease condition.

The pharmaceutical composition of the present disclosure may be formulated into a unit dosage form or may be prepared in a multi-dose container by using a pharmaceutically acceptable carrier and/or excipient according to a method that can be easily implemented by a person having an ordinary skill in the art to which the present disclosure pertains. Here, the formulation may be in the form of a solution in an oily or aqueous medium, a suspension, an emulsion, an extract, a pulvis, a suppository, a powder, a granule, a tablet, or a capsule, and may further contain a dispersant or a stabilizer.

The pharmaceutical composition of the present disclosure may further comprise other pharmaceutically active agents or drugs, for example, chemotherapeutic agents such as asparaginase, busulfane, carboplatin, cisplatin, daunorubicin, doxorubicin, fluorouracil, gemcitabine, hydroxyurea, methotrexate, paclitaxel, rituximab, vinblastine, vincristine, and the like; targeted therapeutic agents such as bevacizumab, olaparib, and the like; or immune checkpoint inhibitors such as nivolumab, pembrolizumab, and the like, in addition to the above-described chimeric antigen receptor-expressing cells, or may be administered in combination therewith.

According to another aspect thereof, the present disclosure provides a method for treatment of a CD19 positive cell-associated disease, an autoimmune disease, or an inflammatory disease, the method comprising a step of administering to a subject in need thereof a composition comprising the antibody against CD19 or the antigen-binding fragment thereof; or a composition comprising an effector cell expressing the CD19-specific chimeric antigen receptor.

The CD19 positive cell-associated disease, the autoimmune disease, or the inflammatory disease, which are target diseases to be treated by the treated method, is as defined above for the target diseases of the pharmaceutical composition.

In an embodiment of the present invention, the subject is a mammalian animal or a human.

Since the method for the prevention or treatment of cancer or inflammatory disease according to the present disclosure employs the above-described antibody or antigen-binding fragment; or the chimeric antigen receptor-expressing effector cell as an effective ingredient, the overlapping descriptions thereof are omitted to avoid excessive complexity of the specification Advantageous Effects The antibody of the present disclosure binds specifically to CD19 that is highly expressed in cancer cells (particularly, blood cancer) and is very poor in CDR sequence homology to conventional CD19 target antibodies. Thus, the antibody of the present disclosure has a characteristic sequence which leads to specifically binding to an epitope different from that for conventional FMC63 antibody fragments. Inducing immune cell activation in response to stimulation with CD19-positive cells, the anti-CD19 antibody or the antigen-binding fragment of the present disclosure can be advantageously used as a CAR-immune cell therapy product.

BRIEF DESCRIPTION OF THE DRAWINGS

FIG. 9 is a view showing configurations of 7 constructs in which the chimeric antigen receptor components hinge region, transmembrane domain, and costimulatory domain were modified to optimize the activity of the developed antibody fragments.

MODE FOR CARRYING OUT THE INVENTION

Figure 1:
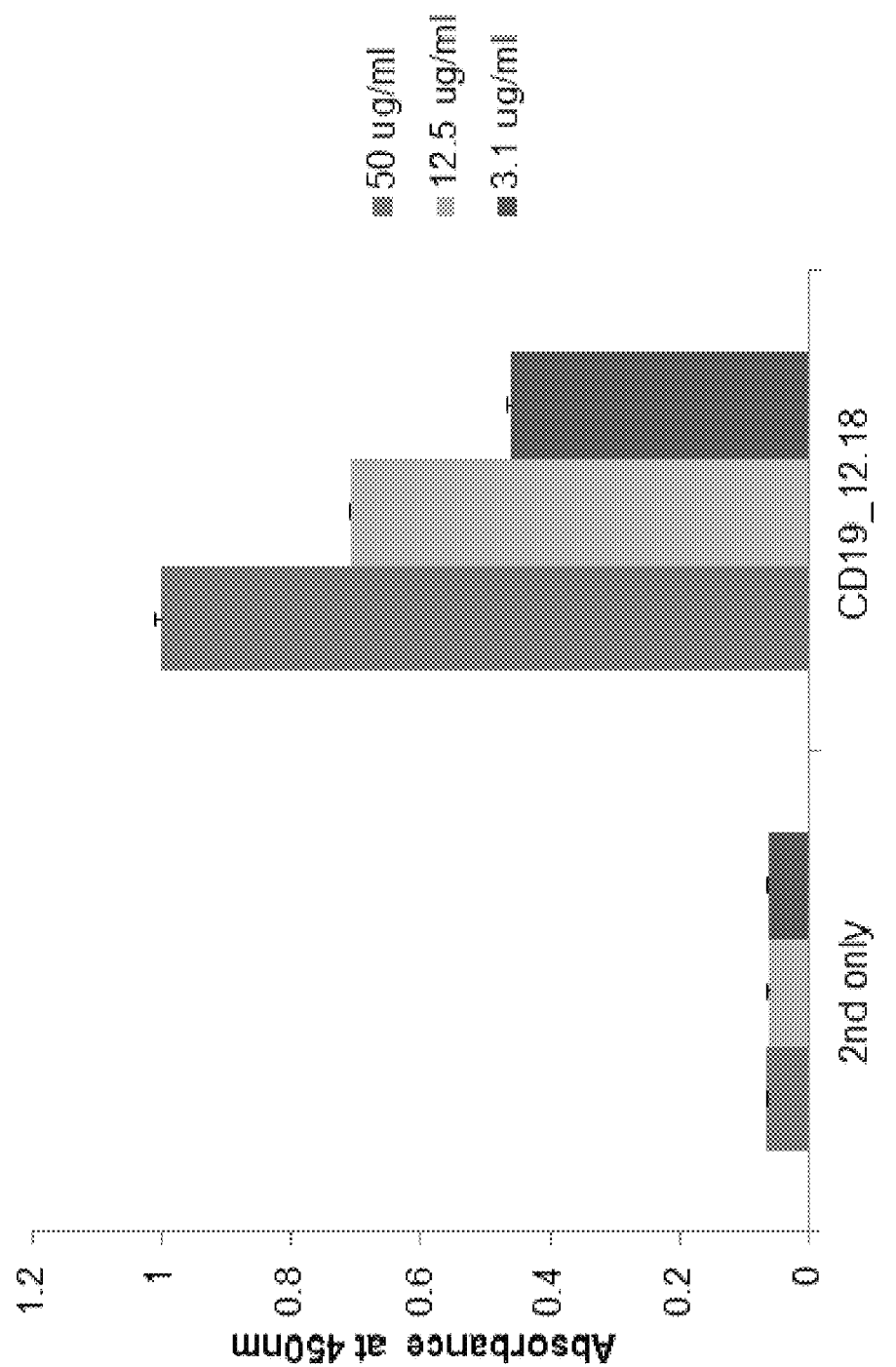
FIG. 1 is a graph illustrating the binding of CD19_12.18 antibody fragment to CD19-ECD protein as analyzed by ELISA.

A better understanding of the present disclosure may be obtained through the following examples which are set forth to illustrate, but are not to be construed as limiting the present disclosure.

EXAMPLES

Example 1

Development of Antibody to CD19

For antibody development, an extracellular domain (ECD) of human CD19 protein was produced using animal cells. A DNA construct in a form where the C-terminal of ECD was conjugated to the hinge and Fc region ($CH_2$—$CH_3$) of human IgG1 (CD19-ECD-Fc) or to His tag (CD19-ECD-His) was cloned into pCEP4 (Invitrogen, Cat. No. V044-50), using the restriction enzymes Hind-III and BamH-I. Subsequently, the transient transfection of the cloned vector into FreeStyle 293F cells (Invitrogen, Cat. No. R790-07) was conducted using polyethyleneimine (Polyscience Inc., Cat. No. 23966), followed by purification from the cell culture with the aid of protein-A Ceramic HyperD F resin (PALL, Cat No. 20078-028) or Ni-NTA Superflow (Qiagen, Cat No. 30410). The purified protein was quantitated using Protein assay dye (Bio-Rad, Cat. No. 500-0006) and subjected to SDS-PAGE, followed by coomassie blue staining to determine concentration and purity. The CD19-ECD-His protein thus obtained was subcutaneously injected to chickens. From the immunized chicken, the spleen and the bursa were excised. Total RNA was extracted from the spleen and the bursa, using TRI reagent (Invitrogen, USA), and used to synthesis cDNA therefrom. A library of antibody fragments was constructed using well-known primers specific for variable regions of immunoglobulin heavy and light chains (see Table 1, Phage display: a laboratory manual, Carlos Barbas III, et al., Cold Spring Harbor Laboratory Press).

TABLE 1

Primer Used for Construction of Antibody Fragment Library

| Primer | Sense | Antisense |
| --- | --- | --- |
| Primer for heavy chain variable region | 5'GGTCAGTCCT CTAGATCTTCCG GCGGTGGTGGCA GCTCCGGTGGTG GCGGTTCCGCCG TGACGTTGGACG AG 3' (SEQ ID NO: 24) | 5'CTGGCCGGCC TGGCCACTAGTG GAGGAGACGATG ACTTCGGTCC 3' (SEQ ID NO: 25) |
| Primer for light chain variable region | 5'GTGGCCCAGG CGGCCCTGACTC AGCCGTCCTCGG TGTC 3' (SEQ ID NO: 26) | 5'GGAAGATCTA GAGGACTGACCT AGGACGGTCAGG 3' (SEQ ID NO: 27) |
| Overlapping PCR primer | 5'GAGGAGGAGG AGGAGGAGGTGG CCCAGGCGGCCC TGACTCAG 3' (SEQ ID NO: 28) | 5'GAGGAGGAGG AGGAGGAGGAGC TGGCCGGCCTGG CCACTAGTGGAG G 3' (SEQ ID NO: 29) |

The chicken immune library thus constructed was subjected to phage bio-panning, with the CD19-ECD-Fc serving as an antigen. For use in bio-panning, the antibody library was obtained in a phage library form using VCSM13 helper phages. Up to four panning rounds were performed. For a panning strategy of enriching phages of high affinity, a lower amount of the antigen was used and a larger number of washing was conducted in a higher number of panning. The number of phages captured by the target antigen was tittered using ER2537 E. coli (New England Biolabs, Cat. No. 801-N) as follows. Binder phages obtained in each bio-panning round were eluted with glycine buffer at pH 2.2. The ER2537 E. coli was cultured overnight in SB (super broth) medium and then diluted by 1/200 in fresh SB medium before passage. Subsequently, an additional incubation for 3 hours at 37° C. reached a log phage. In a 1.5-ml tube, 100 μl of fresh ER2537 E. coli and 10 μl of diluted phages were mixed and incubated for 30 min before being spread on ampicillin-containing LB (lysogeny broth) agar plates. After incubation overnight at 37° C., the number of phages was measured by applying the number of colonies thus formed and the dilution factor.

The binder phages obtained in each bio-panning round 2 were infected into ER2537 E. coli. While the bacteria were maintained in the colony form, ELISA was performed to examine binding to the antigen. To this end, first, the colonies obtained following phage infection were inoculated into SB medium and cultured until the OD$_{600}$ reached 0.5. Subsequently, the cell culture was incubated at 30° C. in the presence of 0.5 mM IPTG while shaking so as to overexpress the antibody fragment proteins. Antibodies binding specifically to CD19 were selected by ELISA using CD19-ECD-Fc protein and by flow cytometry using Raji cells, which overexpress CD19. Through these methods, selection was made of CD19_12.18 that exhibited the highest binding affinity for human CD19. Amino acid sequences of the variable regions in the selected CD19_12.18 antibody are given in Table 2, below.

TABLE 2

Amino Acid Sequence of CDR (Complementarity Determining Region) in CD19_12.18 Antibody

| classification | light chain | heavy chain |
| --- | --- | --- |
| CDR1 | SGGYSSYYG (SEQ ID NO: 4) | SYDMG (SEQ ID NO: 1) |
| CDR2 | ESNKRPS (SEQ ID NO: 5) | GIDDDGRYTSYGSAVDG (SEQ ID NO: 2) |
| CDR3 | GGWDSTHAGI (SEQ ID NO: 6) | GNAGWIDA (SEQ ID NO: 3) |

In order to quantitatively analyze the affinity of the selected CD19_12.18 antibody, antibody fragments including the variable regions were produced using animal cells. A DNA construct in a form where the C-terminal of ECD was conjugated to the hinge and Fc region (CH$_2$—CH$_3$) of human IgG1 (CD19-ECD-Fc) or to His tag (CD19-ECD-His) was cloned into pCEP4 (Invitrogen, Cat. No. V044-50). Subsequently, the cloned vector was transiently transfected into FreeStyle™ 293F cells (Invitrogen, Cat. No. R790-07). From the cell culture, the antibody in the Fc fusion protein form (Anti-CD19 scFv-Fc) was obtained. ELISA was conducted using CD19-ECD kappa light chain fusion protein (CD19-ECD-Ck) as a coating antigen so as to measure the binding affinity of the selected antibody. The purified antibody fragment (Anti-CD19 scFv-Fc) was applied at various concentrations (50, 12.5, and 3.1 μg/mL) to CD19-ECD protein-coated plates. Following incubation with a secondary antibody (anti-human Fc HRP), color was developed with TMB. OD$_{450}$ values were read on an ELISA reader (Victor X3 PerkinElmer) (FIG. 1). As shown in FIG. 1, CD19_12.18 antibody of the present disclosure was identified to bind specifically to CD19-ECD protein.

Figure 2:
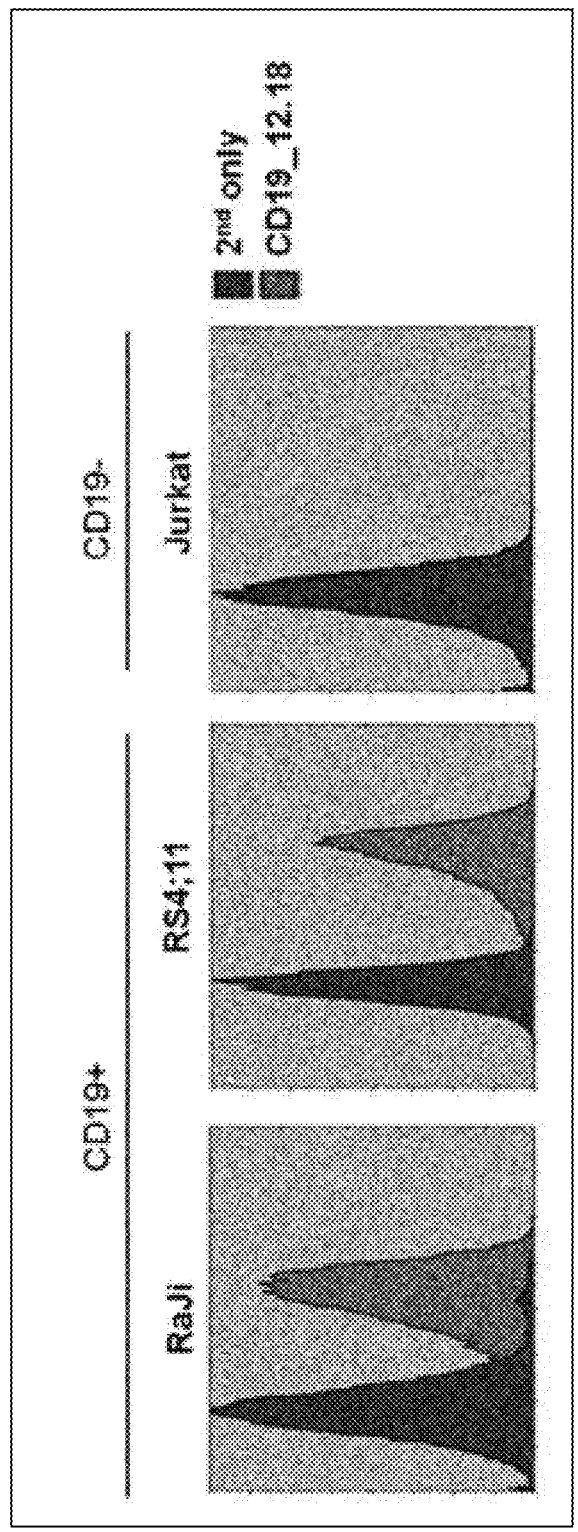
FIG. 2 shows histograms of binding affinity of CD19_12.18 antibody fragment for CD19-positve RaJi, RS4; 11 cells and CD19-negative Jurkat cells as measured by flow cytometry.

In addition, CD19_12.18, which binds to CD19-ECD protein was examined for affinity for the CD19 positive cell lines RaJi and RS4; 11 and the CD19 negative cell line Jurkat. The CD19 positive cell lines RaJi and RS4; 11 and the CD19 negative cell line Jurkat were treated with the purified antibody fragment (Anti-CD19 scFv-Fc). The antibody fragments bound to the cell lines were stained with anti-human IgG-FITC. Antibody fragments bound to the cell lines were measured by flow cytometry (FIG. 2). As can be seen in FIG. 2, CD19_12.18 antibody of the present disclosure was identified to be an antibody binding specifically to CD19 positive cells.

Example 2

Comparison of Epitopes between Developed Antibody Fragment and FMC63

Figure 3:
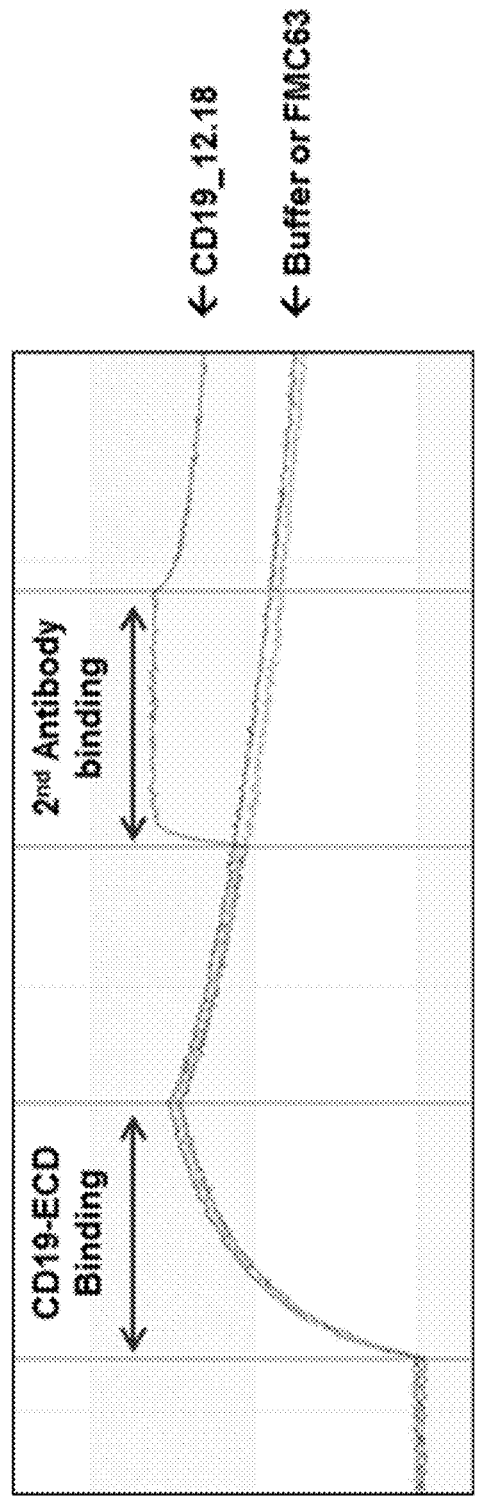
FIG. 3 is a view illustrating comparison of epitopes between the developed antibody fragment and the FMC63 antibody fragment. For epitope comparison with FMC63, FMC63 and CD19-ECD proteins are immobilized to a sensor chip to which the CD19_12.18 antibody fragment of the present disclosure is then applied.

In order to examine whether the developed antibody has an epitope in common with FMC63, which is a mouse-derived CD19 antibody used in a chimeric antigen receptor (CAR) for treatment of B cell malignancy blood cancer, epitope binning was conducted using Octet system (Pall ForteBio). FMC63-Fc was fixed at a concentration of 10 μg/mL to AR2G sensor chip (Fortebio, Cat. No. 18-5092 (tray), 18-5093(pack), 18-5094(case)) by an amine coupling method using EDC/NHS. The CD19-ECD kappa light chain fusion (CD19-ECD-Ck) was conjugated at a concentration of 10 μg/mL for 10 min to the FMC63-fixed sensor chip, followed by stabilizing the linkage between FMC63 and CD19-ECD for 5 min. Thereafter, CD19_12.18 antibody of the present disclosure or FMC63 was conjugated at a concentration of 10 μg/mL for 10 min, after which the linkage between the antigen and the antibody was stabilized for 10 min. Following fixation of FMC63, all the antibodies/antigen were diluted using kinetics buffer (Fortebio, cat No. 18-1092). The same buffer was also used for the stabilization step. In the case where the secondarily bound antibody further binds to the FMC63-bound CD19-ECD protein, the antibody can be construed to have no epitopes in common with FMC63. As shown in FIG. 3, FMC63 did not further bind whereas the CD19_12.18 antibody developed by the present inventors was observed to further bind to the FMC63-bound CD19-ECD. Therefore, CD19_12.18 antibody of the present disclosure is different from FMC63 antibody in terms of epitope.

Example 3

Identification of Epitope for the Developed Antibody

In order to identify epitopes therefor, the developed antibody was analyzed for binding to various mutant CD19 proteins constructed, using flow cytometry. In brief, first, the expression of CD19 protein was identified. To this end, the GFP protein-coexpressing bi-cistronic expression system (mutant CD19-T2A-GFP) using T2A system was digested with ClaI/XhoI and ligated to the pLenti6-V5/DEST lentiviral vector (Invitrogen, USA). The constructs thus obtained were analyzed by base sequencing. An examination was made of the binding of the antibody to the CD19 by flow cytometry for the 293 cell line which had undergone transient transfection to express the full-length CD19 protein and then treated with the purified antibody fragment (Anti-CD19 scFv-Fc).

Figure 4:
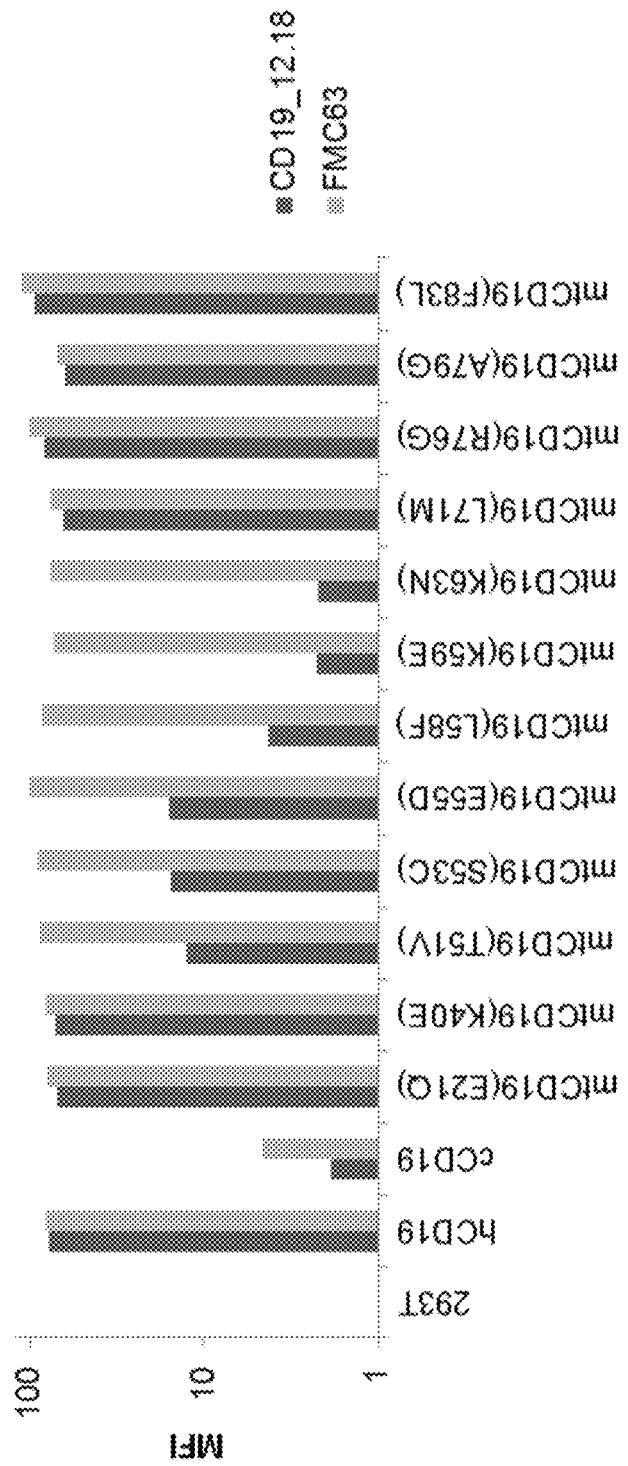
FIG. 4 is a bar graph showing the identification of an epitope for the developed antibody fragments as measured by flow cytometry. The developed antibody fragments were applied to 293 cells in which mutant CD19 had been expressed through transient transfection, with FMC64 antibody serving as a control.
Figure 5:
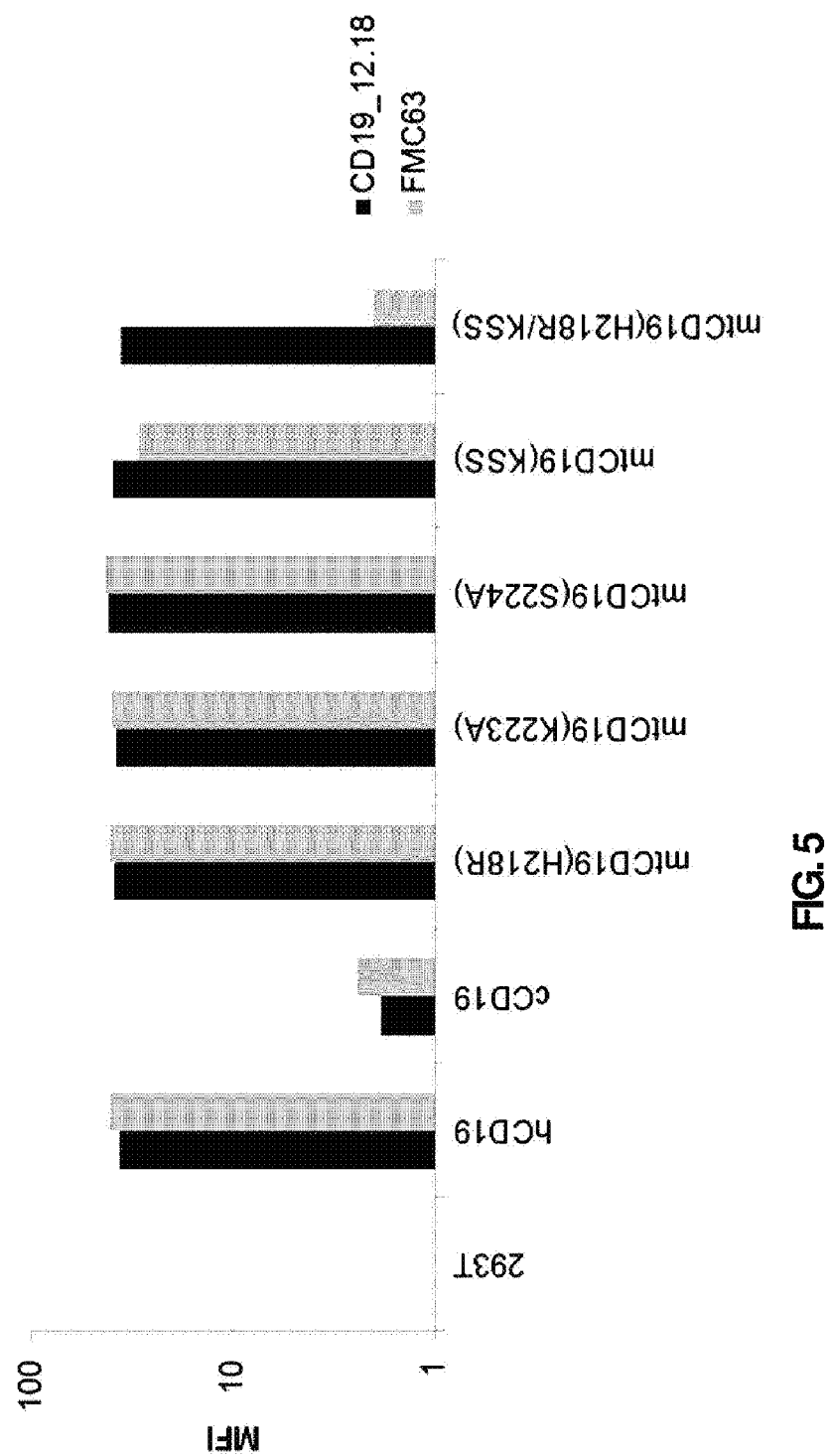
FIG. 5 is a bar graph identifying the binding of FMC63 and the developed antibody fragments to the epitope reported for FMC63. Epitope identification was conducted with 293 cells in which mutant CD19 had been expressed through transient transfection.
Figure 6:
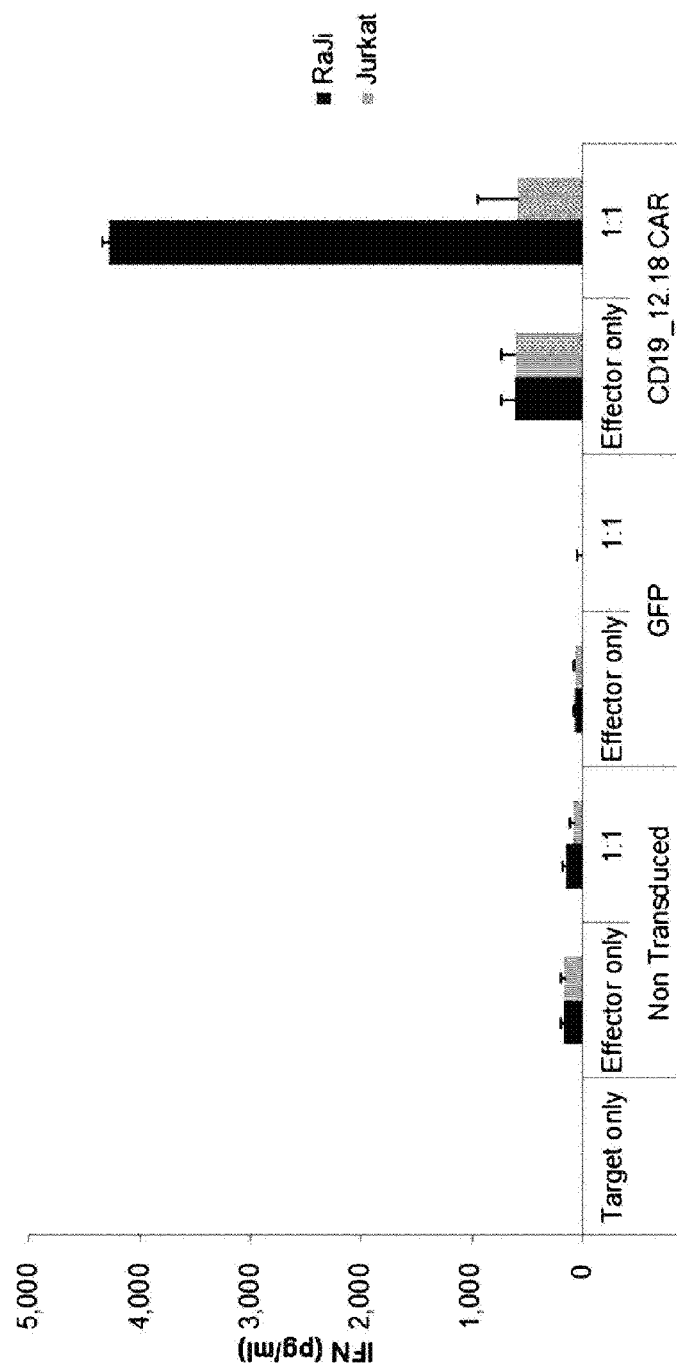
FIG. 6 is a bar graph showing activity of cytotoxic T cells expressing the chimeric antigen receptors conjugated with the antibody fragments of the present disclosure, as measured for secretion levels of interferon gamma.

To begin with, the developed antibody was measured for binding affinity for recombinant human CD19 (hCD19, UniProtKB: P15391, SEQ ID NO: 92) and cynomolgus monkey CD19 (cCD19, UniprotKB: G7Q0T7, SEQ ID NO: 93). Like FMC63, the developed antibody was observed to have no cross-reactivity with cCD19 cross-reactivity (FIG. 4). For use in investigating epitopes for the developed antibody, mutant CD19 (mtCD19) proteins were made by substituting amino acids at specific positions with corresponding amino acids in cynomolgus monkey CD19. With respect to 12 amino acid residues different between hCD19 and cCD19 in sites other than already reported epitope sites for FMC63, mutant CD19 proteins having the amino acid residues of cCD19 were developed, followed by analyzing binding affinity therefor. Binding to GFP-positive cells was analyzed on the basis of mean fluorescence intensity (MFI). Of the 12 mutants tested, six residues (T51V, S53C, E55D, L58F, K59E, and K63N) were observed to play an important role in binding between the developed antibody CD19_12.18 and hCD19. Inter alia, the three mutants (L58F, K59E, and K63N) were found to completely suppress the binding of CD19_12.18 to the CD19, revealing the residues as key residues essential for the epitope to which the developed antibody binds (FIG. 4). In contrast, FMC63 was observed to bind intactly to the six mutant hCD19 proteins, indicating that the mutations do not influence the overall structure of hCD19, but alter the epitopic sites to which CD19_12.18 bind.

In addition, examination was made to see whether the antibody CD19_12.18 could bind to a mutant in which a site important for the binding of FMC63 thereto was mutated. In this regard, five mutants which had mutations made at sites important for the binding of FMC63 thereto were constructed (Sommermeyer D et al., Leukemia, 2017, 31(10): 2191). As was consistent with the result of the reference document, it was observed that FMC63 exhibited altered binding affinity for only the mutant (H218R/KSS) in which the residue at position 218 was substituted with arginine and serine was inserted at position 224. In contrast, the developed antibody CD19_12.18 was observed to normally bind to the mutant, indicating that the antibody is different in epitope from FMC63 (FIG. 5).

Example 4

Preparation of Lentivirus Including Developed Antibody Fragment-Conjugated Chimeric Antigen Receptor A chimeric antigen receptor was developed on the basis of the developed antibody CD19_12.18. For the chimeric antigen receptor, codon optimization was made of a CD8 leader, scFv-type CD19_12.18, a hinge and transmembrane domain of CD8, a cytoplasmic domain of CD137, and a cytoplasmic domain of CD3 zeta and the sequence thus optimized was digested with SpeI/XhoI before insertion into pLenti6-V5/DEST lentiviral vector (Invitrogen, USA). The construct thus obtained (SEQ ID NO: 23) was identified by base sequencing.

The prepared lentiviral construct was transduced, together with the plasmid pCMV-dR8.91 carrying viral coat protein VSV-G (vesicular stomatitis indiana virus G protein), gag, pol, and rev genes, into Lenti-X 293T cells (Takara Bio Inc., Japan). Transduction was performed using Lipofectamine 2000 (Invitrogen, USA) according to the manufacturer's protocol. Seventy-two hours after transduction, a lentivirus containing culture medium was enriched by 10 fold through a centrifugal filter (Millipore, USA).

Example 5

Preparation of T Cell Displaying Developed Antibody Fragment-Bearing Chimeric Antigen Receptor Cytotoxic T cells on which CD19_12.18 antibody fragment (scFv)-bearing chimeric antigen receptors were displayed were prepared using the lentivirus obtained in Example 3.

First, human naive T cells were isolated and stimulated with Dynabeads™ Human T-Activator CD3/CD28 (Thermofisher scientific, USA) for 24 hours. Thereafter, the lentivius was infected for 24 hours into the cells in the presence of polybrene (Sigma-Aldrich, USA). Then, the medium was exchanged with a medium containing IL-2 (Gibco, USA), followed by incubation at 37° C. in a 5% $CO_2$ atmosphere.

The T cells presenting the CD19_12.18-bearing chimeric antigen receptor on the surface thereof (CD19_12.18 CAR-T cells) were used in experiments within 24 hours after being prepared.

Example 6

Activity of Cytotoxic T Cell Presenting Developed Antibody Fragment-Bearing Chimeric Antigen Receptor on Surface Thereof The cytotoxic T cells presenting on the surface thereof the chimeric antigen receptor prepared in Example 4 (CD19_12.18 CAR-T cells) were used to examine whether the activation of the chimeric antigen receptor T cells is induced with the recognition of CD19 on cell surfaces.

Briefly, the CD19-positive cell line RaJi and the CD19-negative cell line Jurkat E6.1 were separately cultured in RPMI-1640 supplemented with 10% fetal bovine serum and 1% penicillin-streptomycin. First, the CD19-positive or negative cells were seeded at a density of $3\times10^4$ cells/well into round-bottom 96-well plates. After removal of the culture supernatant, the prepared chimeric antigen receptor T cells (CD19_12.18 CAR-T cells) were added at a predetermined rate per well and incubated at 37° C. for 24 hours in a 5% $CO_2$ atmosphere. Interferon gamma secreted to the medium was quantitated using an ELISA kit according to the manufacturer's protocol. The results are shown in FIG. 6. In this regard, a group in which chimeric antigen receptor T cells were added to plates containing target cells (Effector T cell only) and a group in which no chimeric antigen receptor T cells were added to plates containing target cells (Target cell only) were used as controls.

As can be seen in FIG. 6, significant increases in the secretion of interferon gamma were detected in the CD19_12.18 antibody fragment-bearing chimeric antigen receptor T cells of the present disclosure (CD19_12.18 CAR-T cells) and the CD19-positive cells (RaJi). Therefore, when recognizing CD19 on the CD19-positive cells (RaJi), the cytotoxic T cells (CD19_12.18 CAR-T cells) presenting the CD19_12.18 antibody fragment-bearing chimeric antigen receptor of the present disclosure on the surface thereof were induced to be activated.

Example 7

Improvement of Affinity of Developed Antibody Fragment and Development of Humanized Antibody In order to acquire antibody fragments superior to CD19_12.18 in terms of binding affinity for CD19, heavy chain and light chain libraries were combined to produce new sub libraries. To this end, oligonucleotides having NNK degenerate codons were employed, with 70% or more of the sequence of CD19_12.18 maintained. A nucleic acid sequence coding for the CD19_12.18 antibody fragment was used as a template DNA. Random codons were incorporated into six CDRs by PCR. The antibody fragment amplicons were purified using QIAquick Gel Extraction Kit (QIAGEN, USA). The antibody fragment amplicons were ligated to pComb3XSS vector after both were digested with sfi I. The resulting recombinant vector was transduced into ER2537 to construct phage libraries. Antibodies were selected using the phage libraries in the same manner as in Example 1.

From the selected antibodies, humanized antibodies were developed by CDR grafting. For the human antibody to which the CDR of the developed antibody would be implanted, human germline V and J genes similar to each other in view of base sequence were selected using IMGT/V-QUEST (Brochet, X. et al., Nucl Acids Res. 36:503-508 (2008)). The developed humanized antibodies were produced in Fc tag forms, using FreeStyle™ 293F cells. IGHV3-74*01 and IGHJ5*01 were employed as V and J genes of the heavy chain, respectively. IGLV1-51*02 and IGLJ2*01 were employed as V and J genes of the light chain, respectively. Amino acid sequences of variable regions in heavy and light chains of the developed antibodies are given in Tables 3 and 4.

TABLE 3

Amino Acid Sequence of Heavy Chain CDR Region of Antibody with Improved Affinity

| Antibody | $1^{st}$ Heavy chain | $2^{nd}$ Heavy chain | $3^{Rd}$ Heavy chain |
| --- | --- | --- | --- |
| hzCD19_1218.81 | SYDMG (SEQ ID NO: 1) | GIDDDGRYTSYGSAVDG (SEQ ID NO: 2) | GNAGWIDA (SEQ ID NO: 3) |
| hzCD19_1218.82 | SYDMG (SEQ ID NO: 1) | GIDDDGRYTSYGSAVDG (SEQ ID NO: 2) | GNAGWIDA (SEQ ID NO: 3) |
| hzCD19_1218.81.12 | SYDMG (SEQ ID NO: 1) | GIDDDGRYTSYGSAVDG (SEQ ID NO: 2) | GNAGWIST (SEQ ID NO: 30) |
| hzCD19_1218.81.17 | SYDMG (SEQ ID NO: 1) | GIDDDGRYTSYGSAVDG (SEQ ID NO: 2) | GNAGWIET (SEQ ID NO: 31) |
| hzCD19_1218.81.52 | SYDMG (SEQ ID NO: 1) | GIDDDGRYTSYGSAVDG (SEQ ID NO: 2) | GNAGWILT (SEQ ID NO: 32) |
| hzCD19_1218.81.55 | SYDMG (SEQ ID NO: 1) | GIDDDGRYTSYGSAVDG (SEQ ID NO: 2) | GNAGWIQN (SEQ ID NO: 33) |
| hzCD19_1218.81.64 | SYDMG (SEQ ID NO: 1) | GIDDDGRYTSYGSAVDG (SEQ ID NO: 2) | GNAGWIQT (SEQ ID NO: 34) |
| hzCD19_1218.81.79 | SYDMG (SEQ ID NO: 1) | GIDDDGRYTSYGSAVDG (SEQ ID NO: 2) | GNAGWIDH (SEQ ID NO: 35) |

TABLE 4

Amino Acid Sequence of Light Chain CDR Region of Antibody with Improved Affinity

| Antibody | $1^{st}$ Light chain | $2^{nd}$ Light chain | $3^{rd}$ Light chain |
| --- | --- | --- | --- |
| hzCD19_1218.81 | SGGYSSYYG (SEQ ID NO: 4) | ESNKRPS (SEQ ID NO: 5) | GGLTPTHAGI (SEQ ID NO: 40) |
| hzCD19_1218.82 | SGGYSSYYG (SEQ ID NO: 4) | ESNKRPS (SEQ ID NO: 5) | GQSTRTHAGI (SEQ ID NO: 41) |
| hzCD19_1218.81.12 | SGGYSSYYG (SEQ ID NO: 4) | ESDKRPA (SEQ ID NO: 36) | GGLTPTHAGI (SEQ ID NO: 40) |
| hzCD19_1218.81.17 | SGGYSSYYG (SEQ ID NO: 4) | ESNKRPS (SEQ ID NO: 5) | GGLTPTHAGI (SEQ ID NO: 40) |

TABLE 4-continued

Amino Acid Sequence of Light Chain CDR Region of Antibody with Improved Affinity

| Antibody | 1st Light chain | 2nd Light chain | 3rd Light chain |
|---|---|---|---|
| hzCD19_1218.81.52 | SGGYSSYYG (SEQ ID NO: 4) | ETDKRPQ (SEQ ID NO: 37) | GGLTPTHAGI (SEQ ID NO: 40) |
| hzCD19_1218.81.55 | SGGYSSYYG (SEQ ID NO: 4) | ESGKRPA (SEQ ID NO: 38) | GGLTPTHAGI (SEQ ID NO: 40) |
| hzCD19_1218.81.64 | SGGYSSYYG (SEQ ID NO: 4) | ESQKRPL (SEQ ID NO: 39) | GGLTPTHAGI (SEQ ID NO: 40) |
| hzCD19_1218.81.79 | SGGYSSYYG (SEQ ID NO: 4) | ESNKRPS (SEQ ID NO: 5) | GGLTPTHAGI (SEQ ID NO: 40) |

Figure 7:
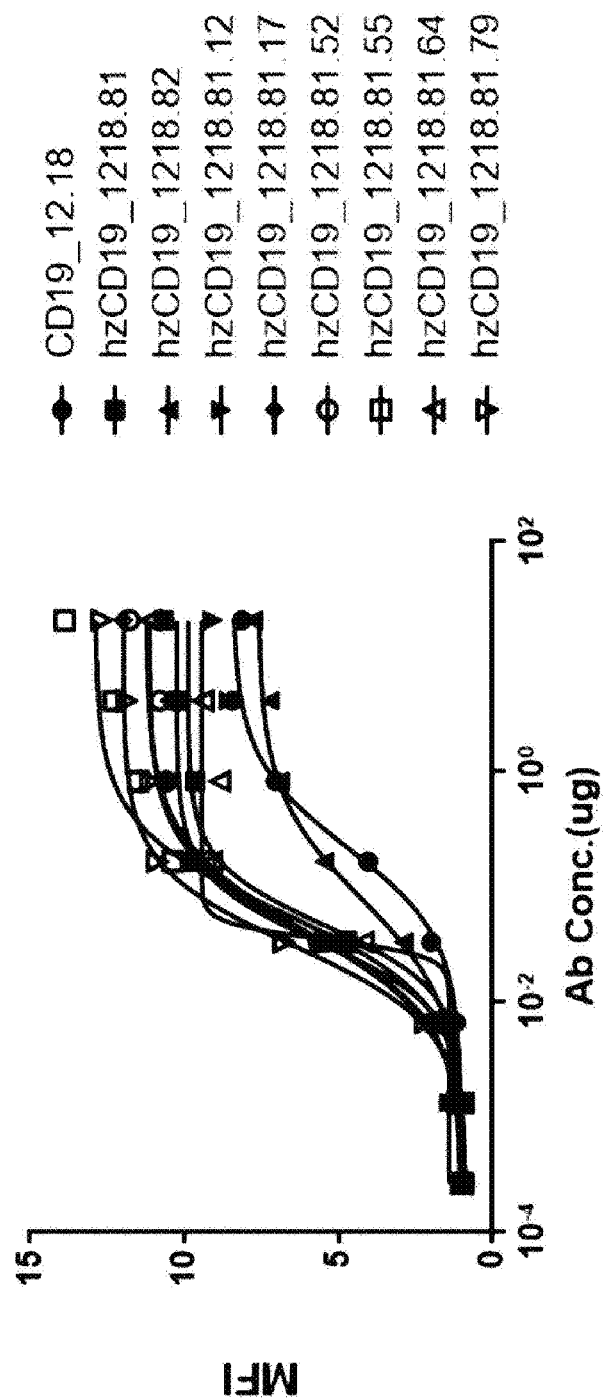
FIG. 7 is a plot showing cell binding potentials of antibody fragments developed through affinity improvement and humanization. CD19-positive RaJi cells were used for the analysis [unit: MFI (mean fluorescence intensity)].

Following affinity improvement and humanization, the selected antibodies were assayed for binding affinity for the CD19-positive cell line RaJi. The CD19-positve cell line RaJi was incubated with various concentrations of purified antibody fragments, followed by staining with anti-human IgG-FITC. The antibody-bound RaJi cells were counted by flow cytometry (FIG. 7) and binding affinity was assayed by Graphpad Prism (Table 5). Through the assay, antibodies having higher binding potential than CD19_12.18 were secured.

TABLE 5

Binding Potential of Affinity-Improved Antibody to RaJi Cell (EC$_{50}$)

| Antibody | EC$_{50}$ (μg) |
|---|---|
| CD19_12.18 | 0.213 |
| hzCD19_1218.81 | 0.032 |
| hzCD19_1218.82 | 0.078 |
| hzCD19_1218.81.12 | 0.034 |
| hzCD19_1218.81.17 | 0.038 |
| hzCD19_1218.81.52 | 0.038 |
| hzCD19_1218.81.55 | 0.059 |
| hzCD19_1218.81.64 | 0.033 |
| hzCD19_1218.81.79 | 0.030 |

Example 8

Preparation of Lentivirus Comprising Chimeric Antigen Receptor Conjugated with Affinity-Improved and Humanized Antibody Fragment Of the developed antibodies, three variants (hzCD19_1218.81, hzCD19_1218.82, and hzCD19_1218.81.79) different in affinity were used to develop chimeric antigen receptors. For a chimeric antigen receptor, codon optimization was made of a CD8 leader, an scFv-type antibody, a hinge and transmembrane domain of CD8, a cytoplasmic domain of CD137, and a cytoplasmic domain of CD3 zeta by using GeneOptimizer (Invitrogen) algorithm. The optimized sequences were digested with SpeI/PacI and ligated to pLenti6.3/V5-TOPO lentiviral vector (Invitrogen, USA) in which the promotor had been modified into EF-1 alpha. The constructs thus obtained were identified by base sequencing.

Each of the prepared lentiviral constructs was transduced, together with the plasmid pCMV-dR8.91 carrying viral coat protein VSV-G (vesicular stomatitis indiana virus G protein), gag, pol, and rev genes, into Lenti-X 293T cells (Takara Bio Inc., Japan). Transduction was performed using Lipofectamine 2000 (Invitrogen, USA) according to the manufacturer's protocol. The cell culture containing lentivirus were enriched with Lenti-X concentrator (Takara Bio Inc., Japan) and stored.

Example 9

Preparation and Activity of Cytotoxic T Cell Presenting on Surface thereof Chimeric Antigen Receptor Conjugated with Affinity-Improved and Humanized Antibody Fragment Cytotoxic T cells presenting the CD19_12.18 antibody fragment (scFv)-bearing chimeric antigen receptor on the surface thereof were prepared using the lentivirus obtained in Example 8 in the same manner as in Example 5. The cytotoxic T cells presenting the chimeric antigen receptor on the surface thereof were used to examine whether the activation of the chimeric antigen receptor T cells is induced with the recognition of CD19 on cell surfaces.

Briefly, GFP-luciferase-expressing lentivirus was transduced into CD19-positive RaJi cells to construct RaJi-Luc cells which were then used in experiments. First, RaJi-Luc cells were seeded at a density of $3 \times 10^4$ cells/well into round-bottom 96-well plates. To the RaJi-Luc cells (T)-seeded plates, the prepared cytotoxic T cells (E) were added at a predetermined treatment rate per well (T:E=1:2, 1:5, or 1:10), followed by incubation at 37° C. for 24 hours in a 5% $CO_2$ atmosphere. Thereafter, interferon gamma secreted to the medium was quantitated using an ELISA kit according to the manufacturer's protocol. Toxicity of cytotoxic T cells was identified through luciferase measurement (Bio-Glo Luciferase assay system, Promega, USA).

Figure 8A:
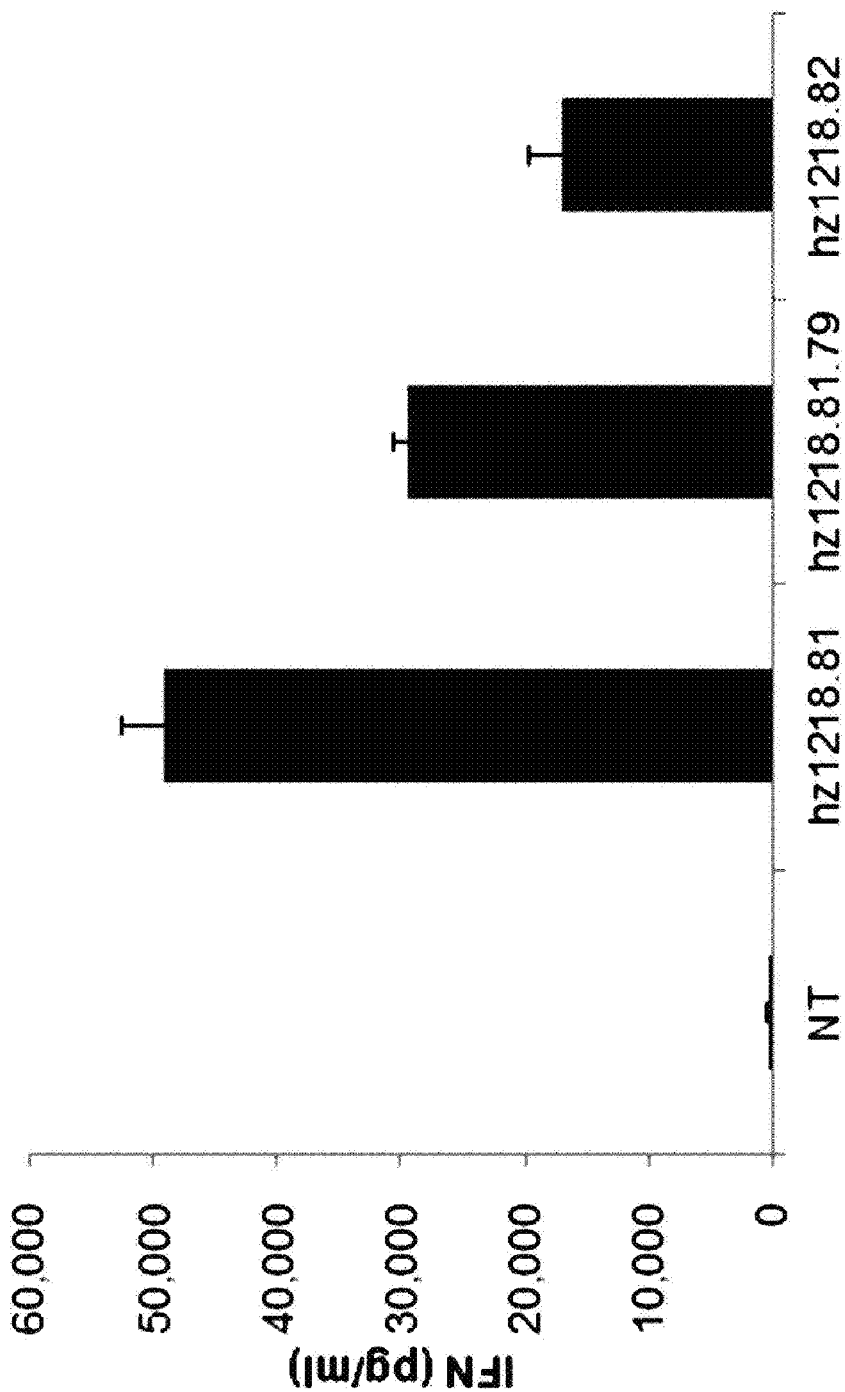
FIG. 8a is a bar graph showing activity of cytotoxic T cells expressing the chimeric antigen receptors conjugated with the antibody fragments of the present disclosure, as measured for secretion levels of interferon gamma. CD19-positive RaJi-Luc cells and cytotoxic T cells were co-cultured at a ratio of 1:5, followed by measuring levels of interferon gamma in the cell cultures.
Figure 8B:
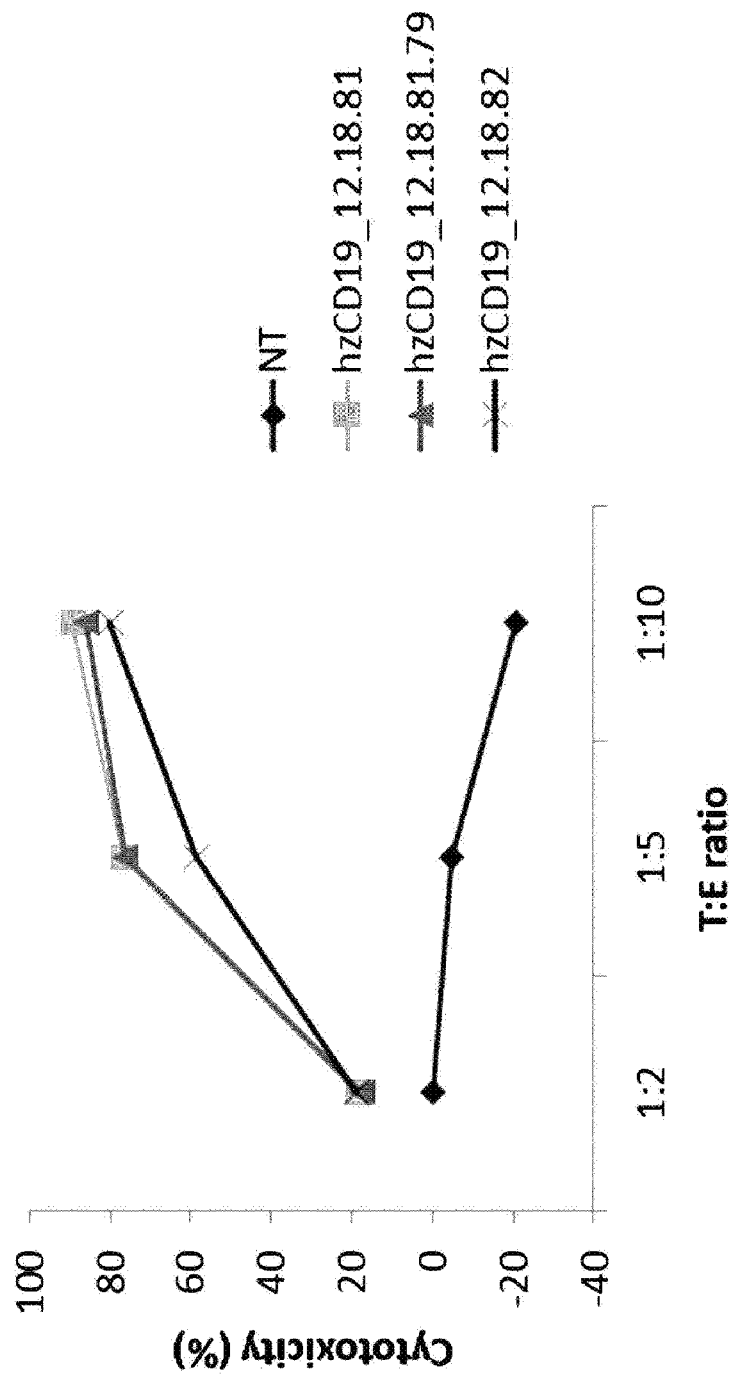
FIG. 8b shows cytotoxicity of cytotoxic T cells as measured for luciferase activity of RaJi-Luc cells surviving after co-culture with RaJi-Luc cells and cytotoxic T cells were co-cultured.
Figure 10A:
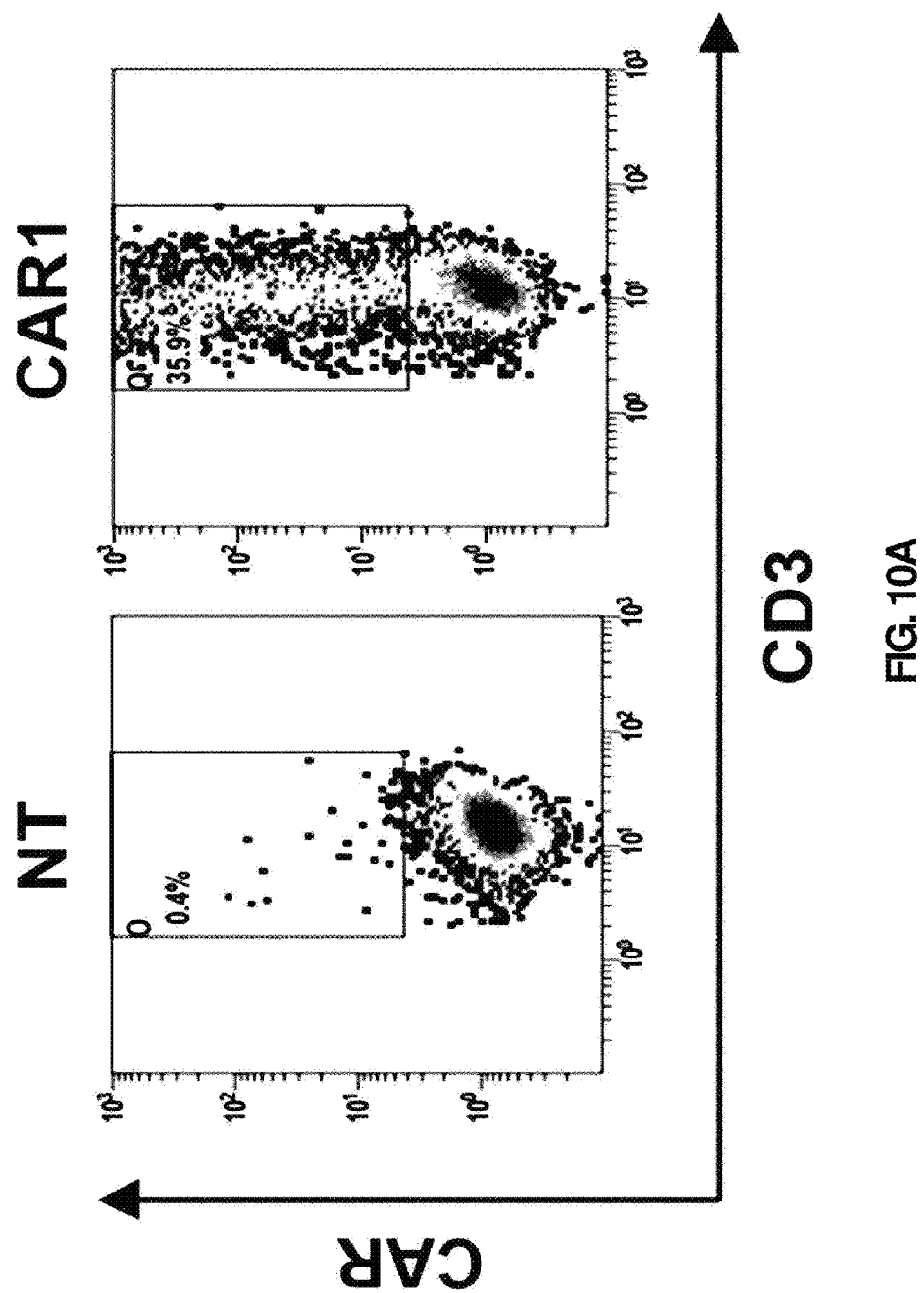
FIGS. 10A, 10B, 10C and 10D showing expression of the 7 modified chimeric antigen receptors as analyzed by flow cytometry. CD3 was used as a marker for analyzing the expression of the 7 modified chimeric antigen receptors in cytotoxic T cells.
Figure 10B:
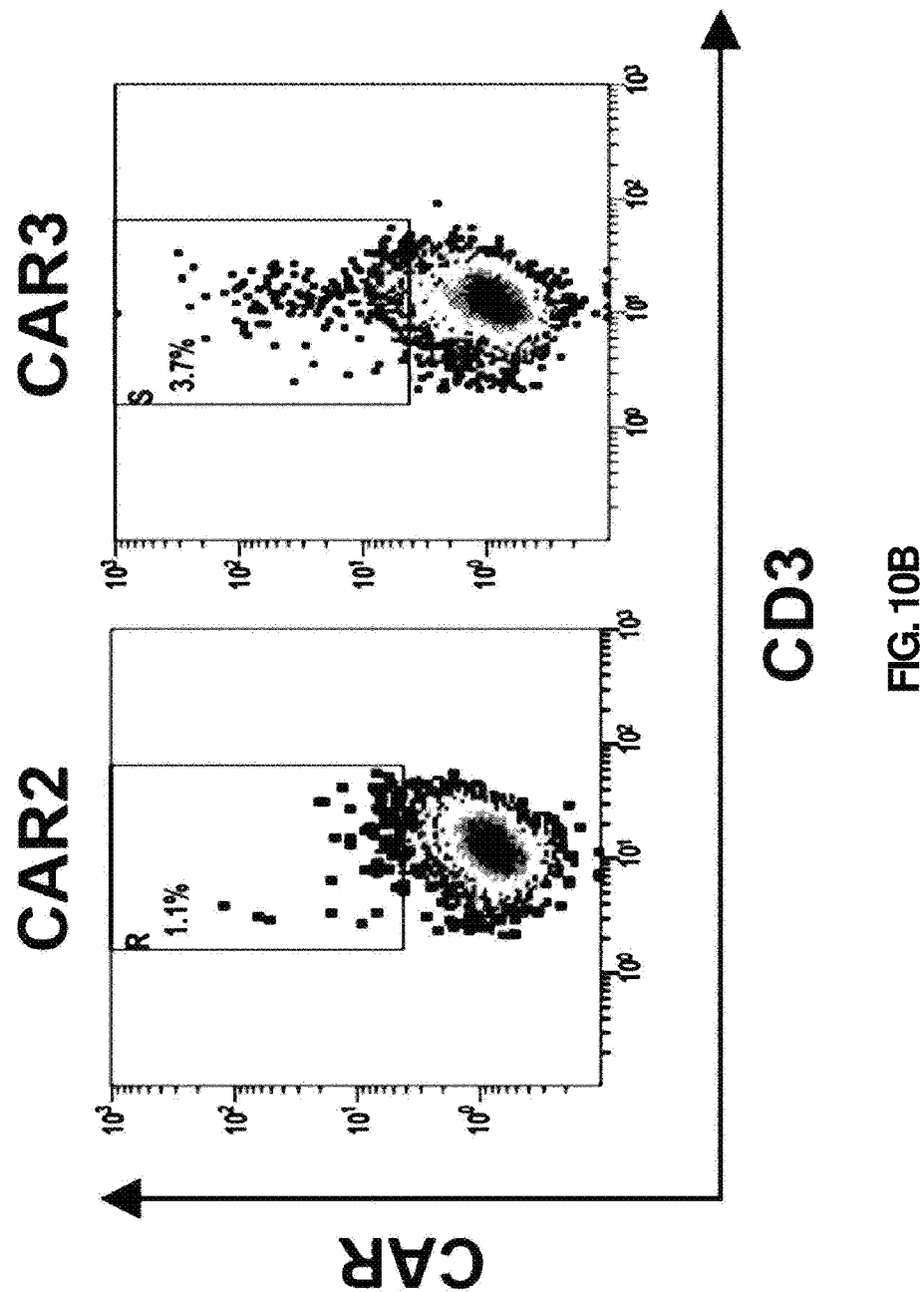
Figure 10C:
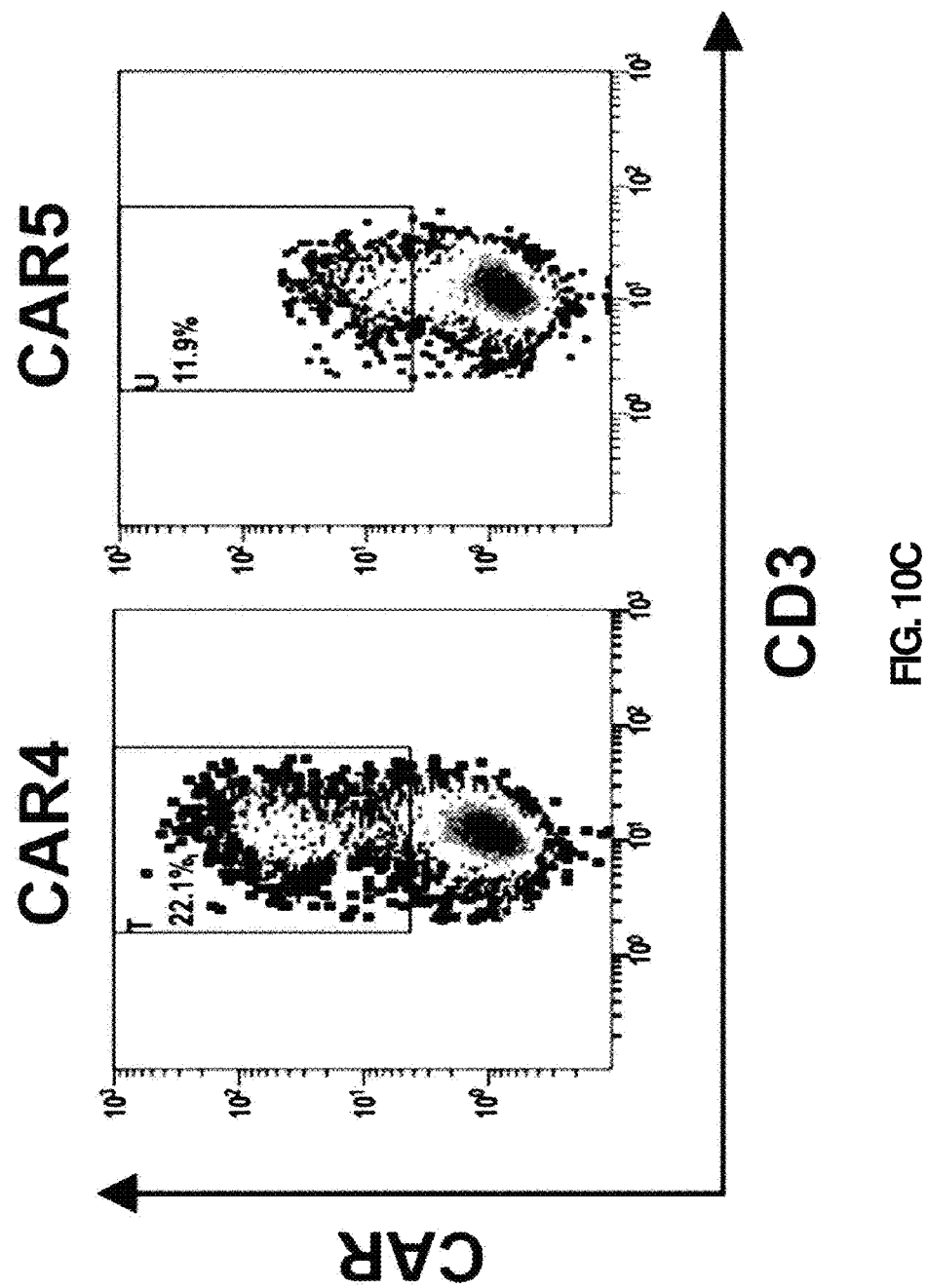
Figure 10D:
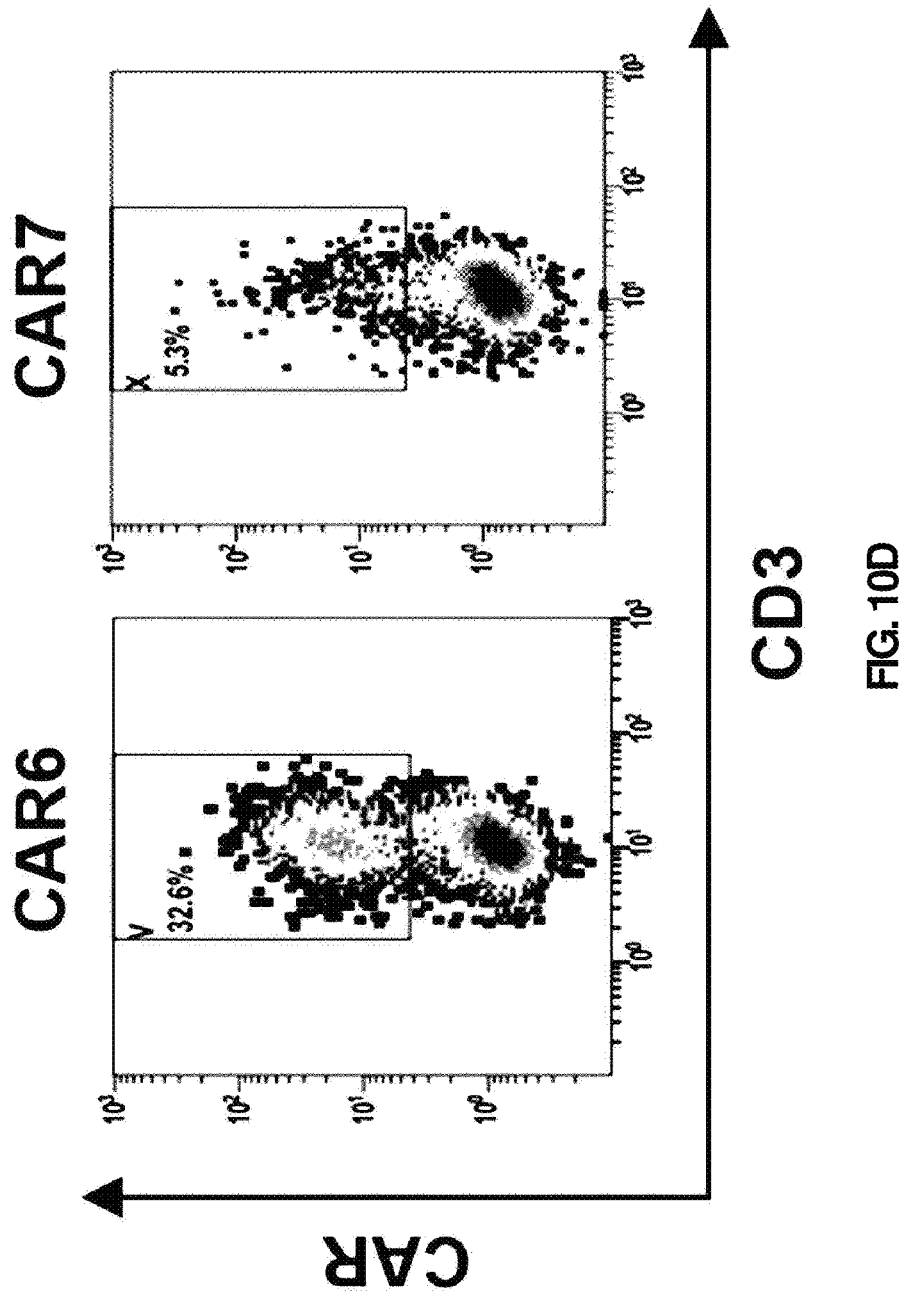

As can be seen in FIG. 8a, significant increases in the secretion of interferon gamma were detected in the experimental group treated with cytotoxic T cells (E) containing the antibody fragment of the present disclosure and the RaJi-Luc cells (T). After the cytotoxic T cells and RaJi-Luc cells were incubated together, luciferase was eluted by lysing the residual RaJi-Luc cells with 3× lysis buffer (75 mM Tris(pH 8.0), 30% glycerol, 3% Triton X100) and reacted with a substrate to examine the cytotoxic effect of the chimeric antigen receptor bearing the antibody fragment of the present disclosure. Percentages of lysis were determined relative to the signal detected in the well where only Raji-Luc cells were cultured. The chimeric antigen receptor T cells having the antibody fragment of the present disclosure increased in cytotoxicity with increasing of the treatment rate. Higher cytotoxic effects were detected in cytotoxic T cells having antibody fragments better in affinity than CD19_12.18 (FIG. 8b).

Example 10

Development of Chimeric Antigen Receptor Through Modification of Hinge Region, Transmembrane Domain, and Costimulatory Domain In order to optimize the activity of chimeric antigen receptors employing the developed antibody fragments, new chimeric antigen receptors (CAR2 to CAR7) were developed by modifying the constituents of chimeric antigen receptors, that is, hinge regions (CD8, CD28, and Fc), transmembrane domains (CD8, CD28, and ICOS), and costimulatory domains (CD137, CD28, ICOS, and CD3). As an antibody fragment binding to CD19 antigen, hzCD19_1218.81 was employed to identify activity (FIG. 9). For the chimeric antigen receptor in each of CAR1 to CAR7, digestion and ligation to pLenti6.3/V5-TOPO lentiviral vector (Invitrogen, USA) in which the promotor had been modified into EF-1 alpha were conducted in the same manner as in Example 8. The constructs thus obtained were identified by base sequencing. Amino acid and nucleotide sequences of the constructs of CAR1 to CAR7 are set forth as SEQ ID NOS: 74 to 87 in the appended sequence listing. Each of the developed constructs was used to prepare and enrich lentivirus according to the protocol of Example 8.

The developed chimeric antigen receptors were analyzed for activity. In this regard, cytotoxic T cells were prepared in the same manner as in Example 4 and examined to see whether or not the activity of CD19-expressing cells was specifically induced.

First, the obtained cytotoxic T cells were examined for CAR expression behavior. The expression of the chimeric antigen receptor was observed with the secondary antibody anti-human IgG FITC (Invitrogen, A11013) following primary binding of CD19-ECD. In this context, in order to examine whether the detected cells would be T cells or not, anti-human CD3 PE (Biolegend, 317308) was allowed to simultaneously participate in the binding, followed by flow cytometry. As a result of the assay, it was observed that the constructs (CAR2, CAR3) in which hinge region change occurred from CD8 to CD28 or Fc greatly decreased in CAR expression, compared to a construct employing a conventional CD8 hinge. In addition, the constructs in which the transmembrane domain and the costimulatory domain were changed were observed to decrease in CAR expression, compared to the case employing ICOS transmembrane domain and costimulatory domain (CAR5) (FIG. 10).

Figure 11A:
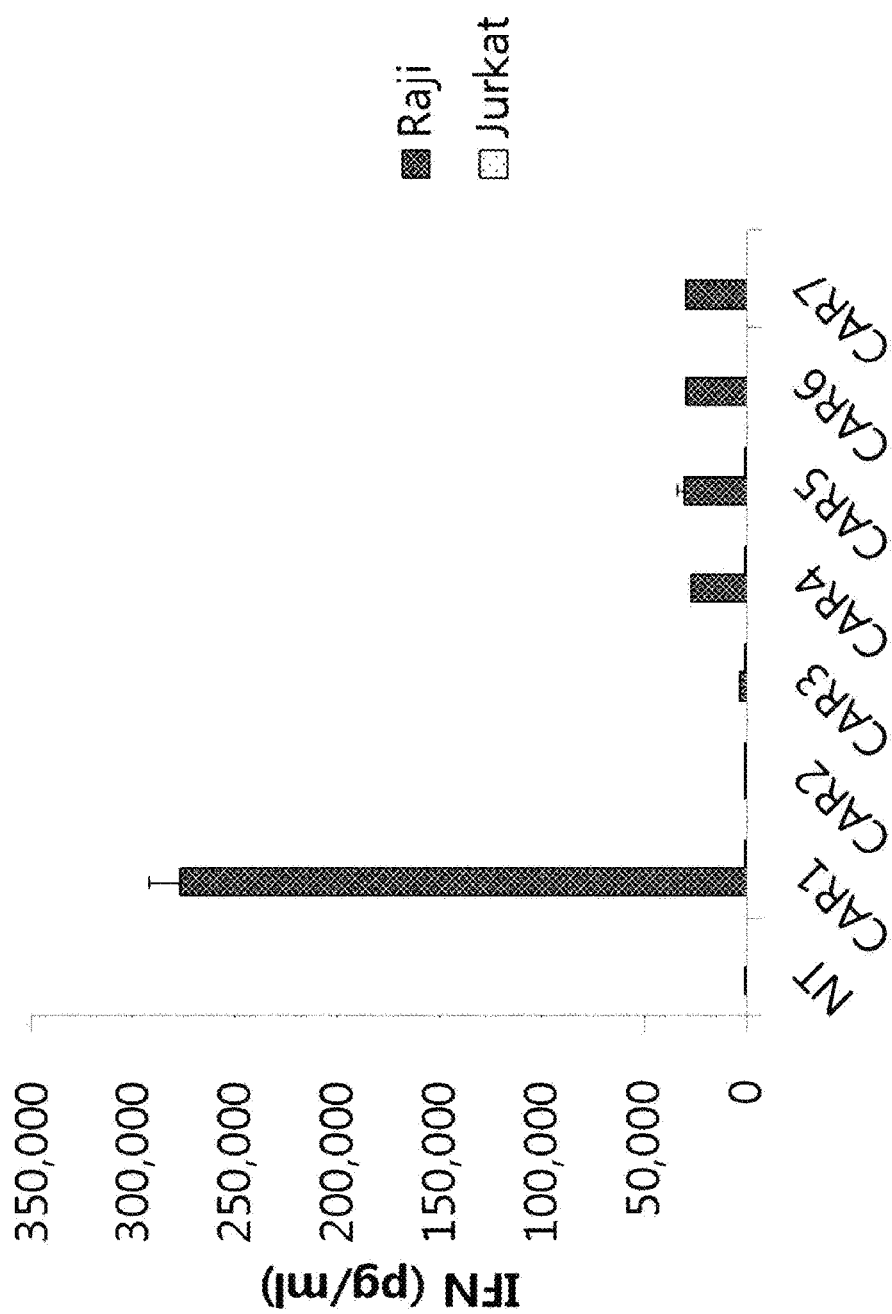
FIG. 11a is a bar graph showing activity of cytotoxic T cells expressing 7 chimeric antigen receptors as measured for levels of interferon gamma. CD19-positive RaJi cells and CD19-negative Jurkat cells were used as target cells and each co-cultured at a ratio of 1:5 with cytotoxic T cells, followed by measuring levels of interferon gamma.
Figure 11B:
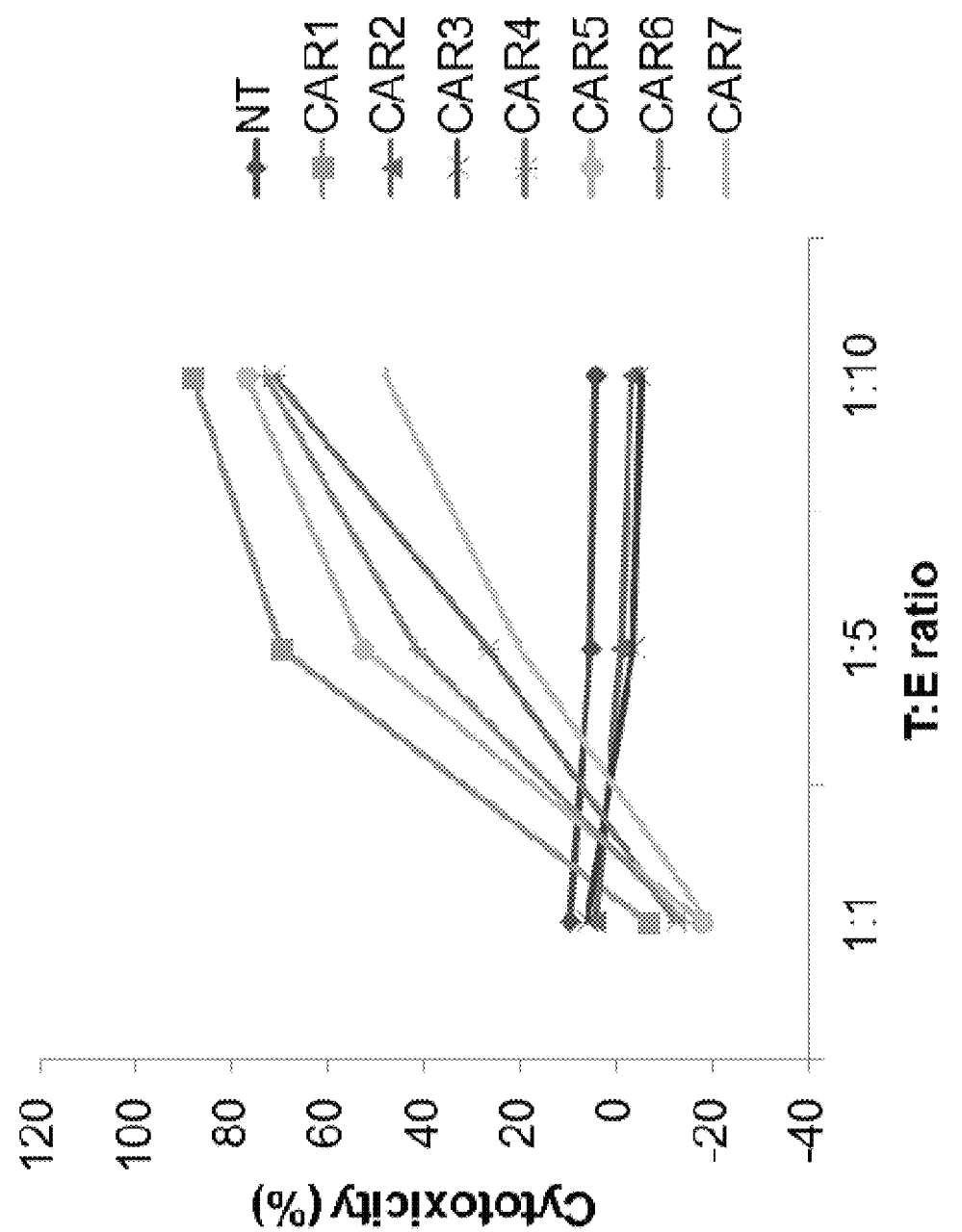
FIG. 11b is a plot showing activity of cytotoxic T cells as measured for luciferase activity of RaJi-Luc surviving after co-cultivation of RaJi-Luc cells and cytotoxic T cells.

The developed cytotoxic T cells were examined for activity in the same manner as in Example 8. CD19 positive RaJi-Luc cells and CD19 negative Jurkat cells were incubated, together with cytotoxic T cells, for 24 hours, and the cell cultures were measured for interferon gamma level and cytotoxicity. As shown in FIG. 11a, an increased level of interferon gamma was detected only in the group in which CD19 positive RaJi-Luc and cytotoxic T cells were co-cultured. Furthermore, construct CAR1, which showed the best expression among the CAR constructs used in the test, induced the highest interferon gamma secretion. Unlike interferon gamma secretion, cytotoxic effects were almost evenly high in all of the constructs CAR1, CAR4, CARS, CARE (FIG. 11b).

Example 11

Analysis of Epitope for CD19_1218 and Affinity-Improved Antibody

Figure 12A:
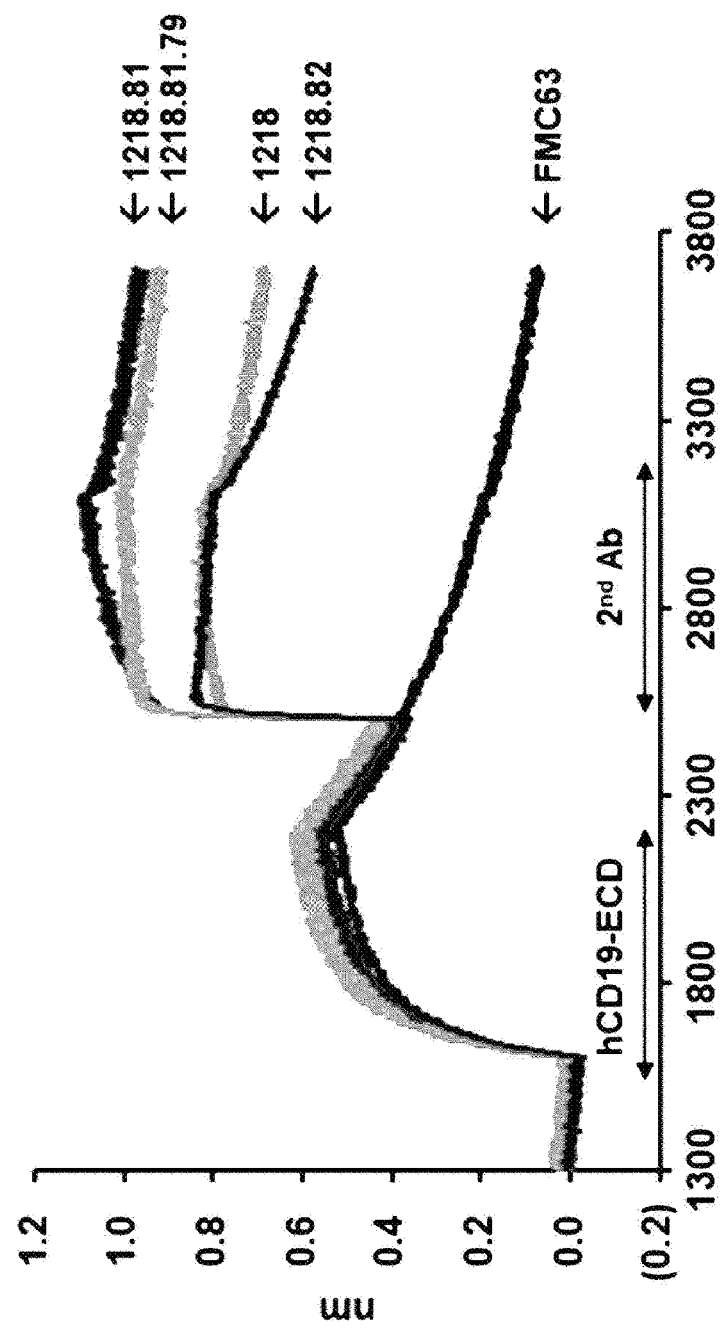
FIG. 12a shows results of the octet test to identify that CD19_1218, CD19_1218.81, CD19_1218.81.79, and CD19_1218.82 antibodies bind to epitope sites different from those to which FMC63 binds.
Figure 12B:
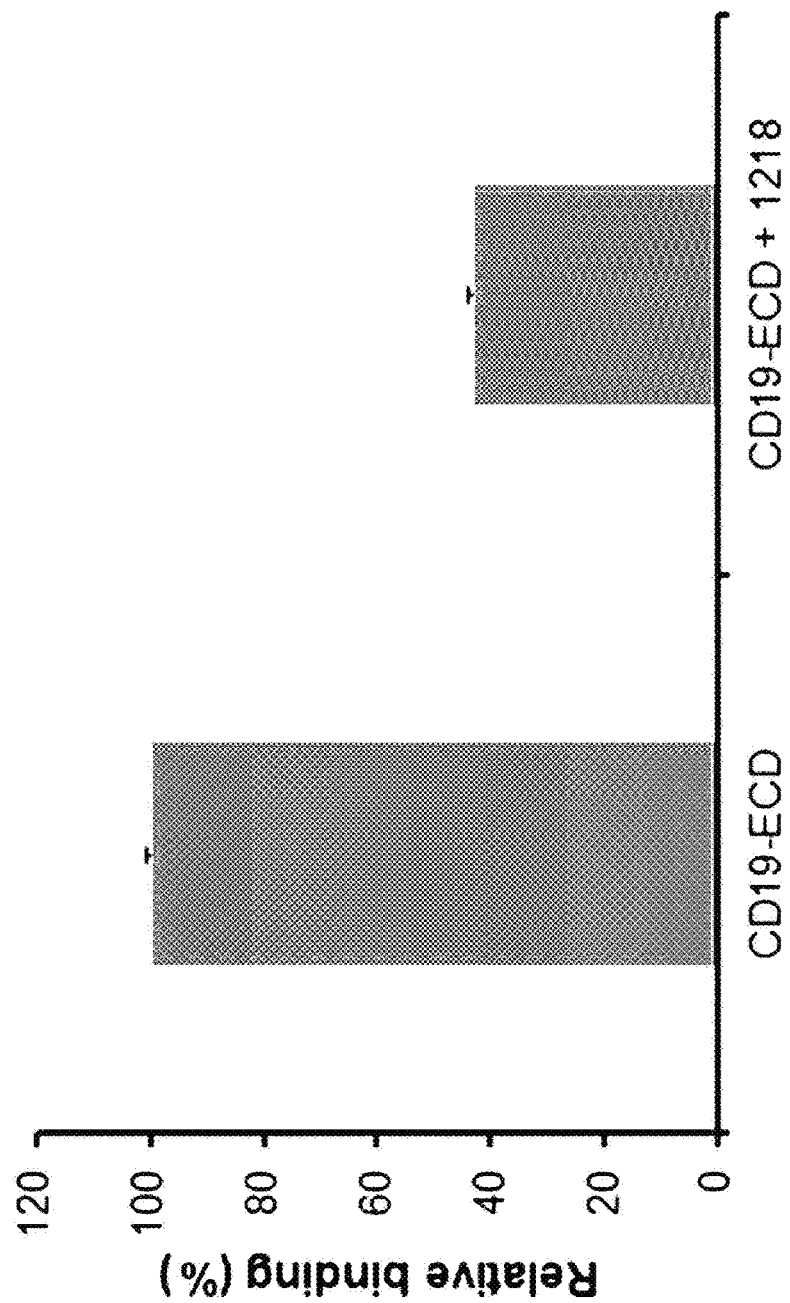
FIG. 12b shows results of competition ELISA using CD19_1218 and CD19_1218.81 antibodies. Relative binding is given when absorbance upon the absence of the competitor (CD19-ECD-Ck alone) is set forth as 100%.

To analyze whether the CD19_1218 antibody and the affinity-improved and humanized antibodies therefrom developed in the present disclosure had an epitope in common with each other, epitope binning and competition ELISA were conducted. As described in Example 2, CD19-ECD protein was bound to FMC63 antibody-immobilized sensor chip to which FMC63, CD19_1218, hzCD19_1218.81, hzCD19_1218.81.79, and hzCD19_1218.82 antibodies were then further applied (FIG. 12a). FMC63 did not further bind to the chip whereas the four antibodies including CD19_1218 did. For competition ELISA, an ELISA plate was coated with CD19_1218.81-Fc antibody at a concentration of 2 μg/mL to which CD19-ECD-Ck (3 μg/mL) was added alone or in combination with CD19_1218-Fc antibody (300 μg/mL). Subsequently, the CD19_1218.81-Fc-bound CD19-ECD-Ck protein was quantitated using an anti-Ck-HRP antibody. The presence of CD19_1218 antibody suppressed the binding of CD19_1218.81-Fc to CD19-ECD-Ck protein (FIG. 12b). Taken together, the data obtained above demonstrate that the developed antibodies have an epitope in common with CD19_1218 antibody.

This application contains references to amino acid sequences and/or nucleic acid sequences which have been submitted concurrently herewith as the sequence listing text file entitled "000207uscoa_SequenceListing.NRL", file size 138 kilobytes (KB), created on 5 Dec. 2022. The aforementioned sequence listing is hereby incorporated by reference in its entirety pursuant to 37 C.F.R. § 1.52(e)(5).

What is claimed is:

1. A nucleic acid molecule encoding an anti-CD19 antibody or an antigen-binding fragment thereof, the anti-CD19 antibody or the antigen-binding fragment thereof comprises the following:
   (i) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequences: CDRL1 of SEQ ID NO: 4, CDRL2 of SEQ ID NO: 5, and CDRL3 of SEQ ID NO: 6;
   (ii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequences: CDRL1 of SEQ ID NO: 4, CDRL2 of SEQ ID NO: 5, and CDRL3 of SEQ ID NO: 40;
   (iii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequences: CDRL1 of SEQ ID NO: 4, CDRL2 of SEQ ID NO: 5, and CDRL3 of SEQ ID NO: 41;
   (iv) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 30; and a light chain variable region comprising the following light chain CDR amino acid sequences: CDRL1 of SEQ ID NO: 4, CDRL2 of SEQ ID NO: 36, and CDRL3 of SEQ ID NO: 40;
   (v) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 31; and a light chain variable region comprising the following light chain CDR amino acid sequences: CDRL1 of SEQ ID NO: 4, CDRL2 of SEQ ID NO: 5, and CDRL3 of SEQ ID NO: 40;
   (vi) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 32; and a light chain variable region comprising the following light chain CDR amino acid sequences: CDRL1 of SEQ ID NO: 4, CDRL2 of SEQ ID NO: 37, and CDRL3 of SEQ ID NO: 40;
   (vii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 33; and a light chain variable region comprising the following light chain CDR amino acid sequences: CDRL1 of SEQ ID NO: 4, CDRL2 of SEQ ID NO: 38, and CDRL3 of SEQ ID NO: 40;
   (viii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 34; and a light chain variable region comprising the following light chain CDR amino acid sequences: CDRL1 of SEQ ID NO: 4, CDRL2 of SEQ ID NO: 39, and CDRL3 of SEQ ID NO: 40; or
   (ix) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 35; and a light chain variable region comprising the following light chain CDR amino acid sequences: CDRL1 of SEQ ID NO: 4, CDRL2 of SEQ ID NO: 5, and CDRL3 of SEQ ID NO: 40.

2. The nucleic acid molecule of claim 1, wherein the heavy chain variable region and the light chain variable region comprises, respectively:
   (i) the sequences of SEQ ID NOS: 7 and 8;
   (ii) the sequences of SEQ ID NOS: 42 and 43;
   (iii) the sequences of SEQ ID NOS: 46 and 47;
   (iv) the sequences of SEQ ID NOS: 50 and 51;
   (v) the sequences of SEQ ID NOS: 54 and 55;
   (vi) the sequences of SEQ ID NOS: 58 and 59;
   (vii) the sequences of SEQ ID NOS: 62 and 63;
   (viii) the sequences of SEQ ID NOS: 66 and 67; or
   (ix) the sequences of SEQ ID NOS: 70 and 71.

3. A recombinant vector comprising the nucleic acid molecule of claim 1.

4. An isolated host cell transformed with the recombinant vector of claim 3.

5. A nucleic acid molecule encoding a chimeric antigen receptor, the chimeric antigen receptor comprising the following:
   (a) an extracellular domain comprising an anti-CD19 antibody or an antigen-binding fragment thereof;
   (b) a transmembrane domain; and
   (c) an intracellular signaling domain,
   wherein the anti-CD19 antibody or the antigen-binding fragment thereof comprises:
   (i) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequences: CDRL1 of SEQ ID NO: 4, CDRL2 of SEQ ID NO: 5, and CDRL3 of SEQ ID NO: 6;
   (ii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequences:

CDRL1 of SEQ ID NO: 4, CDRL2 of SEQ ID NO: 5, and CDRL3 of SEQ ID NO: 40;
(iii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequences: CDRL1 of SEQ ID NO: 4, CDRL2 of SEQ ID NO: 5, and CDRL3 of SEQ ID NO: 41;
(iv) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 30; and a light chain variable region comprising the following light chain CDR amino acid sequences: CDRL1 of SEQ ID NO: 4, CDRL2 of SEQ ID NO: 36, and CDRL3 of SEQ ID NO: 40;
(v) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 31; and a light chain variable region comprising the following light chain CDR amino acid sequences: CDRL1 of SEQ ID NO: 4, CDRL2 of SEQ ID NO: 5, and CDRL3 of SEQ ID NO: 40;
(vi) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 32; and a light chain variable region comprising the following light chain CDR amino acid sequences: CDRL1 of SEQ ID NO: 4, CDRL2 of SEQ ID NO: 37, and CDRL3 of SEQ ID NO: 40;
(vii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 33; and a light chain variable region comprising the following light chain CDR amino acid sequences: CDRL1 of SEQ ID NO: 4, CDRL2 of SEQ ID NO: 38, and CDRL3 of SEQ ID NO: 40;
(viii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 34; and a light chain variable region comprising the following light chain CDR amino acid sequences: CDRL1 of SEQ ID NO: 4, CDRL2 of SEQ ID NO: 39, and CDRL3 of SEQ ID NO: 40; or
(ix) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 35; and a light chain variable region comprising the following light chain CDR amino acid sequences: CDRL1 of SEQ ID NO: 4, CDRL2 of SEQ ID NO: 5, and CDRL3 of SEQ ID NO: 40.

6. The nucleic acid molecule of claim 5, wherein the heavy chain variable region and the light chain variable region comprises, respectively:
(i) the sequences of SEQ ID NOS: 7 and 8;
(ii) the sequences of SEQ ID NOS: 42 and 43;
(iii) the sequences of SEQ ID NOS: 46 and 47;
(iv) the sequences of SEQ ID NOS: 50 and 51;
(v) the sequences of SEQ ID NOS: 54 and 55;
(vi) the sequences of SEQ ID NOS: 58 and 59;
(vii) the sequences of SEQ ID NOS: 62 and 63;
(viii) the sequences of SEQ ID NOS: 66 and 67; or
(ix) the sequences of SEQ ID NOS: 70 and 71.

7. A recombinant vector comprising the nucleic acid molecule of claim 5.

8. An isolated host cell transformed with the recombinant vector of claim 7.

9. An effector cell, expressing a chimeric antigen receptor, the chimeric antigen receptor comprising the following:
(a) an extracellular domain comprising an anti-CD19 antibody or an antigen-binding fragment thereof;
(b) a transmembrane domain; and
(c) an intracellular signaling domain,
wherein the anti-CD19 antibody or the antigen-binding fragment thereof comprises:
(i) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequences: CDRL1 of SEQ ID NO: 4, CDRL2 of SEQ ID NO: 5, and CDRL3 of SEQ ID NO: 6;
(ii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequences: CDRL1 of SEQ ID NO: 4, CDRL2 of SEQ ID NO: 5, and CDRL3 of SEQ ID NO: 40;
(iii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequences: CDRL1 of SEQ ID NO: 4, CDRL2 of SEQ ID NO: 5, and CDRL3 of SEQ ID NO: 41;
(iv) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 30; and a light chain variable region comprising the following light chain CDR amino acid sequences: CDRL1 of SEQ ID NO: 4, CDRL2 of SEQ ID NO: 36, and CDRL3 of SEQ ID NO: 40;
(v) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 31; and a light chain variable region comprising the following light chain CDR amino acid sequences: CDRL1 of SEQ ID NO: 4, CDRL2 of SEQ ID NO: 5, and CDRL3 of SEQ ID NO: 40;
(vi) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 32; and a light chain variable region comprising the following light chain CDR amino acid sequences: CDRL1 of SEQ ID NO: 4, CDRL2 of SEQ ID NO: 37, and CDRL3 of SEQ ID NO: 40;

(vii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 33; and a light chain variable region comprising the following light chain CDR amino acid sequences: CDRL1 of SEQ ID NO: 4, CDRL2 of SEQ ID NO: 38, and CDRL3 of SEQ ID NO: 40;

(viii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 34; and a light chain variable region comprising the following light chain CDR amino acid sequences: CDRL1 of SEQ ID NO: 4, CDRL2 of SEQ ID NO: 39, and CDRL3 of SEQ ID NO: 40; or (ix) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 35; and a light chain variable region comprising the following light chain CDR amino acid sequences: CDRL1 of SEQ ID NO: 4, CDRL2 of SEQ ID NO: 5, and CDRL3 of SEQ ID NO: 40.

10. The effector cell of claim 9, wherein the heavy chain variable region and the light chain variable region comprises, respectively:
(i) the sequences of SEQ ID NOS: 7 and 8;
(ii) the sequences of SEQ ID NOS: 42 and 43;
(iii) the sequences of SEQ ID NOS: 46 and 47;
(iv) the sequences of SEQ ID NOS: 50 and 51;
(v) the sequences of SEQ ID NOS: 54 and 55;
(vi) the sequences of SEQ ID NOS: 58 and 59;
(vii) the sequences of SEQ ID NOS: 62 and 63;
(viii) the sequences of SEQ ID NOS: 66 and 67; or
(ix) the sequences of SEQ ID NOS: 70 and 71.

11. The effector cell of claim 9, wherein the transmembrane domain is a transmembrane domain of a protein selected from the group consisting of alpha, beta, or zeta chain of T-cell receptor, CD27, CD28, CD3 epsilon, CD45, CD4, CD5, CD8, CD8α, CD9, CD16, CD22, CD33, CD37, CD64, CD80, CD86, CD134, CD137, and CD154.

12. The effector cell of claim 9, wherein the intracellular signaling domain is a CD3ζ (CD3 zeta) chain-derived domain.

13. The effector cell of claim 9, wherein the intracellular signaling domain further comprises a costimulatory molecule selected from the group consisting of OX40 (CD134), CD2, CD27, CD28, CDS, ICAM-1, LFA-1 (CD11a/CD18), and 4-1BB (CD137).

14. A pharmaceutical composition comprising the effector cell of claim 9.

* * * * *

SEQUENCE LISTING

```
Sequence total quantity: 93
SEQ ID NO: 1              moltype = AA  length = 5
FEATURE                   Location/Qualifiers
REGION                    1..5
                          note = Amino acid sequence of CDRH1 of CD19_12.18 antibody
source                    1..5
                          mol_type = protein
                          organism = synthetic construct
SEQUENCE: 1
SYDMG                                                                      5

SEQ ID NO: 2              moltype = AA  length = 17
FEATURE                   Location/Qualifiers
```

```
REGION                  1..17
                        note = Amino acid sequence of CDRH2 of CD19_12.18 antibody
source                  1..17
                        mol_type = protein
                        organism = synthetic construct
SEQUENCE: 2
GIDDDGRYTS YGSAVDG                                                      17

SEQ ID NO: 3            moltype = AA  length = 8
FEATURE                 Location/Qualifiers
REGION                  1..8
                        note = Amino acid sequence of CDRH3 of CD19_12.18 antibody
source                  1..8
                        mol_type = protein
                        organism = synthetic construct
SEQUENCE: 3
GNAGWIDA                                                                 8

SEQ ID NO: 4            moltype = AA  length = 9
FEATURE                 Location/Qualifiers
REGION                  1..9
                        note = Amino acid sequence of CDRL1 of CD19_12.18 antibody
source                  1..9
                        mol_type = protein
                        organism = synthetic construct
SEQUENCE: 4
SGGYSSYYG                                                                9

SEQ ID NO: 5            moltype = AA  length = 7
FEATURE                 Location/Qualifiers
REGION                  1..7
                        note = Amino acid sequence of CDRL2 of CD19_12.18 antibody
source                  1..7
                        mol_type = protein
                        organism = synthetic construct
SEQUENCE: 5
ESNKRPS                                                                  7

SEQ ID NO: 6            moltype = AA  length = 10
FEATURE                 Location/Qualifiers
REGION                  1..10
                        note = Amino acid sequence of CDRL3 of CD19_12.18 antibody
source                  1..10
                        mol_type = protein
                        organism = synthetic construct
SEQUENCE: 6
GGWDSTHAGI                                                              10

SEQ ID NO: 7            moltype = AA  length = 117
FEATURE                 Location/Qualifiers
REGION                  1..117
                        note = Amino acid sequence of heavy chain variable region
                         of CD19_12.18antibody
source                  1..117
                        mol_type = protein
                        organism = synthetic construct
SEQUENCE: 7
AVTLDESGGG LQTPGGALSL VCKASGFTFS SYDMGWVRQA PGKGLEFVAG IDDDGRYTSY        60
GSAVDGRATI SRDNGQSTVR LQLNNLRAED TATYYCTRGN AGWIDAWGHG TEVIVSS          117

SEQ ID NO: 8            moltype = AA  length = 106
FEATURE                 Location/Qualifiers
REGION                  1..106
                        note = Amino acid sequence of light chain variable region
                         of CD19_12.18antibody
source                  1..106
                        mol_type = protein
                        organism = synthetic construct
SEQUENCE: 8
LTQPSSVSAN PGETVKITCS GGYSSYYGWY QQKSPGSAPV TLIYESNKRP SDIPSRFSGS        60
ASGSTATLTI TGVQVEDEAV YYCGGWDSTH AGIFGAGTTL TVLGQS                      106

SEQ ID NO: 9            moltype = AA  length = 240
FEATURE                 Location/Qualifiers
REGION                  1..240
                        note = Amino acid sequence of CD19_12.18 scFv
source                  1..240
                        mol_type = protein
                        organism = synthetic construct
```

```
SEQUENCE: 9
LTQPSSVSAN PGETVKITCS GGYSSYYGWY QQKSPGSAPV TLIYESNKRP SDIPSRFSGS    60
ASGSTATLTI TGVQVEDEAV YYCGGWDSTH AGIFGAGTTL TVLGQSSRSS GGGGSSGGGG   120
SAVTLDESGG GLQTPGGALS LVCKASGFTF SSYDMGWVRQ APGKGLEFVA GIDDDGRYTS   180
YGSAVDGRAT ISRDNGQSTV RLQLNNLRAE DTATYYCTRG NAGWIDAWGH GTEVIVSSTS   240

SEQ ID NO: 10             moltype = DNA   length = 15
FEATURE                   Location/Qualifiers
misc_feature              1..15
                          note = Nucleotide sequence for encoding CDRH1 of CD19_12.18
                            antibody
source                    1..15
                          mol_type = other DNA
                          organism = synthetic construct
SEQUENCE: 10
agttacgaca tgggt                                                    15

SEQ ID NO: 11             moltype = DNA   length = 51
FEATURE                   Location/Qualifiers
misc_feature              1..51
                          note = Nucleotide sequence for encoding CDRH2 of CD19_12.18
                            antibody
source                    1..51
                          mol_type = other DNA
                          organism = synthetic construct
SEQUENCE: 11
ggtattgatg atgatggtag atacacatca tacgggtcgg cggtggatgg c             51

SEQ ID NO: 12             moltype = DNA   length = 24
FEATURE                   Location/Qualifiers
misc_feature              1..24
                          note = Nucleotide sequence for encoding CDRH3 of CD19_12.18
                            antibody
source                    1..24
                          mol_type = other DNA
                          organism = synthetic construct
SEQUENCE: 12
ggtaatgctg gttggatcga cgca                                          24

SEQ ID NO: 13             moltype = DNA   length = 27
FEATURE                   Location/Qualifiers
misc_feature              1..27
                          note = Nucleotide sequence for encoding CDRL1 of CD19_12.18
                            antibody
source                    1..27
                          mol_type = other DNA
                          organism = synthetic construct
SEQUENCE: 13
tccgggggtt acagcagcta ctatggc                                       27

SEQ ID NO: 14             moltype = DNA   length = 21
FEATURE                   Location/Qualifiers
misc_feature              1..21
                          note = Nucleotide sequence for encoding CDRL2 of CD19_12.18
                            antibody
source                    1..21
                          mol_type = other DNA
                          organism = synthetic construct
SEQUENCE: 14
gaaagcaaca agagaccctc g                                             21

SEQ ID NO: 15             moltype = DNA   length = 30
FEATURE                   Location/Qualifiers
misc_feature              1..30
                          note = Nucleotide sequence for encoding CDRL3 of CD19_12.18
                            antibody
source                    1..30
                          mol_type = other DNA
                          organism = synthetic construct
SEQUENCE: 15
ggtggctggg atagcactca tgctggtata                                    30

SEQ ID NO: 16             moltype = DNA   length = 351
FEATURE                   Location/Qualifiers
misc_feature              1..351
                          note = Nucleotide sequence for encoding heavy chain
                            variable region ofCD19_12.18 antibody
source                    1..351
                          mol_type = other DNA
```

```
                        organism = synthetic construct
SEQUENCE: 16
gccgtgacgt tggacgagtc cgggggcggc ctccagacgc ccggaggagc gctcagcctc    60
gtctgcaagg cctccgggtt caccttcagt agttacgaca tgggttgggt acgacaggcg   120
cccgcaagg ggctggagtt cgtcgctggt attgatgatg atggtagata cacatcatac    180
gggtcggcgg tggatggccg tgccaccatc tcgaggaca acgggcagag cacagtgagg    240
ctgcagctga caaccctcag ggctgaggac accgccacct actactgcac cagaggtaat   300
gctggttgga tcgacgcatg gggccacggg accgaagtca tcgtctcctc c            351

SEQ ID NO: 17          moltype = DNA  length = 318
FEATURE                Location/Qualifiers
misc_feature           1..318
                       note = Nucleotide sequence for encoding light chain
                        variable region ofCD19_12.18 antibody
source                 1..318
                       mol_type = other DNA
                       organism = synthetic construct
SEQUENCE: 17
ctgactcagc cgtcctcggt gtcagcaaac ccaggagaaa ccgtcaagat cacctgctcc    60
gggggttaca gcagctacta tggctggtac cagcagaagt ctcctggcag tgcccctgtc   120
actctgatct atgaaagcaa caagagaccc tcggacatcc cttcacgatt ctccggttcc   180
gcatccggct ccacagccac attaaccatc actggggtcc aagtcgagga cgaggctgtc   240
tattactgtg gtggctggga tagcactcat gctggtatat tggggccgg gacaaccctg   300
accgtcctag gtcagtcc                                                318

SEQ ID NO: 18          moltype = DNA  length = 720
FEATURE                Location/Qualifiers
misc_feature           1..720
                       note = Nucleotide sequence for encoding CD19_12.18 scFv
source                 1..720
                       mol_type = other DNA
                       organism = synthetic construct
SEQUENCE: 18
ctgactcagc cgtcctcggt gtcagcaaac ccaggagaaa ccgtcaagat cacctgctcc    60
gggggttaca gcagctacta tggctggtac cagcagaagt ctcctggcag tgcccctgtc   120
actctgatct atgaaagcaa caagagaccc tcggacatcc cttcacgatt ctccggttcc   180
gcatccggct ccacagccac attaaccatc actggggtcc aagtcgagga cgaggctgtc   240
tattactgtg gtggctggga tagcactcat gctggtatat tggggccgg gacaaccctg    300
accgtcctag gtcagtcctc tagatcttcc ggcggttgtg gcagctccgg tggtggcagt   360
tccgccgtga cgttggacga gtccgggggc ggcctccaga cgcccggagg agcgctcagc   420
ctcgtctgca aggcctccgg gttcaccttc agtagttacg acatgggttg ggtacgacag   480
gcgcccggca aggggctgga gttcgtcgct ggtattgatg atgatggtag atacacatca   540
tacgggtcg cggtggatgg ccgtgccacc atctcgagga caacgggca  gagcacagtg    600
aggctgcagc tgaacaacct cagggctgag gacaccgcca cctactactg caccagaggt   660
aatgctggtt ggatcgacgc atgggggcca cgggaccgaag tcatcgtctc tccactagt   720

SEQ ID NO: 19          moltype = DNA  length = 63
FEATURE                Location/Qualifiers
misc_feature           1..63
                       note = Nucleotide sequence for encoding CD8 leader
source                 1..63
                       mol_type = other DNA
                       organism = synthetic construct
SEQUENCE: 19
atggccctgc ctgtgaccgc tctgctgctg ccctggctc tgctgctgca cgccgctcgc    60
ccc                                                                63

SEQ ID NO: 20          moltype = DNA  length = 207
FEATURE                Location/Qualifiers
misc_feature           1..207
                       note = Nucleotide sequence for encoding CD8
                        hinge/transmembrain domain
source                 1..207
                       mol_type = other DNA
                       organism = synthetic construct
SEQUENCE: 20
accacaactc cagctccccg gccccctacc cctgcaccaa caatcgccag ccagcctctg    60
tccctgagac cagaggcatg taggccagct gcaggaggag cagtgcatac aagaggcctg   120
gacttcgcct gcgatatcta catttgggct cctctgcag gaacttgtgg cgtgctgctg    180
ctgtctctgg tcatcaccct gtactgc                                      207

SEQ ID NO: 21          moltype = DNA  length = 126
FEATURE                Location/Qualifiers
misc_feature           1..126
                       note = Nucleotide sequence for encoding intracellular
                        domain of CD137
source                 1..126
                       mol_type = other DNA
                       organism = synthetic construct
```

```
SEQUENCE: 21
aaaaggggcc gcaagaaact gctgtatatt ttcaagcagc ccttcatgcg gcccgtgcag    60
accacacagg aggaagacgg gtgctcctgt agattccccg aggaagagga aggcgggtgt   120
gagctg                                                              126

SEQ ID NO: 22           moltype = DNA   length = 336
FEATURE                 Location/Qualifiers
misc_feature            1..336
                        note = Nucleotide sequence for encoding intracellular
                         domain of CD3-zeta
source                  1..336
                        mol_type = other DNA
                        organism = synthetic construct
SEQUENCE: 22
cgcgtcaagt tcagccgatc agccgatgct cctgcataca agcagggcca gaatcagctg    60
tataacgagc tgaatctggg cgccgagag gaatacgacg tgctggataa gcggagaggg   120
agggaccccg aaatgggagg caaacctagg cgcaagaacc cacaggaggg actgtacaat   180
gaactgcaga aggacaaaat ggccgaggct tattccgaaa ttgggatgaa aggagagcga   240
cggagaggga agggacacga tgggctgtat cagggactgt ctaccgccac taaagatacc   300
tacgacgctc tgcacatgca ggctctgcca cctcgc                             336

SEQ ID NO: 23           moltype = DNA   length = 1482
FEATURE                 Location/Qualifiers
misc_feature            1..1482
                        note = Nucleotide sequence of CAR construct comprising
                         CD19_12.18 scFv
source                  1..1482
                        mol_type = other DNA
                        organism = synthetic construct
SEQUENCE: 23
atggccctgc ctgtgaccgc tctgctgctg cccctggctc tgctgctgca cgccgctcgc    60
cccgtggccc aggcggccct gactcagccg tcctcggtgt cagcaaaccc aggagaaacc   120
gtcaagatca cctgctccgg gggttacagc agctactatg ctggtacca gcagaagtct   180
cctggcagtg cccctgtcac tctgatctat gaaagcaaca agaccctgc ggacatccct   240
tcacgattct ccggttccgc atccggctcc acagccacat taaccatcac tggggtccaa   300
gtcgaggacg aggctgtcta ttactgtggg ggctgggata gcactcatgc tggtatattt   360
ggggccggga caaccctgac cgtcctaggt cagtcctcta gatcttccgg cggtggtggc   420
agctccggtg gtggcggttc cgccgtgacg ttggacgagt ccgggggcgg cctccagacg   480
cccggaggag cgctcagcct cgtctgcaag gcctccggat tcacctttag tagttacgac   540
atgggttggg tacgcaggc gcccggcaag gggctgagt tcgtcgctgg tattgatgat   600
gatggtagat acacatcata cggtcgcgcg gtggatggcc gtgccaccat ctcgagggac   660
aacgggcaga gcacagtgag gctgcagctg aacaacctcg ggctgagga caccgccacc   720
tactactgca ccagaggtaa tgctggttgg atcgacgcat gggcccacgg gaccgaagtc   780
atcgtctcct ccactagtgg ccaggccggc cagaccacaa ctccagctcc cggccccct   840
accctgcac caacaatcgc cagccagcct ctgtccctga ccagaggc atgtaggcca   900
gctgcaggag gagcagtgca tacaagaggc ctggacttcg cctgcgatat ctacatttgg   960
gctcctctgg caggaacttg tggcgtgctg ctgctgtctc tggtcatcac cctgtactgc  1020
aaaaggggcc gcaagaaact gctgtatatt ttcaagcagc ccttcatgcg gcccgtgcag  1080
accacacagg aggaagacgg gtgctcctgt agattccccg aggaagagga aggcgggtgt  1140
gagctgcgct caagttcag ccgatcagcc gatgctcctg catacaagca gggccagaat  1200
cagctgtata acgagctgaa tctggggcgc cgagaggaat acgacgtgct ggataagcga  1260
agagggaggg accccgaaat gggaggcaaa cctaggcgca agaacccaca ggagggactg  1320
tacaatgaac tgcagaagga caaaatggcc gaggcttatt ccgaaattgg gatgaaagga  1380
gagcgacgga gagggaaggg acacgatggg ctgtatcagg gactgtctac cgccactaaa  1440
gatacctacg acgctctgca catgcaggct ctgccacctc gc                     1482

SEQ ID NO: 24           moltype = DNA   length = 72
FEATURE                 Location/Qualifiers
misc_feature            1..72
                        note = Heavy chain sense primer for Creation of a chicken
                         scFv Abphage-display library
source                  1..72
                        mol_type = other DNA
                        organism = synthetic construct
SEQUENCE: 24
ggtcagtcct ctagatcttc cggcggtggt ggcagctccg gtggtggcgg ttccgccgtg    60
acgttggacg ag                                                        72

SEQ ID NO: 25           moltype = DNA   length = 44
FEATURE                 Location/Qualifiers
misc_feature            1..44
                        note = Heavy chain antisense primer for Creation of a
                         chicken scFv Abphage-display library
source                  1..44
                        mol_type = other DNA
                        organism = synthetic construct
SEQUENCE: 25
ctggccggcc tggccactag tggaggagac gatgacttcg gtcc                     44
```

```
SEQ ID NO: 26              moltype = DNA   length = 38
FEATURE                    Location/Qualifiers
misc_feature               1..38
                           note = Light chain sense primer for Creation of a chicken
                           scFv Abphage-display library
source                     1..38
                           mol_type = other DNA
                           organism = synthetic construct
SEQUENCE: 26
gtggcccagg cggccctgac tcagccgtcc tcggtgtc                                   38

SEQ ID NO: 27              moltype = DNA   length = 34
FEATURE                    Location/Qualifiers
misc_feature               1..34
                           note = Light chain antisense primer for Creation of a
                           chicken scFv Abphage-display library
source                     1..34
                           mol_type = other DNA
                           organism = synthetic construct
SEQUENCE: 27
ggaagatcta gaggactgac ctaggacggt cagg                                       34

SEQ ID NO: 28              moltype = DNA   length = 42
FEATURE                    Location/Qualifiers
misc_feature               1..42
                           note = Nested sense primer for Creation of a chicken scFv
                           Abphage-display library
source                     1..42
                           mol_type = other DNA
                           organism = synthetic construct
SEQUENCE: 28
gaggaggagg aggaggaggt ggcccaggcg gccctgactc ag                              42

SEQ ID NO: 29              moltype = DNA   length = 47
FEATURE                    Location/Qualifiers
misc_feature               1..47
                           note = Nested antisense primer for Creation of a chicken
                           scFv Abphage-display library
source                     1..47
                           mol_type = other DNA
                           organism = synthetic construct
SEQUENCE: 29
gaggaggagg aggaggagga gctggccggc ctggccacta gtggagg                         47

SEQ ID NO: 30              moltype = AA   length = 8
FEATURE                    Location/Qualifiers
REGION                     1..8
                           note = CDRH3 of hzCD19_1218.81.12
source                     1..8
                           mol_type = protein
                           organism = synthetic construct
SEQUENCE: 30
GNAGWIST                                                                     8

SEQ ID NO: 31              moltype = AA   length = 8
FEATURE                    Location/Qualifiers
REGION                     1..8
                           note = CDRH3 of hzCD19_1218.81.17
source                     1..8
                           mol_type = protein
                           organism = synthetic construct
SEQUENCE: 31
GNAGWIET                                                                     8

SEQ ID NO: 32              moltype = AA   length = 8
FEATURE                    Location/Qualifiers
REGION                     1..8
                           note = CDRH3 of hzCD19_1218.81.52
source                     1..8
                           mol_type = protein
                           organism = synthetic construct
SEQUENCE: 32
GNAGWILT                                                                     8

SEQ ID NO: 33              moltype = AA   length = 8
FEATURE                    Location/Qualifiers
REGION                     1..8
                           note = CDRH3 of hzCD19_1218.81.55
source                     1..8
```

```
                              mol_type = protein
                              organism = synthetic construct
SEQUENCE: 33
GNAGWIQN                                                                              8

SEQ ID NO: 34                 moltype = AA   length = 8
FEATURE                       Location/Qualifiers
REGION                        1..8
                              note = CDRH3 of hzCD19_1218.81.64
source                        1..8
                              mol_type = protein
                              organism = synthetic construct
SEQUENCE: 34
GNAGWIQT                                                                              8

SEQ ID NO: 35                 moltype = AA   length = 8
FEATURE                       Location/Qualifiers
REGION                        1..8
                              note = CDRH3 of hzCD19_1218.81.79
source                        1..8
                              mol_type = protein
                              organism = synthetic construct
SEQUENCE: 35
GNAGWIDH                                                                              8

SEQ ID NO: 36                 moltype = AA   length = 7
FEATURE                       Location/Qualifiers
REGION                        1..7
                              note = CDRL2 of hzCD19_1218.81.12
source                        1..7
                              mol_type = protein
                              organism = synthetic construct
SEQUENCE: 36
ESDKRPA                                                                               7

SEQ ID NO: 37                 moltype = AA   length = 7
FEATURE                       Location/Qualifiers
REGION                        1..7
                              note = CDRL2 of hzCD19_1218.81.52
source                        1..7
                              mol_type = protein
                              organism = synthetic construct
SEQUENCE: 37
ETDKRPQ                                                                               7

SEQ ID NO: 38                 moltype = AA   length = 7
FEATURE                       Location/Qualifiers
REGION                        1..7
                              note = CDRL2 of hzCD19_1218.81.55
source                        1..7
                              mol_type = protein
                              organism = synthetic construct
SEQUENCE: 38
ESGKRPA                                                                               7

SEQ ID NO: 39                 moltype = AA   length = 7
FEATURE                       Location/Qualifiers
REGION                        1..7
                              note = CDRL2 of hzCD19_1218.81.64
source                        1..7
                              mol_type = protein
                              organism = synthetic construct
SEQUENCE: 39
ESQKRPL                                                                               7

SEQ ID NO: 40                 moltype = AA   length = 10
FEATURE                       Location/Qualifiers
REGION                        1..10
                              note = CDRL3 of hzCD19_1218.81
source                        1..10
                              mol_type = protein
                              organism = synthetic construct
SEQUENCE: 40
GGLTPTHAGI                                                                           10

SEQ ID NO: 41                 moltype = AA   length = 10
FEATURE                       Location/Qualifiers
REGION                        1..10
                              note = CDRL3 of hzCD19_1218.82
```

```
source                       1..10
                             mol_type = protein
                             organism = synthetic construct
SEQUENCE: 41
GQSTRTHAGI                                                              10

SEQ ID NO: 42                moltype = AA   length = 117
FEATURE                      Location/Qualifiers
REGION                       1..117
                             note = Heavy chain of hzCD19_1218.81 (aa)
source                       1..117
                             mol_type = protein
                             organism = synthetic construct
SEQUENCE: 42
EVQLVESGGG LVQPGGSLRL SCAASGFTFS SYDMGWVRQA PGKGLEFVAG IDDDGRYTSY        60
GSAVDGRATI SRDNAKNTLY LQMNSLRAED TAVYYCTRGN AGWIDAWGQG TLVTVSS          117

SEQ ID NO: 43                moltype = AA   length = 105
FEATURE                      Location/Qualifiers
REGION                       1..105
                             note = Light chain of hzCD19_1218.81 (aa)
source                       1..105
                             mol_type = protein
                             organism = synthetic construct
SEQUENCE: 43
QSVLTQPPSV SAAPGQKVTI SCSGGYSSYY GWYQQLPGTA PKTLIYESNK RPSGIPDRFS        60
GSASGSSATL GITGLQTGDE ADYYCGGLTP THAGIFGGGT KLTVL                       105

SEQ ID NO: 44                moltype = DNA   length = 351
FEATURE                      Location/Qualifiers
misc_feature                 1..351
                             note = Heavy chain of hzCD19_1218.81 (nt)
source                       1..351
                             mol_type = other DNA
                             organism = synthetic construct
SEQUENCE: 44
gaagttcagc tggttgaatc tggcggagga ctggtgcaac tggcggatc tctgagactg         60
tcttgtgccg ccagcggctt caccttcagc agctatgata tgggctgggt ccgacaggcc      120
cctggcaaag acttgagtt tgtggccggc atcgacgacg atggcagata cacaagctac       180
ggctctgccg tggatggcag ggccaccatt agcagagaca acgccaagaa cacccctac       240
ctgcagatga acagcctgag agccgaggac accgccgtgt actactgtac aagaggcaac      300
gccggatgga tcgatgcctg gggacagggc acactggtca ccgtgtcaag c              351

SEQ ID NO: 45                moltype = DNA   length = 315
FEATURE                      Location/Qualifiers
misc_feature                 1..315
                             note = Light chain of hzCD19_1218.81 (nt)
source                       1..315
                             mol_type = other DNA
                             organism = synthetic construct
SEQUENCE: 45
cagtctgtgc tgacacagcc tccatctgtg tctgctgccc ctggccagaa agtgacaatc        60
agctgtagcg gcggctactc cagctactac ggatggtatc agcagctgcc tggcacagcc      120
cctaagacac tgatctacga gagcaacaag aggcccagcg gcatccctga tagattttct      180
ggcagcgcct ctggcagctc tgccacactg ggaattacag gactgcagac aggcgacgag      240
gccgattact attgtggcgg cctgacacct acacacgccg gaatttttgg cggaggcacc      300
aagctgacag tgctc                                                       315

SEQ ID NO: 46                moltype = AA   length = 117
FEATURE                      Location/Qualifiers
REGION                       1..117
                             note = Heavy chain of hzCD19_1218.81.12 (aa)
source                       1..117
                             mol_type = protein
                             organism = synthetic construct
SEQUENCE: 46
EVQLVESGGG LVQPGGSLRL SCAASGFTFS SYDMGWVRQA PGKGLEFVAG IDDDGRYTSY        60
GSAVDGRATI SRDNAKNTVY LQMNSLRAED TAVYYCTRGN AGWISTWGQG TLVTVSS         117

SEQ ID NO: 47                moltype = AA   length = 105
FEATURE                      Location/Qualifiers
REGION                       1..105
                             note = Light chain of hzCD19_1218.81.12 (aa)
source                       1..105
                             mol_type = protein
                             organism = synthetic construct
SEQUENCE: 47
QSVLTQPPSV SAAPGQKVTI SCSGGYSSYY GWYQQLPGTA PKTLIYESDK RPAGIPDRFS        60
GSASGSSATL GITGLQTGDE ADYYCGGLTP THAGIFGGGT KLTVL                      105
```

```
SEQ ID NO: 48            moltype = DNA  length = 351
FEATURE                  Location/Qualifiers
misc_feature             1..351
                         note = Heavy chain of hzCD19_1218.81.12 (nt)
source                   1..351
                         mol_type = other DNA
                         organism = synthetic construct
SEQUENCE: 48
gaggtgcagc tggtagagtc cggcggcggc ctcgtccaac caggcggctc cctcagattg    60
agctgtgctg ccagcggctt cactttcagc tcttatgaca tgggttgggt gagacaggca   120
cctggcaagg gtctggaatt cgtagccggc atcgacgatg acggtagata caccagttac   180
ggctctgctg tcgatggtcg cgctaccatt agccgagata cgccaagaa taccgtttat    240
cttcaaatga attcactgag ggcagaagac acagccgttt actattgtac tagaggtaac   300
gccgggtgga tttcgacttg gggacagggc acactggtac ccgtgagttc a            351

SEQ ID NO: 49            moltype = DNA  length = 315
FEATURE                  Location/Qualifiers
misc_feature             1..315
                         note = Light chain of hzCD19_1218.81.12 (nt)
source                   1..315
                         mol_type = other DNA
                         organism = synthetic construct
SEQUENCE: 49
cagtcagtcc taactcagcc cccctcagtg agtgcggctc cggggcagaa agtgacaatc    60
tcgtgcagcg gaggctacag ctcttattac ggatggtatc agcagctgcc aggaaccgcc   120
cccaagaccc ttatctacga gtccgacaaa cggcctgcag ggataccaga caggttttca   180
ggcagtgcgt ctggttcctc tgccacgctc ggcatcaccg gctgcaaac aggagacgag    240
gcagattatt attgcggagg actgacgcct actcacgcag gaattttttgg aggtggaaca  300
aaattaacag tgttg                                                    315

SEQ ID NO: 50            moltype = AA   length = 117
FEATURE                  Location/Qualifiers
REGION                   1..117
                         note = Heavy chain of hzCD19_1218.81.17 (aa)
source                   1..117
                         mol_type = protein
                         organism = synthetic construct
SEQUENCE: 50
EVQLVESGGG LVQPGGSLRL SCAASGFTFS SYDMGWVRQA PGKGLEFVAG IDDDGRYTSY    60
GSAVDGRATI SRDNAKNTVY LQMNSLRAED TAVYYCTRGN AGWIETWGQG TLVTVSS      117

SEQ ID NO: 51            moltype = AA   length = 105
FEATURE                  Location/Qualifiers
REGION                   1..105
                         note = Light chain of hzCD19_1218.81.17 (aa)
source                   1..105
                         mol_type = protein
                         organism = synthetic construct
SEQUENCE: 51
QSVLTQPPSV SAAPGQKVTI SCSGGYSSYY GWYQQLPGTA PKTLIYESNK RPSGIPDRFS    60
GSASGSSATL GITGLQTGDE ADYYCGGLTP THAGIFGGGT KLTVL                   105

SEQ ID NO: 52            moltype = DNA  length = 351
FEATURE                  Location/Qualifiers
misc_feature             1..351
                         note = Heavy chain of hzCD19_1218.81.17 (nt)
source                   1..351
                         mol_type = other DNA
                         organism = synthetic construct
SEQUENCE: 52
gaggtgcagc tggtagagtc cggcggcggc ctcgtccaac caggcggctc cctcagattg    60
agctgtgctg ccagcggctt cactttcagc tcttatgaca tgggttgggt gagacaggca   120
cctggcaagg gtctggaatt cgtagccggc atcgacgatg acggtagata caccagttac   180
ggctctgctg tcgatggtcg cgctaccatt agccgagata cgccaagaa taccgtttat    240
cttcaaatga attcactgag ggcagaagac acagccgttt actattgtac tagaggtaac   300
gccgggtgga ttgagacgtg gggacagggc acactggtga ccgtgagttc a            351

SEQ ID NO: 53            moltype = DNA  length = 315
FEATURE                  Location/Qualifiers
misc_feature             1..315
                         note = Light chain of hzCD19_1218.81.17 (nt)
source                   1..315
                         mol_type = other DNA
                         organism = synthetic construct
SEQUENCE: 53
cagtcagtcc taactcagcc cccctcagtg agtgcggctc cggggcagaa agtgacaatc    60
tcgtgcagcg gaggctacag ctcttattac ggatggtatc agcagctgcc aggaaccgcc   120
cccaagaccc ttatctacga gtcaaataaa cggcctcag ggataccaga caggttttca    180
```

```
ggcagtgcgt ctggttcctc tgccacgctc ggcatcaccg ggctgcaaac aggagacgag    240
gcagattatt attgcggagg actgacgcct actcacgcag gaattttggg aggtggaaca    300
aaattaacag tgttg                                                     315

SEQ ID NO: 54           moltype = AA  length = 117
FEATURE                 Location/Qualifiers
REGION                  1..117
                        note = Heavy chain of hzCD19_1218.81.52 (aa)
source                  1..117
                        mol_type = protein
                        organism = synthetic construct
SEQUENCE: 54
EVQLVESGGG LVQPGGSLRL SCAASGFTFS SYDMGWVRQA PGKGLEFVAG IDDDGRYTSY    60
GSAVDGRATI SRDNAKNTVY LQMNSLRAED TAVYYCTRGN AGWILTWGQG TLVTVSS      117

SEQ ID NO: 55           moltype = AA  length = 105
FEATURE                 Location/Qualifiers
REGION                  1..105
                        note = Light chain of hzCD19_1218.81.52 (aa)
source                  1..105
                        mol_type = protein
                        organism = synthetic construct
SEQUENCE: 55
QSVLTQPPSV SAAPGQKVTI SCSGGYSSYY GWYQQLPGTA PKTLIYETDK RPQGIPDRFS    60
GSASGSSATL GITGLQTGDE ADYYCGGLTP THAGIFGGGT KLTVL                   105

SEQ ID NO: 56           moltype = DNA  length = 351
FEATURE                 Location/Qualifiers
misc_feature            1..351
                        note = Heavy chain of hzCD19_1218.81.52 (nt)
source                  1..351
                        mol_type = other DNA
                        organism = synthetic construct
SEQUENCE: 56
gaggtgcagc tggtagagtc cggcggcggc ctcgtccaac caggcggctc cctcagattg    60
agctgtgctg ccagcggctt cactttcagc tcttatgaca tgggttgggt gagacaggca    120
cctggcaagg gtctggaatt cgtagccggc atcgacgatg acggtagata caccagttac    180
ggctctgctg tcgatggtcg cgctaccatt agccgagata cgccaagaa  taccgtttat    240
cttcaaatga attcactgag ggcagaagac acagccgttt actattgtac tagaggtaac    300
gccgggtgga ttcttacttg gggacagggc acactggtga ccgtgagttc a             351

SEQ ID NO: 57           moltype = DNA  length = 315
FEATURE                 Location/Qualifiers
misc_feature            1..315
                        note = Light chain of hzCD19_1218.81.52 (nt)
source                  1..315
                        mol_type = other DNA
                        organism = synthetic construct
SEQUENCE: 57
cagtcagtcc taactcagcc cccctcagtg agtgcggctc cggggcagaa agtgacaatc    60
tcgtcagcg gaggctacag ctcttattac ggatggtatc agcagctgcc aggaaccgcc    120
cccaagaccc ttatctacga gactgataaa cggcctcagg ggataccaga caggttttca    180
ggcagtgcgt ctggttcctc tgccacgctc ggcatcaccg ggctgcaaac aggagacgag    240
gcagattatt attgtggagg actgacgcct actcacgcag gaattttggg aggtggaaca    300
aaattaacag tgttg                                                     315

SEQ ID NO: 58           moltype = AA  length = 117
FEATURE                 Location/Qualifiers
REGION                  1..117
                        note = Heavy chain of hzCD19_1218.81.55 (aa)
source                  1..117
                        mol_type = protein
                        organism = synthetic construct
SEQUENCE: 58
EVQLVESGGG LVQPGGSLRL SCAASGFTFS SYDMGWVRQA PGKGLEFVAG IDDDGRYTSY    60
GSAVDGRATI SRDNAKNTVY LQMNSLRAED TAVYYCTRGN AGWIQNWGQG TLVTVSS      117

SEQ ID NO: 59           moltype = AA  length = 105
FEATURE                 Location/Qualifiers
REGION                  1..105
                        note = Light chain of hzCD19_1218.81.55 (aa)
source                  1..105
                        mol_type = protein
                        organism = synthetic construct
SEQUENCE: 59
QSVLTQPPSV SAAPGQKVTI SCSGGYSSYY GWYQQLPGTA PKTLIYESGK RPAGIPDRFS    60
GSASGSSATL GITGLQTGDE ADYYCGGLTP THAGIFGGGT KLTVL                   105

SEQ ID NO: 60           moltype = DNA  length = 351
```

```
FEATURE                 Location/Qualifiers
misc_feature            1..351
                        note = Heavy chain of hzCD19_1218.81.55 (nt)
source                  1..351
                        mol_type = other DNA
                        organism = synthetic construct
SEQUENCE: 60
gaggtgcagc tggtagagtc cggcggcggc ctcgtccaac caggcggctc cctcagattg      60
agctgtgctg ccagcggctt cactttcagc tcttatgaca tgggttgggt gagacaggca     120
cctggcaagg gtctggaatt cgtagccggc atcgacgatg acggtagata caccagttac     180
ggctctgctg tcgatggtcg cgctaccatt agccgagata cgccaagaa taccgtttat      240
cttcaaatga attcactgag ggcagaagac acagccgttt actattgtac tagaggtaac     300
gccgggtgga ttcagaattg gggacagggc acactggtga ccgtgagttc a              351

SEQ ID NO: 61           moltype = DNA length = 315
FEATURE                 Location/Qualifiers
misc_feature            1..315
                        note = Light chain of hzCD19_1218.81.55 (nt)
source                  1..315
                        mol_type = other DNA
                        organism = synthetic construct
SEQUENCE: 61
cagtcagtcc taactcagcc ccctcagtg agtgcggctc cggggcagaa agtgacaatc       60
tcgtgcagcg gaggctacag ctcttattac ggatggtatc agcagctgcc aggaaccgcc    120
cccaagaccc ttatctacga gtcgggaaa cggcctgcgg ggataccaga caggttttca     180
ggcagtgcgt ctggttcctc tgccacgctc ggcatcaccg gctgcaaac aggagacgag      240
gcagattatt attgcggagg actgacgcct actcacgcag aatttttgg aggtggaaca      300
aaattaacag tgttg                                                      315

SEQ ID NO: 62           moltype = AA length = 117
FEATURE                 Location/Qualifiers
REGION                  1..117
                        note = Heavy chain of hzCD19_1218.81.64 (aa)
source                  1..117
                        mol_type = protein
                        organism = synthetic construct
SEQUENCE: 62
EVQLVESGGG LVQPGGSLRL SCAASGFTFS SYDMGWVRQA PGKGLEFVAG IDDDGRYTSY      60
GSAVDGRATI SRDNAKNTVY LQMNSLRAED TAVYYCTRGN AGWIQTWGQG TLVTVSS       117

SEQ ID NO: 63           moltype = AA length = 105
FEATURE                 Location/Qualifiers
REGION                  1..105
                        note = Light chain of hzCD19_1218.81.64 (aa)
source                  1..105
                        mol_type = protein
                        organism = synthetic construct
SEQUENCE: 63
QSVLTQPPSV SAAPGQKVTI SCSGGYSSYY GWYQQLPGTA PKTLIYESQK RPLGIPDRFS      60
GSASGSSATL DITGLQTGDE ADYYCGGLTP THAGIFGGGT KLTVL                    105

SEQ ID NO: 64           moltype = DNA length = 351
FEATURE                 Location/Qualifiers
misc_feature            1..351
                        note = Heavy chain of hzCD19_1218.81.64 (nt)
source                  1..351
                        mol_type = other DNA
                        organism = synthetic construct
SEQUENCE: 64
gaggtgcagc tggtagagtc cggcggcggc ctcgtccaac caggcggctc cctcagattg      60
agctgtgctg ccagcggctt cactttcagc tcttatgaca tgggttgggt gagacaggca     120
cctggcaagg gtctggaatt cgtagccggc atcgacgatg acggtagata caccagttac     180
ggctctgctg tcgatggtcg cgctaccatt agccgagata cgccaagaa taccgtttat      240
cttcaaatga attcactgag ggcagaagac acagccgttt actattgtac tagaggtaac     300
gccgggtgga ttcagacgtg gggacagggc acactggtga ccgtgagttc a              351

SEQ ID NO: 65           moltype = DNA length = 315
FEATURE                 Location/Qualifiers
misc_feature            1..315
                        note = Light chain of hzCD19_1218.81.64 (nt)
source                  1..315
                        mol_type = other DNA
                        organism = synthetic construct
SEQUENCE: 65
cagtcagtcc taactcagcc ccctcagtg agtgcggctc cggggcagaa agtgacaatc       60
tcgtgcagcg gaggctacag ctcttattac ggatggtatc agcagctgcc aggaaccgcc    120
cccaagaccc ttatctacga gtctcagaaa cggcctcttg gataccaga caggttttca     180
ggcagtgcgt ctggttcctc tgccacgctc gacatcaccg gctgcaaac aggagacgag      240
gcagattatt attgcggagg actgacgcct actcacgcag aatttttgg aggtggaaca      300
```

```
aaattaacag tgttg                                                  315

SEQ ID NO: 66          moltype = AA  length = 117
FEATURE                Location/Qualifiers
REGION                 1..117
                       note = Heavy chain of hzCD19_1218.81.79 (aa)
source                 1..117
                       mol_type = protein
                       organism = synthetic construct
SEQUENCE: 66
EVQLVESGGG LVQPGGSLRL SCAASGFTFS SYDMGWVRQA PGKGLEFVAG IDDDGRYTSY    60
GSAVDGRATI SRDNAKNTLY LQMNSLRAED TAVYYCTRGN AGWIDHWGQG TLVTVSS      117

SEQ ID NO: 67          moltype = AA  length = 105
FEATURE                Location/Qualifiers
REGION                 1..105
                       note = Light chain of hzCD19_1218.81.79 (aa)
source                 1..105
                       mol_type = protein
                       organism = synthetic construct
SEQUENCE: 67
QSVLTQPPSV SAAPGQKVTI SCSGGYSSYY GWYQQLPGTA PKTLIYESNK RPSGIPDRFS    60
GSASGSSATL GITGLQTGDE ADYYCGGLTP THAGIFGGGT KLTVL                   105

SEQ ID NO: 68          moltype = DNA  length = 351
FEATURE                Location/Qualifiers
misc_feature           1..351
                       note = Heavy chain of hzCD19_1218.81.79 (nt)
source                 1..351
                       mol_type = other DNA
                       organism = synthetic construct
SEQUENCE: 68
gaagttcagc tggttgaatc tggcggagga ctggtgcaac ctggcggatc tctgagactg    60
tcttgtgccg ccagcggctt caccttcagc agctatgata tgggctgggt ccgacaggcc   120
cctggcaaag acttgagtt tgtggccggc atcgacgacg atggcagata cacaagctac    180
ggctctgccg tggatggcag ggccaccatt agcagagaca cgccaagaa cacccctgtac   240
ctgcagatga acagcctgag agccgaggac accgccgtgt actactgtac aagaggcaac    300
gccggctgga tcgatcactg gggacagggc acactggtca ccgtgtctag c           351

SEQ ID NO: 69          moltype = DNA  length = 315
FEATURE                Location/Qualifiers
misc_feature           1..315
                       note = Light chain of hzCD19_1218.81.79 (nt)
source                 1..315
                       mol_type = other DNA
                       organism = synthetic construct
SEQUENCE: 69
cagtctgtgc tgacacagcc tccatctgtg tctgctgccc ctggccagaa agtgacaatc    60
agctgtagcg gcggctactc cagctactac ggatggtatc agcagctgcc tggcacagcc   120
cctaagacac tgatctacga gagcaacaag aggcccagcg gcatccctga tagattttct   180
ggcagcgcct ctggcagctc tgccacactg ggaattacag gactgcagac aggcgacgag   240
gccgattact attgtggcgg cctgacacct acacacgccg gaattttggc ggaggcacc    300
aagctgacag tgctc                                                   315

SEQ ID NO: 70          moltype = AA  length = 117
FEATURE                Location/Qualifiers
REGION                 1..117
                       note = Heavy chain of hzCD19_1218.81.82 (aa)
source                 1..117
                       mol_type = protein
                       organism = synthetic construct
SEQUENCE: 70
EVQLVESGGG LVQPGGSLRL SCAASGFTFS SYDMGWVRQA PGKGLEFVAG IDDDGRYTSY    60
GSAVDGRATI SRDNAKNTLY LQMNSLRAED TAVYYCTRGN AGWIDAWGQG TLVTVSS      117

SEQ ID NO: 71          moltype = AA  length = 105
FEATURE                Location/Qualifiers
REGION                 1..105
                       note = Light chain of hzCD19_1218.81.82 (aa)
source                 1..105
                       mol_type = protein
                       organism = synthetic construct
SEQUENCE: 71
QSVLTQPPSV SAAPGQKVTI SCSGGYSSYY GWYQQLPGTA PKTLIYESNK RPSGIPDRFS    60
GSASGSSATL GITGLQTGDE ADYYCGQSTR THAGIFGGGT KLTVL                   105

SEQ ID NO: 72          moltype = DNA  length = 351
FEATURE                Location/Qualifiers
misc_feature           1..351
```

|   |   |
|---|---|
|   | note = Heavy chain of hzCD19_1218.81.82 (nt) |
| source | 1..351 |
|   | mol_type = other DNA |
|   | organism = synthetic construct |

SEQUENCE: 72

```
gaagttcagc tggttgaatc tggcggagga ctggtgcaac ctggcggatc tctgagactg    60
tcttgtgccg ccagcggctt caccttcagc agctatgata tgggctgggt ccgacaggcc   120
cctggcaaag gacttgagtt tgtggccggc atcgacgacg atggcagata cacaagctac   180
ggctctgccg tggatggcag ggccaccatt agcagagaca cgccaagaa caccctgtac    240
ctgcagatga acagcctgag agccgaggac accgccgtgt actactgtac aagaggcaac   300
gccggatgga tcgatgcctg gggacagggc acactggtca ccgtgtcaag c            351
```

|   |   |
|---|---|
| SEQ ID NO: 73 | moltype = DNA length = 315 |
| FEATURE | Location/Qualifiers |
| misc_feature | 1..315 |
|   | note = Light chain of hzCD19_1218.81.82 (nt) |
| source | 1..315 |
|   | mol_type = other DNA |
|   | organism = synthetic construct |

SEQUENCE: 73

```
cagtctgtgc tgacacagcc tccatctgtg tctgctgccc ctggccagaa agtgacaatc    60
agctgtagcg gcggctactc cagctactac ggatgctatc agcagctgcc tggcacagcc   120
cctaagacac tgatctacga gagcaacaag aggcccagcg gcatccctga tagattttct   180
ggcagcgcct ctgcagctc tgccacactg gaattacag actgcagac aggcgacgag     240
gccgattact actgtggcca gtctacaaga acccacgccg aatctttgg cggaggcaca    300
aaactgacag tgctc                                                   315
```

|   |   |
|---|---|
| SEQ ID NO: 74 | moltype = DNA length = 669 |
| FEATURE | Location/Qualifiers |
| misc_feature | 1..669 |
|   | note = CAR1 construct without scFv (nt) |
| source | 1..669 |
|   | mol_type = other DNA |
|   | organism = synthetic construct |

SEQUENCE: 74

```
acaacgacac tgctcccag accgcctact cccgccccaa ccattgcatc tcagccactc    60
tctctgagac ccgaagcgtg tagacctgcg gccgggggcg ctgtccacac aagaggctta   120
gacttcgcct gcgatatcta tatctgggcc ccactcgcag gcacttgtgg agtgctgctg   180
ctttcactcg tgataaccct gtactgcaaa agggggagaa agaagctgct gtatattttt   240
aaacaaccat ttatgagacc tgttcagact acccaggaag aagacggttg tagttgcaga   300
ttccccgagg aggaagaagg aggttgcgag ttgagagtaa agttcagcag atccgcagat   360
gcccctgctt accagcaggg tcaaaaccag ctttacaacg agctgaattt aggtagaaga   420
gaggaatatg acgtgttgga taaaagaaga ggaagagacc cggaaatggg cggcaagcct   480
cgaagaaaaa atcccaaga gggactctac aatgagctgc agaaggacaa aatggctgaa    540
gcctacagcg agatcggcat gaagggagaa agacgcagag gaaagggca tgatgggctt    600
tatcagggct gtccaccgc tacaaaggat acttatgacg cactacacat gcaggccctg   660
ccacccgt                                                           669
```

|   |   |
|---|---|
| SEQ ID NO: 75 | moltype = AA length = 223 |
| FEATURE | Location/Qualifiers |
| REGION | 1..223 |
|   | note = CAR1 construct without scFv (aa) |
| source | 1..223 |
|   | mol_type = protein |
|   | organism = synthetic construct |

SEQUENCE: 75

```
TTTPAPRPPT PAPTIASQPL SLRPEACRPA AGGAVHTRGL DFACDIYIWA PLAGTCGVLL    60
LSLVITLYCK RGRKKLLYIF KQPFMRPVQT TQEEDGCSCR FPEEEEGGCE LRVKFSRSAD   120
APAYQQGQNQ LYNELNLGRR EEYDVLDKRR GRDPEMGGKP RRKNPQEGLY NELQKDKMAE   180
AYSEIGMKGE RRRGKGHDGL YQGLSTATKD TYDALHMQAL PPR                     223
```

|   |   |
|---|---|
| SEQ ID NO: 76 | moltype = DNA length = 651 |
| FEATURE | Location/Qualifiers |
| misc_feature | 1..651 |
|   | note = CAR2 construct without scFv (nt) |
| source | 1..651 |
|   | mol_type = other DNA |
|   | organism = synthetic construct |

SEQUENCE: 76

```
atcgaggtga tgtaccctcc tcccatctc gataacgaga atctaacgg caccatcatc     60
catgtgaaag ggaaacacct ctgccccttca ccactcttcc aggtccgag caagccaatt   120
tatatctggg caccgttggc ggggacttgc ggagtgcttt actttcact ggttattacg    180
ctgtactgta aacgcggtcg gaagaagctc ctttacattt tcaagcagcc tttatgcgc    240
ccagtcagaa ccacacagga ggaagatggc tgtagttgca gatttccga ggaagaagag    300
ggagggtgtg aactgagagt caaattcagc cgttccgctg atgccccagc ctatcaacag   360
gggcagaatc aactgtataa tgaattgaat ctgggcagga gaagaata cgacgtcctg    420
gataagaggc gaggcagaga ccccgagatg ggcggtaaac cccggcgaaa gaaccccag    480
gaaggcctgt acaacgagct gcagaaggac aagatggctg aggcctactc gaaatagga    540
atgaaggggg agagaaggag aggcaaagga catgacggc tgtaccaggg actgtctaca    600
```

```
gctactaagg acacctatga tgcattgcac atgcaagccc tacccccctag a          651
```

| SEQ ID NO: 77 | moltype = AA   length = 217 |
|---|---|
| FEATURE | Location/Qualifiers |
| REGION | 1..217 |
| | note = CAR2 construct without scFv (aa) |
| source | 1..217 |
| | mol_type = protein |
| | organism = synthetic construct |

SEQUENCE: 77
```
IEVMYPPPYL DNEKSNGTII HVKGKHLCPS PLFPGPSKPI YIWAPLAGTC GVLLLSLVIT   60
LYCKRGRKKL LYIFKQPFMR PVQTTQEEDG CSCRFPEEEE GGCELRVKFS RSADAPAYQQ  120
GQNQLYNELN LGRREEYDVL DKRRGRDPEM GGKPRRKNPQ EGLYNELQKD KMAEAYSEIG  180
MKGERRRGKG HDGLYQGLST ATKDTYDALH MQALPPR                          217
```

| SEQ ID NO: 78 | moltype = DNA   length = 1227 |
|---|---|
| FEATURE | Location/Qualifiers |
| misc_feature | 1..1227 |
| | note = CAR3 construct without scFv (nt) |
| source | 1..1227 |
| | mol_type = other DNA |
| | organism = synthetic construct |

SEQUENCE: 78
```
gaaccaaaga gctgcgataa gacccacacc tgtccgccat gtcccgctcc cgaactgctg   60
ggtgggccca gcgtgttcct gtttcctccc aagcccaagg atacgcttat gatctcaaga  120
acgcccgagg tgacatgcgt ggtggttgat gtgagccatg aagaccccga ggtgaagttc  180
aactggtatg tggacggcgt ggaggtgcat aacgctaaaa caaagccctag agaagagcag  240
tataactcga cctacagggt ggttagcgtg ttaactgttc tgcatcagga ctggctcaat  300
ggcaaggagt acaaatgtaa agtgtctaat aaagccctgc ccgcccccat tgagaaaact  360
attacaaggc ctaaaggaca gccccagaga ccccaggtct atacctttgcc tccatctaga  420
gatgaattaa caaaaaaacca ggtatctctt acatgcctgg tgaagggggtt ttacccctca  480
gacatcgccg tggagtggga aagtaatgga cagcccgaaa ataattataa gaccacacca  540
cccgtgctgg acagcgatgg cagcttcttt ctgtacagca aattgacagt ggataagtcc  600
agatgcaaac aagggaatgt cttctcatgt agcgtgatgc atgaggccct gcataaccac  660
tacactcaga gtccccgtag tcttagcccc ggcatataca tctgggcacc tctcgccgga  720
acctgtggtg tattactgct gagccttgtg attactctgt attgcaaaag aggccggaag  780
aagctgctgt acatctttaa gcagcccttc atgcggccgg ttcagacaac ccaggaggag  840
gatggctgca gctgccgatt tcccgaagaa gaagagggcg gctgcgagct gagagtgaaa  900
ttctcaagaa gtgctgacgc accagcctac agcaaggcc agaaccagct gtataacgag  960
ctaaatctgg gcagaagaga agagtacgac gtactggaca gcgcagagg tagagatccc 1020
gaaatggggg gcaaaccgcg gagaaagaat cctcaggagg gtctgtataa cgagctgcaa 1080
aaggataaaa tggcagaggc gtacagcgaa atcggcatga aaggcgagcg acgccgcggc 1140
aaagggcacg acggcttgta tcagggactt agcactgcca ccaaggacac ttacgatgcc 1200
ctccacatgc aagctctgcc cccaaga                                    1227
```

| SEQ ID NO: 79 | moltype = AA   length = 409 |
|---|---|
| FEATURE | Location/Qualifiers |
| REGION | 1..409 |
| | note = CAR3 construct without scFv (aa) |
| source | 1..409 |
| | mol_type = protein |
| | organism = synthetic construct |

SEQUENCE: 79
```
EPKSCDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GIYIWAPLAG  240
TCGVLLLSLV ITLYCKRGRK KLLYIFKQPF MRPVQTTQEE DGCSCRFPEE EEGGCELRVK  300
FSRSADAPAY QQGQNQLYNE LNLGRREEYD VLDKRRGRDP EMGGKPRRKN PQEGLYNELQ  360
KDKMAEAYSE IGMKGERRRG KGHDGLYQGL STATKDTYDA LHMQALPPR             409
```

| SEQ ID NO: 80 | moltype = DNA   length = 675 |
|---|---|
| FEATURE | Location/Qualifiers |
| misc_feature | 1..675 |
| | note = CAR4 construct without scFv (nt) |
| source | 1..675 |
| | mol_type = other DNA |
| | organism = synthetic construct |

SEQUENCE: 80
```
accaccaccc ctgcaccaag acctcctact cccgctccga cgatcgctag ccaacctctg   60
agcctgaggc cagaggcgtg tagaccagca gccggcgggg ccgttcacac aagaggcctg  120
gacttcgcct cgacttctg ggtgctggtt gtggtcggcg gagtgttagc gtgctattcc  180
ctactcgtga ccgtcgcttt tataatcttt tgggtcagaa gtaagagatc tagactcctg  240
catgcgact acatgaatat gactcctaga agacccggtc cgacaagaaa gcactatcag  300
ccctatgctc cacccagaga ttttgcagcc tacagatcaa gagtaaaatt ctctagatcc  360
gcagacgccc cagcatacca gcaaggacaa atcagttgt acaacgaact gaaccttggt  420
agaagggagg agtatgatgt gctggataag agaagaggca gagatcccga atggggggg  480
aaaccaagac ggaagaaccc ccaggaggga ttgtataatg aactgcagaa agacaagatg  540
gccgaagctt atagtgagat tgggatgaag gcgagagaa aagaggaaa aggtcatgac  600
```

```
ggcttgtacc agggactttc aacagccact aaagatacat atgatgctct gcacatgcag    660
gccctccccc ctaga                                                     675
```

SEQ ID NO: 81         moltype = AA  length = 225
FEATURE              Location/Qualifiers
REGION               1..225
                      note = CAR4 construct without scFv (aa)
source               1..225
                      mol_type = protein
                      organism = synthetic construct

```
SEQUENCE: 81
TTTPAPRPPT PAPTIASQPL SLRPEACRPA AGGAVHTRGL DFACDFWVLV VVGGVLACYS     60
LLVTVAFIIF WVRSKRSRLL HSDYMNMTPR RPGPTRKHYQ PYAPPRDFAA YRSRVKFSRS    120
ADAPAYQQGQ NQLYNELNLG RREEYDVLDK RRGRDPEMGG KPRRKNPQEG LYNELQKDKM    180
AEAYSEIGMK GERRRGKGHD GLYQGLSTAT KDTYDALHMQ ALPPR                    225
```

SEQ ID NO: 82         moltype = DNA  length = 648
FEATURE              Location/Qualifiers
misc_feature       1..648
                      note = CAR5 construct without scFv (nt)
source               1..648
                      mol_type = other DNA
                      organism = synthetic construct

```
SEQUENCE: 82
actaccaccc cagcgcccag acctcccact cctgctccta ccatcgcaag ccagccgctg     60
tctcttagac cagaggcctg ccgacccgct gccggtgggg cagtgcacac agaggctctg    120
gacttcgcct gcgatttctg gctccccatt ggctgtgcgg cattcgtcgt cgtttgtatc    180
ctgggatgca ttctgatatg ttggttgacc aaaaagaagt attcaagcag tgtgcatgat    240
cctaatggcg agtacatgtt tatgagagca gttaatacag ctaagaaaag cagattaaca    300
gatgtaactc tcagagtgaa gttttctaga tccgctcagt cccccagcata ccagcaagga    360
cagaaccagt tatataacga gctcaacctg ggagaagaag aagagtatga tgtgctggac    420
aagcgcagag ggagagaccc agaaatgggg ggcaagccta agaaaagaa tccgcaagag    480
ggcctataca cgaactgca gaaagacaaa atggccgagg cctatagcga aatcgggatg    540
aagggagaaa gaaggagagg caaaggacat gatgggttgt accagggcct ctccacagct    600
acaaaagaca cctacgacgc cctgcacatg caggcccttc ccccaaga                648
```

SEQ ID NO: 83         moltype = AA  length = 216
FEATURE              Location/Qualifiers
REGION               1..216
                      note = CAR5 construct without scFv (aa)
source               1..216
                      mol_type = protein
                      organism = synthetic construct

```
SEQUENCE: 83
TTTPAPRPPT PAPTIASQPL SLRPEACRPA AGGAVHTRGL DFACDFWLPI GCAAFVVVCI     60
LGCILICWLT KKKYSSSVHD PNGEYMFMRA VNTAKKSRLT DVTLRVKFSR SADAPAYQQG    120
QNQLYNELNL GRREEYDVLD KRRGRDPEMG GKPRRKNPQE GLYNELQKDK MAEAYSEIGM    180
KGERRRGKGH DGLYQGLSTA TKDTYDALHM QALPPR                              216
```

SEQ ID NO: 84         moltype = DNA  length = 801
FEATURE              Location/Qualifiers
misc_feature       1..801
                      note = CAR6 construct without scFv (nt)
source               1..801
                      mol_type = other DNA
                      organism = synthetic construct

```
SEQUENCE: 84
acgaccactc cagcccctag acctcccaca cccgctccca caattgcttc acagccattg     60
tcactcagac cagaggcctg cagacctgca gccggaggcg ccgtgcacac cagaggcttg    120
gacttcgctt gtgattttttg ggttctgttt gtcgtcggcg gagtgctggc atgctatagc    180
ctgctcgtaa ctgtggcttt catcatttttc tgggtgagaa gcaagagatc cagactgctc    240
catagcgatt acatgaatat gaccccacga agacctggac ccaccagaaa gcattaccaa    300
ccttacgcgc cacctagaga ttttgcagcc tacaggtcta aaagagggag aaagaagctt    360
cttttacatct ttaaacagcc attcatgaga ccggtccaaa ccagcagga agaagacggc    420
tgttcttgca gattcccgga ggaagaggag ggggggtgtg agttaagagt gaagttttct    480
aggagtgctg atgcccctgc ctaccaacaa ggccagaacc agctttataa tgaactgaac    540
ctgggaagaa gagaagaata tgacgtgcta gacaagagaa gaggcagaga tccagaaatg    600
gggggtaagc ccgtcgcaa aaatccccag gagggtctgt acaacgaact gcagaaagac    660
aaaatggctg aggcatatag tgagatcggg atgaaggga gaggagaaag aggaaaaggt    720
cacgacggtc tctatcaggg cctgtccact gccaccaaag acacatatga tgcgttgcac    780
atgcaggccc tgcccccag g                                              801
```

SEQ ID NO: 85         moltype = AA  length = 267
FEATURE              Location/Qualifiers
REGION               1..267
                      note = CAR6 construct without scFv (aa)
source               1..267
                      mol_type = protein
                      organism = synthetic construct

```
SEQUENCE: 85
TTTPAPRPPT PAPTIASQPL SLRPEACRPA AGGAVHTRGL DFACDFWVLV VVGGVLACYS      60
LLVTVAFIIF WVRSKRSRLL HSDYMNMTPR RPGPTRKHYQ PYAPPRDFAA YRSKRGRKKL     120
LYIFKQPFMR PVQTTQEEDG CSCRFPEEEE GGCELRVKFS RSADAPAYQQ GQNQLYNELN     180
LGRREEYDVL DKRRGRDPEM GGKPRRKNPQ EGLYNELQKD KMAEAYSEIG MKGERRRGKG     240
HDGLYQGLST ATKDTYDALH MQALPPR                                        267

SEQ ID NO: 86           moltype = DNA   length = 774
FEATURE                 Location/Qualifiers
misc_feature            1..774
                        note = CAR7 construct without scFv (nt)
source                  1..774
                        mol_type = other DNA
                        organism = synthetic construct
SEQUENCE: 86
actaccacgc cgcccccag gcccctaca ccagcaccaa ccattgcaag tcagcccctg       60
tcactcagac cggaagcttg ccgcccggca gctgggggtg ccgtccacac aagaggactc    120
gacttcgcgt gtgatttctg gctccctata gggtgtgccg cattcgtcgt tgtgtgcatc    180
ctgggatgta tcctgatctg ctggctgact aagaagaagt actcctctag cgtgcacgac    240
ccaaacggcg aatacatgtt catgagagct gtgaatactg ccaagaaatc aaggctgacc    300
gatgtgacgc tgaaacgtgg gagaaagaag ttgttatata ttttttaaaca gccttttatg   360
agaccagtgc aaaacaactca ggaggaagac ggctgttctt gcagatttcc tgaggaagag   420
gagggaggct gcgagctcag ggttaaattt tctagaagcg ctgacgcacc cgcgtaccag    480
cagggacaga accaactgta caatgagctt aacctgggca gacgagaaga atatgatgta    540
ttggataaaa aagaggaag agatcctgag atgggtggca gcctagacg taagaaccca      600
cagggggcc tgtataatga gctacagaag gacaaaatgc ctgaagccta cagcgagatt     660
ggtatgaaag gcgagagaag aagagggaa ggccatgacg gtctgtatca aggcttgtcc    720
accgccacaa aggataccta cgacgcccctt catatgcagg cccttcctcc caga         774

SEQ ID NO: 87           moltype = AA   length = 258
FEATURE                 Location/Qualifiers
REGION                  1..258
                        note = CAR7 construct without scFv (aa)
source                  1..258
                        mol_type = protein
                        organism = synthetic construct
SEQUENCE: 87
TTTPAPRPPT PAPTIASQPL SLRPEACRPA AGGAVHTRGL DFACDFWLPI GCAAFVVVCI     60
LGCILICWLT KKKYSSSVHD PNGEYMFMRA VNTAKKSRLT DVTLKRGRKK LLYIFKQPFM    120
RPVQTTQEED GCSCRFPEEE EGGCELRVKF SRSADAPAYQ QGQNQLYNEL NLGRREEYDV    180
LDKRRGRDPE MGGKPRRKNP QEGLYNELQK DKMAEAYSEI GMKGERRRGK GHDGLYQGLS    240
TATKDTYDAL HMQALPPR                                                  258

SEQ ID NO: 88           moltype = DNA   length = 63
FEATURE                 Location/Qualifiers
misc_feature            1..63
                        note = T2A Nucleotide sequence
source                  1..63
                        mol_type = other DNA
                        organism = synthetic construct
SEQUENCE: 88
ggctccggcg agggcagggg aagtcttcta acatgcgggg acgtggagga aaatcccggc     60
cca                                                                   63

SEQ ID NO: 89           moltype = DNA   length = 720
FEATURE                 Location/Qualifiers
misc_feature            1..720
                        note = GFP Nucleotide sequence
source                  1..720
                        mol_type = other DNA
                        organism = synthetic construct
SEQUENCE: 89
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcaccta cggcgtgcag tgcttcagcc cctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaag gtctatatca ccgccgacaa gcagaagaac    480
ggcatcaagg tgaacttcaa gacccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720

SEQ ID NO: 90           moltype = DNA   length = 783
FEATURE                 Location/Qualifiers
misc_feature            1..783
                        note = T2A-GFP Nucleotide sequence
```

```
source                  1..783
                        mol_type = other DNA
                        organism = synthetic construct
SEQUENCE: 90
ggctccggcg agggcagggg aagtcttcta acatgcgggg acgtggagga aaatcccggc   60
ccaatggtga gcaagggcga ggagctgttc accggggtgg tgcccatcct ggtcgagctg  120
gacggcgacg taaacggcca caagttcagc gtgtccggcg agggcgaggg cgatgccacc  180
tacggcaagc tgaccctgaa gttcatctgc accaccggca agctgcccgt gccctggccc  240
accctcgtga ccaccttcac ctacggcgtg cagtgcttcg cccgctaccc cgaccacatg  300
aagcagcacg acttcttcaa gtccgccatg cccgaaggct acgtccagga gcgcaccatc  360
ttcttcaagg acgacggcaa ctacaagacc cgcgccgagg tgaagttcga gggcgacacc  420
ctggtgaacc gcatcgagct gaagggcatc gacttcaagg aggacggcaa catcctgggg  480
cacaagctgg agtacaacta caacagccac aaggtctata tcaccgccga caagcagaag  540
aacggcatca aggtgaactt caagacccgc cacaacatcg aggacggcag cgtgcagctc  600
gccgaccact accagcagaa cacccccatc ggcgacggcc ccgtgctgct gcccgacaac  660
cactacctga gcacccagtc cgccctgagc aaagacccca acgagaagcg cgatcacatg  720
gtcctgctgg agttcgtgac cgccgccggg atcactctcg gcatggacga gctgtacaag  780
taa                                                                 783

SEQ ID NO: 91           moltype = DNA  length = 1184
FEATURE                 Location/Qualifiers
misc_feature            1..1184
                        note = EF-1 alpha Nucleotide sequence
source                  1..1184
                        mol_type = other DNA
                        organism = synthetic construct
SEQUENCE: 91
tgtgaggctc cggtgcccgt cagtgggcag agcgcacatc gcccacagtc ccgagaagt    60
tgggggggagg ggtcggcaat tgaaccggtg cctagagaag tggcgcgggg gtaaactggg  120
aaagtgatgt cgtgtactgg ctccgccttt ttcccgaggg tggggggagaa ccgtatataa  180
gtgcagtagt cgccgtgaac gttctttttc gcaacgggtt tgccgccaga acacaggtaa  240
gtgccgtgtg tggttcccgc gggcctggcc tctttacggg ttatggccct tgcgtgcctt  300
gaattacttc cacctggctg cagtacgtga ttcttgatcc cgagcttcgg gttggaagtg  360
ggtgggagag ttcgaggcct tgcgcttaag gagccccttc gcctcgtgct tgagttgagg  420
cctggcctgg gcgctgggc cgccgcgtgc gaatctggtg gcaccttcgc gcctgtcctg  480
ctgctttcga taagtctcta gccatttaaa attttgatg acctgctgcg acgctttttt  540
tctggcaaga tagtcttgta aatgcgggcc aagatctgca cactggtatt tcggtttttg  600
gggccgcggg cggcgacggg gcccgtgcgt cccagcgcac atgttcggcg aggcggggcc  660
tgcgagccgc gccaccgaga atcggacggg ggtagtctca agctgcccgg cctgctctgg  720
tgcctggcct cgcgccgccg tgtatcgccc cgccctgggc ggcaaggctg gcccggtcgg  780
caccagttgc gtgagcggaa agatggccgc ttccggcc tgctgcaggg agctcaaaat  840
ggaggacgcg gcgctcggga gagcgggcgg gtgagtcacc cacacaaagg aaaagggcct  900
ttccgtcctc agccgtcgct tcatgtgact ccacggagga tccgctccgc tccaggcacc  960
tcgattagtt ctcgagcttt tggagtacgt cgtctttagg ttgggggggag ggg ttttatg 1020
cgatggagtt tccccacact gagtgggtgg agactgaagt taggccagct ggcacttga  1080
tgtaattctc cttggaattt gcccttttg agtttgatc ttggttcatt ctcaagcctc  1140
agacagtggt tcaaagtttt tttcttccat ttcaggtgtc gtga                  1184

SEQ ID NO: 92           moltype = AA  length = 556
FEATURE                 Location/Qualifiers
REGION                  1..556
                        note = amino acid sequence of hCD19 (UniProtKB: P15391)
source                  1..556
                        mol_type = protein
                        organism = synthetic construct
SEQUENCE: 92
MPPPRLLFFL LFLTPMEVRP EEPLVVKVEE GDNAVLQCLK GTSDGPTQQL TWSRESPLKP   60
FLKLSLGLPG LGIHMRPLAI WLFIFNVSQQ MGGFYLCQPG PPSEKAWQPG WTVNVEGSGE  120
LFRWNVSDLG GLGCGLKNRS SEGPSSPSGK LMSPKLYVWA KDRPEIWEGE PPCLPPRDSL  180
NQSLSQDLTM APGSTLWLSC GVPPDSVSRG PLSWTHVHPK GPKSLLSLEL KDDRPARDMW  240
VMETGLLLPR ATAQDAGKYY CHRGNLTMSF HLEITARPVL WHWLLRTGGW KVSAVTLAYL  300
IFCLCSLVGI LHLQRALVLR RKRKRMTDPT RRFFKVTPPP GSGPQNQYGN VLSLPTPTSG  360
LGRAQRWAAG LGGTAPSYGN PSSDVQADGA LGSRSPPGVG PEEEEGEGYE EPDSEEDSEF  420
YENDSNLGQD QLSQDGSGYE NPEDEPLGPE DEDSFSNAES YENEDEELTQ PVARTMDFLS  480
PHGSAWDPSR EATSLGSQSY EDMRGILYAA PQLRSIRGQP GPNHEEDADS YENMDNPDGP  540
DPAWGGGGRM GTWSTR                                                   556

SEQ ID NO: 93           moltype = AA  length = 537
FEATURE                 Location/Qualifiers
REGION                  1..537
                        note = amino acid sequence of cCD19 (UniProtKB: G7Q0T7)
source                  1..537
                        mol_type = protein
                        organism = synthetic construct
SEQUENCE: 93
MPPPCLLFFL LFLTPMEVRP QEPLVVKVEE GDNAVLQCLE GTSDGPTQQL VWCRDSPFEP   60
FLNLSLGLPG MGIRMGPLGI WLLIFNVSNQ TGGFYLCQPG LPSEKAWQPG WTVSVEGSGE  120
LFRWNVSDLG GLGCGLKNRS SEGPSSPSGK LNSSQLYVWA KDRPEMWEGE PVCGPPRDSL  180
NQSLSQDLTM APGSTLWLSC GVPPDSVSRG PLSWTHVRPK GPKSSLLSLE LKDDRPDRDM  240
```

```
WVVDTGLLLT RATAQDAGKY YCHRGNWTKS FYLEITARPA LVLRRKRKRM TDPTRRFFKV    300
TPPPGSGPQN QYGNVLSLPT PTSGLGRAQR WAAGLGGTAP SYGNPSSDVQ VDGAVGSRSP    360
PEAGPEEEEG EGYEEPDSEE GSEFYENDSN FGQDQLSQDG SGYENPEDEP LGPEDEDSFS    420
NAESYENEDE ELTQPVARTM DFLSPHGSAW DPSREATSLG CTSRALASNS PSPAQAGSQS    480
YEDMRGLLYA APQLRTIRGQ PGPNHEEDAD SYENMDNPDG PDPAWGGGGR MGTWSAR       537
```